US012760288B2

(12) United States Patent
Gao et al.

(10) Patent No.: US 12,760,288 B2
(45) Date of Patent: Oct. 13, 2026

(54) METHOD FOR TARGETED MODIFICATION OF A PLANT GENOME SEQUENCE

(71) Applicant: Qi Biodesign Biotechnology Company Limited, Beijing (CN)

(72) Inventors: Caixia Gao, Beijing (CN); Qiupeng Lin, Beijing (CN); Yuan Zong, Beijing (CN); Shuai Jin, Beijing (CN); Chenxiao Xue, Beijing (CN)

(73) Assignee: Qi Biodesign Biotechnology Company Limited, Beijing (CN)

(*) Notice: Subject to any disclaimer, the term of this patent is extended or adjusted under 35 U.S.C. 154(b) by 1084 days.

(21) Appl. No.: 17/773,426

(22) PCT Filed: Sep. 25, 2020

(86) PCT No.: PCT/CN2020/117736
§ 371 (c)(1),
(2) Date: Apr. 29, 2022

(87) PCT Pub. No.: WO2021/082830
PCT Pub. Date: May 6, 2021

(65) Prior Publication Data

US 2023/0075587 A1 Mar. 9, 2023

(30) Foreign Application Priority Data

Nov. 1, 2019 (CN) ......................... 201911062005.6
Jan. 14, 2020 (CN) ......................... 202010036374.4

(51) Int. Cl.
*C12Q 1/686* (2018.01)
*C12N 9/12* (2006.01)
(Continued)

(52) U.S. Cl.
CPC ........... *C12N 15/62* (2013.01); *C12N 9/1276* (2013.01); *C12N 15/8213* (2013.01); *C12Q 1/686* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 11,447,770 B1* | 9/2022 | Liu | ........................ | C12N 15/11 |
| 12,435,330 B2* | 10/2025 | Liu | .......................... | C12N 9/22 |
| 2014/0342456 A1* | 11/2014 | Mali | ...................... | C12N 15/11 |
| | | | | 435/254.2 |

FOREIGN PATENT DOCUMENTS

| | | |
|---|---|---|
| CN | 107109422 A | 8/2017 |
| CN | 111378051 A | 7/2020 |

(Continued)

OTHER PUBLICATIONS

Anzalone AV, Randolph PB, Davis JR, Sousa AA, Koblan LW, Levy JM, Chen PJ, Wilson C, Newby GA, Raguram A, Liu DR. Search-and-replace genome editing without double-strand breaks or donor DNA. Nature. Dec. 2019;576(7785):149-157. doi: 10.1038/s41586-019-1711-4. Epub Oct. 21, 2019. PMID: 31634902 (Year: 2019).*

(Continued)

*Primary Examiner* — Evelyn Y Pyla
*Assistant Examiner* — Jagamya Vijayaraghavan
(74) *Attorney, Agent, or Firm* — Troutman Pepper Locke LLP

(57) ABSTRACT

The present invention relates to the field of plant genetic engineering. Specifically, the present invention relates to a method for targeted modification of a plant genome sequence. More specifically, the present invention relates to a method for targeted modification of a specific sequence in the plant genome into a target sequence of interest by a nuclease-reverse transcriptase fusion protein guided by a
(Continued)

guide RNA, a genetically-modified plant produced by said method, and progenies of said plant.

19 Claims, 21 Drawing Sheets

Specification includes a Sequence Listing.

(51) Int. Cl.

| | |
|---|---|
| ***C12N 15/62*** | (2006.01) |
| ***C12N 15/82*** | (2006.01) |
| ***C12Q 1/6876*** | (2018.01) |

(56) References Cited

FOREIGN PATENT DOCUMENTS

| | | | | |
|---|---|---|---|---|
| CN | 111471745 A * | 7/2020 | ........... C12Q 1/6806 |
| WO | 2014/188688 | 11/2014 | |
| WO | 2018/149418 A1 | 8/2018 | |
| WO | 2020/191249 A1 | 9/2020 | |
| WO | 2021/072328 A1 | 4/2021 | |
| WO | 2021/081357 A1 | 4/2021 | |

OTHER PUBLICATIONS

Belhaj K, Chaparro-Garcia A, Kamoun S, Patron NJ, Nekrasov V. Editing plant genomes with CRISPR/Cas9. Curr Opin Biotechnol. Apr. 2015;32:76-84. doi: 10.1016/j.copbio.2014.11.007. Epub Nov. 29, 2014. PMID: 25437637. (Year: 2019).*

Nelson, J.W., Randolph, P.B., Shen, S.P. et al. Engineered pegRNAs improve prime editing efficiency. Nat Biotechnol 40, 402-410 (2022). https://doi.org/10.1038/s41587-021-01039-7 (Year: 2022).*

LeBlanc C, Zhang F, Mendez J, Lozano Y, Chatpar K, Irish VF, Jacob Y. Increased efficiency of targeted mutagenesis by CRISPR/Cas9 in plants using heat stress. Plant J. Jan. 2018;93(2):377-386. doi: 10.1111/tpj. 13782. Epub Dec. 22, 2017. PMID: 29161464. (Year: 2018).*

Wilson Low, O'Brien AR, Bauer DC. The Current State and Future of CRISPR-Cas9 gRNA Design Tools. Front Pharmacol. Jul. 12, 2018;9:749. doi: 10.3389/fphar.2018.00749. PMID: 30050439; PMCID: PMC6052051. (Year: 2018).*

Yang L, Yang B, Chen J. One Prime for All Editing. Cell. Dec. 12, 2019;179(7):1448-1450. doi: 10.1016/j.cell.2019.11.030. PMID: 31835025. (Year: 2019).*

Kurt IC, Zhou R, Iyer S, Garcia SP, Miller BR, Langner LM, Grünewald J, Joung JK. CRISPR C-to-G base editors for inducing targeted DNA transversions in human cells. Nat Biotechnol. Jan. 2021;39(1):41-46. doi: 10.1038/s41587-020-0609-x. Epub Jul. 20, 2020. PMID: 32690971; PMCID: PMC7854778. (Year: 2020).*

Anonymous, "Scientist David Liu takes your questions on CRISPR and prime editing", 2019, XP055804296, Retrieved from the internet: URL: https://www.statnews.com/2019/11/06/questions-david-liu-crispr-prime-editing-answers/. [Retrieved on May 14, 2021].

Ni et al., "Progress on Cloning and Functional Study of Plant Gene Promoters", Journal of Plant Genetic Resources, 2008, vol. 9, No. 3, pp. 385-391.

European Search Report and Opinion issued in EP 20882981 dated Feb. 6, 2024.

Gao et al., "Self-processing of ribozyme-flanked RNAs into guide RNAs in vitro and in vivo for CRISPR-mediated genome editing", Journal of Integrative Plant Biology, vol. 56, Issue 4, pp. 343-349 (2014).

International Search Report and Written Opinion Issued in PCT/CN2020/117736 dated Jan. 4, 2021.

Lin et al., "Prime genome editing in rice and wheat", Nature Biotechnology, vol. 38, No. 5, pp. 582-585 (2020).

Anzalone et al., "Search-and-replace genome editing without double-strand breaks or donor DNA", Nature, vol. 576, No. 7785, pp. 149-157 (2019).

Lin et al., "High-efficiency prime editing with optimized, paired pegRNAs in plants", Nature Biotechnology, 2021, vol. 39, pp. 923-927.

Wang et al., "Advances in targeted replacement genome editing in plants", Chinese Journal of Biotechnology, 2017, vol. 33, No. 10, pp. 1723-1732, DOI: 10.13345/j.cjb. 170192, with English language abstract and partial translation.

Wang and Zhao, "Progress and Challenge of Crop Genetic Improvement via Genome Editing", Scientia Agricultura Sinica, 2018, vol. 51, No. 1, pp. 1-16, doi: 103864/j.issn.0578-1752.2018.01.001, with English language abstract and partial translation.

Li and Xie, "Recent progresses in CRISPR genome editing in plants", Chinese Journal of Biotechnology, 2017, vol. 33, No. 10, pp. 1700-1711, DOI: 10.13345/j.cjb.170171, with English language abstract and partial translation.

Wang et al., "A plant-specific module for homologous recombination repair", PNAS, 2022, vol. 119, No. 16, e2202970119 12 pages, https//doi.org/10.1073/pnas.2202970119.

Tang et al., "Conservation and Specificity of DNA Double-strand Break Repair in Plants", Plant Physiology and Molecular Biology, 2006, vol. 42, No. 6, pp. 1224-1230, with English language abstract and partial translation.

Meng et al., "RNA-binding protein MAC5A interacts with the 26S proteasome to regulate DNA damage repsonse in Arabidopsis", Plant Physiology, 2023, vol. 191, pp. 446-462, https://doi.org/10.1093/plphys/kiac510.

Chen et al., "Enhanced prime editing systems by manipulating cellular determinants of editing outcomes", Cell, 2021, Vo. 184, pp. 5635-5652 https://doi.org/10.1016/j.cell.2021.09.018.

Tang et al., "Plant Prime Editors Enable Precise Gene Editing in Rice Cells", Molecular Plant, 2020, vol. 13, pp. 667-670.

Xu et al., "Identification of herbicide resistance OsACC1 mutations via in planta prime-editing-library screening in rice", Nature Plants, 2021, vol. 7, pp. 888-892, https://doi.org/10.1038/s41477-021-00942-w.

* cited by examiner

*OsCDC48-T1* (+1-6 CTCCGG del, PPE3, nicking sgRNA site +37)

*OsALS-T2* (+3 G to T, PPE3, nicking sgRNA site +33)

*OsCDC48-T1* (+3-5 CCG to TAA, PPE3, nicking sgRNA site +78)

*OsCDC48-T1* (+1-6 CTCCGG del, PPE3, nicking sgRNA site +37)

SEQUENCE LISTING

<160> NUMBER OF SEQ ID NOS: 310

<210> SEQ ID NO 1
<211> LENGTH: 1368
<212> TYPE: PRT
<213> ORGANISM: Streptococcus pyogenes

<400> SEQUENCE: 1

-continued

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
```

-continued

```
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845
```

-continued

```
Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245
```

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 2
<211> LENGTH: 1368
<212> TYPE: PRT
<213> ORGANISM: Artificial Sequence
<220> FEATURE:
<223> OTHER INFORMATION: nCas9(H840A) amino acid sequence

<400> SEQUENCE: 2

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
```

```
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080
```

```
Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 3
<211> LENGTH: 678
<212> TYPE: PRT
<213> ORGANISM: Artificial sequence
<220> FEATURE:
<223> OTHER INFORMATION: wildtype M-MLV amino acid sequence

<400> SEQUENCE: 3

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60
```

```
Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480
```

```
Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575

Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675


<210> SEQ ID NO 4
<211> LENGTH: 678
<212> TYPE: PRT
<213> ORGANISM: Artificial sequence
<220> FEATURE:
<223> OTHER INFORMATION: amino acid sequence of the M-MLV of the
      invention

<400> SEQUENCE: 4

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160
```

```
Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Lys Ala Gly Phe Cys Arg Leu Phe Ile Pro Gly Phe Ala Glu
305                 310                 315                 320

Met Ala Ala Pro Leu Tyr Pro Leu Thr Lys Pro Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Asp Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Glu Leu Ile Ala Leu Thr Gln Ala Leu Lys Met Ala Glu Gly
                565                 570                 575
```

```
Lys Lys Leu Asn Val Tyr Thr Asp Ser Arg Tyr Ala Phe Ala Thr Ala
            580                 585                 590

His Ile His Gly Glu Ile Tyr Arg Arg Arg Gly Trp Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro
        675


<210> SEQ ID NO 5
<211> LENGTH: 683
<212> TYPE: PRT
<213> ORGANISM: Artificial sequence
<220> FEATURE:
<223> OTHER INFORMATION: CaMV reverse transcriptase amino acid sequence

<400> SEQUENCE: 5

Met Asp His Leu Leu Leu Lys Thr Gln Thr Gln Thr Glu Gln Val Met
1               5                   10                  15

Asn Val Thr Asn Pro Asn Ser Ile Tyr Ile Lys Gly Arg Leu Tyr Phe
            20                  25                  30

Lys Gly Tyr Lys Lys Ile Glu Leu His Cys Phe Val Asp Thr Gly Ala
        35                  40                  45

Ser Leu Cys Ile Ala Ser Lys Phe Val Ile Pro Glu Glu His Trp Val
    50                  55                  60

Asn Ala Glu Arg Pro Ile Met Val Lys Ile Ala Asp Gly Ser Ser Ile
65                  70                  75                  80

Thr Ile Ser Lys Val Cys Lys Asp Ile Asp Leu Ile Ile Ala Gly Glu
                85                  90                  95

Ile Phe Arg Ile Pro Thr Val Tyr Gln Gln Glu Ser Gly Ile Asp Phe
            100                 105                 110

Ile Ile Gly Asn Asn Phe Cys Gln Leu Tyr Glu Pro Phe Ile Gln Phe
        115                 120                 125

Thr Asp Arg Val Ile Phe Thr Lys Asn Lys Ser Tyr Pro Val His Ile
    130                 135                 140

Ala Lys Leu Thr Arg Ala Val Arg Val Gly Thr Glu Gly Phe Leu Glu
145                 150                 155                 160

Ser Met Lys Lys Arg Ser Lys Thr Gln Gln Pro Glu Pro Val Asn Ile
                165                 170                 175

Ser Thr Asn Lys Ile Glu Asn Pro Leu Glu Glu Ile Ala Ile Leu Ser
            180                 185                 190

Glu Gly Arg Arg Leu Ser Glu Glu Lys Leu Phe Ile Thr Gln Gln Arg
        195                 200                 205

Met Gln Lys Ile Glu Glu Leu Leu Glu Lys Val Cys Ser Glu Asn Pro
    210                 215                 220

Leu Asp Pro Asn Lys Thr Lys Gln Trp Met Lys Ala Ser Ile Lys Leu
225                 230                 235                 240

Ser Asp Pro Ser Lys Ala Ile Lys Val Lys Pro Met Lys Tyr Ser Pro
                245                 250                 255
```

```
Met Asp Arg Glu Glu Phe Asp Lys Gln Ile Lys Glu Leu Leu Asp Leu
            260                 265                 270

Lys Val Ile Lys Pro Ser Lys Ser Pro His Met Ala Pro Ala Phe Leu
        275                 280                 285

Val Asn Asn Glu Ala Glu Lys Arg Arg Gly Lys Lys Arg Met Val Val
    290                 295                 300

Asn Tyr Lys Ala Met Asn Lys Ala Thr Val Gly Asp Ala Tyr Asn Leu
305                 310                 315                 320

Pro Asn Lys Asp Glu Leu Leu Thr Leu Ile Arg Gly Lys Lys Ile Phe
                325                 330                 335

Ser Ser Phe Asp Cys Lys Ser Gly Phe Trp Gln Val Leu Leu Asp Gln
            340                 345                 350

Glu Ser Arg Pro Leu Thr Ala Phe Thr Cys Pro Gln Gly His Tyr Glu
        355                 360                 365

Trp Asn Val Val Pro Phe Gly Leu Lys Gln Ala Pro Ser Ile Phe Gln
    370                 375                 380

Arg His Met Asp Glu Ala Phe Arg Val Phe Arg Lys Phe Cys Cys Val
385                 390                 395                 400

Tyr Val Asp Asp Ile Leu Val Phe Ser Asn Asn Glu Glu Asp His Leu
                405                 410                 415

Leu His Val Ala Met Ile Leu Gln Lys Cys Asn Gln His Gly Ile Ile
            420                 425                 430

Leu Ser Lys Lys Lys Ala Gln Leu Phe Lys Lys Lys Ile Asn Phe Leu
        435                 440                 445

Gly Leu Glu Ile Asp Glu Gly Thr His Lys Pro Gln Gly His Ile Leu
    450                 455                 460

Glu His Ile Asn Lys Phe Pro Asp Thr Leu Glu Asp Lys Lys Gln Leu
465                 470                 475                 480

Gln Arg Phe Leu Gly Ile Leu Thr Tyr Ala Ser Asp Tyr Ile Pro Lys
                485                 490                 495

Leu Ala Gln Ile Arg Lys Pro Leu Gln Ala Lys Leu Lys Glu Asn Val
            500                 505                 510

Pro Trp Arg Trp Thr Lys Glu Asp Thr Leu Tyr Met Gln Lys Val Lys
        515                 520                 525

Lys Asn Leu Gln Gly Phe Pro Pro Leu His His Pro Leu Pro Glu Glu
    530                 535                 540

Lys Leu Ile Ile Glu Thr Asp Ala Ser Asp Asp Tyr Trp Gly Gly Met
545                 550                 555                 560

Leu Lys Ala Ile Lys Ile Asn Glu Gly Thr Asn Thr Glu Leu Ile Cys
                565                 570                 575

Arg Tyr Ala Ser Gly Ser Phe Lys Ala Ala Glu Lys Asn Tyr His Ser
            580                 585                 590

Asn Asp Lys Glu Thr Leu Ala Val Ile Asn Thr Ile Lys Lys Phe Ser
        595                 600                 605

Ile Tyr Leu Thr Pro Val His Phe Leu Ile Arg Thr Asp Asn Thr His
    610                 615                 620

Phe Lys Ser Phe Val Asn Leu Asn Tyr Lys Gly Asp Ser Lys Leu Gly
625                 630                 635                 640

Arg Asn Ile Arg Trp Gln Ala Trp Leu Ser His Tyr Ser Phe Asp Val
                645                 650                 655

Glu His Ile Lys Gly Thr Asp Asn His Phe Ala Asp Phe Leu Ser Arg
            660                 665                 670

Glu Phe Asn Lys Val Asn Ser Ser Gly Gly Ser
```

675 680

<210> SEQ ID NO 6
<211> LENGTH: 329
<212> TYPE: PRT
<213> ORGANISM: Artificial sequence
<220> FEATURE:
<223> OTHER INFORMATION: retron rever transcriptase amino acid sequence

<400> SEQUENCE: 6

Met Gly Ile His Gly Val Pro Ala Ala Met Lys Ser Ala Glu Tyr Leu
1 5 10 15

Asn Thr Phe Arg Leu Arg Asn Leu Gly Leu Pro Val Met Asn Asn Leu
20 25 30

His Asp Met Ser Lys Ala Thr Arg Ile Ser Val Glu Thr Leu Arg Leu
35 40 45

Leu Ile Tyr Thr Ala Asp Phe Arg Tyr Arg Ile Tyr Thr Val Glu Lys
50 55 60

Lys Gly Pro Glu Lys Arg Met Arg Thr Ile Tyr Gln Pro Ser Arg Glu
65 70 75 80

Leu Lys Ala Leu Gln Gly Trp Val Leu Arg Asn Ile Leu Asp Lys Leu
85 90 95

Ser Ser Ser Pro Phe Ser Ile Gly Phe Glu Lys His Gln Ser Ile Leu
100 105 110

Asn Asn Ala Thr Pro His Ile Gly Ala Asn Phe Ile Leu Asn Ile Asp
115 120 125

Leu Glu Asp Phe Phe Pro Ser Leu Thr Ala Asn Lys Val Phe Gly Val
130 135 140

Phe His Ser Leu Gly Tyr Asn Arg Leu Ile Ser Ser Val Leu Thr Lys
145 150 155 160

Ile Cys Cys Tyr Lys Asn Leu Leu Pro Gln Gly Ala Pro Ser Ser Pro
165 170 175

Lys Leu Ala Asn Leu Ile Cys Ser Lys Leu Asp Tyr Arg Ile Gln Gly
180 185 190

Tyr Ala Gly Ser Arg Gly Leu Ile Tyr Thr Arg Tyr Ala Asp Asp Leu
195 200 205

Thr Leu Ser Ala Gln Ser Met Lys Lys Val Val Lys Ala Arg Asp Phe
210 215 220

Leu Phe Ser Ile Ile Pro Ser Glu Gly Leu Val Ile Asn Ser Lys Lys
225 230 235 240

Thr Cys Ile Ser Gly Pro Arg Ser Gln Arg Lys Val Thr Gly Leu Val
245 250 255

Ile Ser Gln Glu Lys Val Gly Ile Gly Arg Glu Lys Tyr Lys Glu Ile
260 265 270

Arg Ala Lys Ile His His Ile Phe Cys Gly Lys Ser Ser Glu Ile Glu
275 280 285

His Val Arg Gly Trp Leu Ser Phe Ile Leu Ser Val Asp Ser Lys Ser
290 295 300

His Arg Arg Leu Ile Thr Tyr Ile Ser Lys Leu Glu Lys Lys Tyr Gly
305 310 315 320

Lys Asn Pro Leu Asn Lys Ala Lys Thr
325

<210> SEQ ID NO 7
<211> LENGTH: 32
<212> TYPE: PRT

<213> ORGANISM: Artificial sequence
<220> FEATURE:
<223> OTHER INFORMATION: 32aa linker amino acid sequence

<400> SEQUENCE: 7

Ser Gly Gly Ser Ser Gly Gly Ser Ser Gly Ser Glu Thr Pro Gly Thr
1 5 10 15

Ser Glu Ser Ala Thr Pro Glu Ser Ser Gly Gly Ser Ser Gly Gly Ser
20 25 30

<210> SEQ ID NO 8
<211> LENGTH: 76
<212> TYPE: RNA
<213> ORGANISM: Artificial sequence
<220> FEATURE:
<223> OTHER INFORMATION: gRNA sccaflod sequence

<400> SEQUENCE: 8
guuuuagagc uagaaauagc aaguuaaaau aaggcuaguc cguuaucaac uugaaaaagu 60
ggcaccgagu cggugc 76

<210> SEQ ID NO 9
<211> LENGTH: 6327
<212> TYPE: DNA
<213> ORGANISM: Artificial sequence
<220> FEATURE:
<223> OTHER INFORMATION: nucleotide sequence of the fusion protein nCas9(H840A)-M-MLV of the invention

<400> SEQUENCE: 9
atgcctaaga aaaagagaaa agtggacaag aagtactcga tcggcctcga tattgggact 60
aactctgttg gctgggccgt gatcaccgac gagtacaagg tgccctcaaa gaagttcaag 120
gtcctgggca acaccgatcg gcattccatc aagaagaatc tcattggcgc tctcctgttc 180
gacagcggcg agacggctga ggctacgcgg ctcaagcgca ccgcccgcag gcggtacacg 240
cgcaggaaga atcgcatctg ctacctgcag gagattttct ccaacgagat ggcgaaggtt 300
gacgattctt tcttccacag gctggaggag tcattcctcg tggaggagga taagaagcac 360
gagcggcatc caatcttcgg caacattgtc gacgaggttg cctaccacga gaagtaccct 420
acgatctacc atctgcggaa gaagctcgtg gactccacag ataaggcgga cctccgcctg 480
atctacctcg ctctggccca catgattaag ttcaggggcc atttcctgat cgagggggat 540
ctcaacccgg acaatagcga tgttgacaag ctgttcatcc agctcgtgca gacgtacaac 600
cagctcttcg aggagaaccc cattaatgcg tcaggcgtcg acgcgaaggc tatcctgtcc 660
gctaggctct cgaagtctcg gcgcctcgag aacctgatcg cccagctgcc gggcgagaag 720
aagaacggcc tgttcgggaa tctcattgcg ctcagcctgg ggctcacgcc caacttcaag 780
tcgaatttcg atctcgctga ggacgccaag ctgcagctct ccaaggacac atacgacgat 840
gacctggata acctcctggc ccagatcggc gatcagtacg cggacctgtt cctcgctgcc 900
aagaatctgt cggacgccat cctcctgtct gatattctca gggtgaacac cgagattacg 960
aaggctccgc tctcagcctc catgatcaag cgctacgacg agcaccatca ggatctgacc 1020
ctcctgaagg cgctggtcag gcagcagctc cccgagaagt acaaggagat cttcttcgat 1080
cagtcgaaga acggctacgc tgggtacatt gacggcgggg cctctcagga ggagttctac 1140
aagttcatca agccgattct ggagaagatg gacggcacgg aggagctgct ggtgaagctc 1200
aatcgcgagg acctcctgag gaagcagcgg acattcgata acggcagcat cccacaccag 1260

```
attcatctcg gggagctgca cgctatcctg aggaggcagg aggacttcta ccctttcctc   1320
aaggataacc gcgagaagat cgagaagatt ctgactttca ggatcccgta ctacgtcggc   1380
ccactcgcta ggggcaactc ccgcttcgct tggatgaccc gcaagtcaga ggagacgatc   1440
acgccgtgga acttcgagga ggtggtcgac aagggcgcta gcgctcagtc gttcatcgag   1500
aggatgacga atttcgacaa gaacctgcca aatgagaagg tgctccctaa gcactcgctc   1560
ctgtacgagt acttcacagt ctacaacgag ctgactaagg tgaagtatgt gaccgagggc   1620
atgaggaagc cggctttcct gtctggggag cagaagaagg ccatcgtgga cctcctgttc   1680
aagaccaacc ggaaggtcac ggttaagcag ctcaaggagg actacttcaa gaagattgag   1740
tgcttcgatt cggtcgagat ctctggcgtt gaggaccgct tcaacgcctc cctggggacc   1800
taccacgatc tcctgaagat cattaaggat aaggacttcc tggacaacga ggagaatgag   1860
gatatcctcg aggacattgt gctgacactc actctgttcg aggaccggga gatgatcgag   1920
gagcgcctga agacttacgc ccatctcttc gatgacaagg tcatgaagca gctcaagagg   1980
aggaggtaca ccggctgggg gaggctgagc aggaagctca tcaacggcat tcgggacaag   2040
cagtccggga agacgatcct cgacttcctg aagagcgatg gcttcgcgaa ccgcaatttc   2100
atgcagctga ttcacgatga cagcctcaca ttcaaggagg atatccagaa ggctcaggtg   2160
agcggccagg gggactcgct gcacgagcat atcgcgaacc tcgctggctc gccagctatc   2220
aagaagggga ttctgcagac cgtgaaggtt gtggacgagc tggtgaaggt catgggcagg   2280
cacaagcctg agaacatcgt cattgagatg gcccgggaga atcagaccac gcagaagggc   2340
cagaagaact cacgcgagag gatgaagagg atcgaggagg gcattaagga gctggggtcc   2400
cagatcctca aggagcaccc ggtggagaac acgcagctgc agaatgagaa gctctacctg   2460
tactacctcc agaatggccg cgatatgtat gtggaccagg agctggatat taacaggctc   2520
agcgattacg acgtcgatgc catcgttcca cagtcattcc tgaaggatga ctccattgac   2580
aacaaggtcc tcaccaggtc ggacaagaac cggggcaagt ctgataatgt tccttcagag   2640
gaggtcgtta agaagatgaa gaactactgg cgccagctcc tgaatgccaa gctgatcacg   2700
cagcggaagt tcgataacct cacaaaggct gagaggggcg ggctctctga gctggacaag   2760
gcgggcttca tcaagaggca gctggtcgag acacggcaga tcactaagca cgttgcgcag   2820
attctcgact cacggatgaa cactaagtac gatgagaatg acaagctgat ccgcgaggtg   2880
aaggtcatca ccctgaagtc aaagctcgtc tccgacttca ggaaggattt ccagttctac   2940
aaggttcggg agatcaacaa ttaccaccat gcccatgacg cgtacctgaa cgcggtggtc   3000
ggcacagctc tgatcaagaa gtacccaaag ctcgagagcg agttcgtgta cggggactac   3060
aaggtttacg atgtgaggaa gatgatcgcc aagtcggagc aggagattgg caaggctacc   3120
gccaagtact tcttctactc taacattatg aatttcttca agacagagat cactctggcc   3180
aatggcgaga tccggaagcg cccccctcatc gagacgaacg gcgagacggg ggagatcgtg   3240
tgggacaagg gcagggattt cgcgaccgtc aggaaggttc tctccatgcc acaagtgaat   3300
atcgtcaaga agacagaggt ccagactggc gggttctcta aggagtcaat tctgcctaag   3360
cggaacagcg acaagctcat cgcccgcaag aaggactggg atccgaagaa gtacggcggg   3420
ttcgacagcc ccactgtggc ctactcggtc ctggttgtgg cgaaggttga gaagggcaag   3480
tccaagaagc tcaagagcgt gaaggagctg ctggggatca cgattatgga gcgctccagc   3540
ttcgagaaga acccgatcga tttcctggag gcgaagggct acaaggaggt gaagaaggac   3600
ctgatcatta agctccccaa gtactcactc ttcgagctgg agaacggcag gaagcggatg   3660
```

ctggcttccg ctggcgagct gcagaagggg aacgagctgg ctctgccgtc caagtatgtg 3720
aacttcctct acctggcctc ccactacgag aagctcaagg gcagccccga ggacaacgag 3780
cagaagcagc tgttcgtcga gcagcacaag cattacctcg acgagatcat tgagcagatt 3840
tccgagttct ccaagcgcgt gatcctggcc gacgcgaatc tggataaggt cctctccgcg 3900
tacaacaagc accgcgacaa gccaatcagg gagcaggctg agaatatcat tcatctcttc 3960
accctgacga acctcggcgc ccctgctgct ttcaagtact tcgacacaac tatcgatcgc 4020
aagaggtaca caagcactaa ggaggtcctg gacgcgaccc tcatccacca gtcgattacc 4080
ggcctctacg agacgcgcat cgacctgtct cagctcgggg gcgacgaatt cccaaagaag 4140
aagcggaagg tggagctcag cggaggatct tccggaggat ctagcggctc cgagacacca 4200
ggaacatccg aaagcgctac accagaatct agcggaggct cttccggagg atctaggcct 4260
accctcaaca tcgaggatga gtatcgcctc cacgaaacct ccaaagaacc ggacgtgtcc 4320
ctcggcagca catggctcag cgacttccca caagcgtggg ccgaaaccgg cggcatgggc 4380
ctcgccgtcc gccaagcccc actcattatc ccgctgaagg cgacctccac accggtgtcc 4440
atcaagcagt acccgatgag ccaagaggcg aggctcggga ttaagccgca cattcagcgc 4500
ctcctcgatc aaggcattct cgtgccgtgc caatccccgt ggaatacacc actcctcccg 4560
gtcaaaaagc cgggcaccaa cgactatcgc ccggtccaag atctccgcga ggtcaacaag 4620
cgcgtggaag acatccaccc gaccgtcccg aacccgtata atctgctctc cgggctccca 4680
ccatcccacc agtggtatac agtgctggac ctcaaagacg ccttcttctg tctccgcctc 4740
cacccaacaa gccagccgct cttcgccttc gagtggcgcg acccggagat gggcatctcc 4800
ggccaactga catggacacg cctcccgcaa ggcttcaaga acagcccgac actcttcaac 4860
gaggcgctcc atagggacct cgcggatttt cgcatccagc atccggacct catcctcctc 4920
cagtatgtgg atgatctcct cctcgccgcg acctccgagc tggattgtca acaaggcaca 4980
cgcgcgctcc tccaaacact cgggaacctc ggctatcgcg cgtccgcgaa aaaggcccaa 5040
atctgccaga agcaagtgaa gtacctcggg tatctgctca aggaaggcca acgctggctc 5100
accgaagcgc gcaaagaaac agtgatgggg caaccgacac cgaaaacacc acgccagctg 5160
cgcgagtttc tcggcaaagc cggcttctgt cgcctcttca tcccgggctt tgccgagatg 5220
gccgcgccac tctacccact caccaagccg ggcacactgt ttaactgggg gccggatcag 5280
cagaaagcct accaagagat caaacaagcg ctcctcaccg ccccagcgct cgggctccca 5340
gatctcacaa agccgttcga gctgttcgtc gatgagaagc aaggctacgc gaagggcgtg 5400
ctcacacaga agctcggccc gtggaggagg ccagtggcct atctctccaa aaaactcgat 5460
ccagtggccg ccggctggcc accgtgtctg cgcatggtcg ccgcgattgc cgtgctcaca 5520
aaggatgccg gcaaactcac aatgggccag ccgctggtga tcctcgcgcc acatgccgtg 5580
gaagccctcg tcaaacagcc gccggatagg tggctctcca atgcgcgcat gacccattac 5640
caagcgctcc tcctcgacac cgatcgcgtc cagttcggcc cagtggtcgc cctcaatccg 5700
gcgacactgc tgccactccc agaggagggc ctccaacaca actgtctgga tattctcgcg 5760
gaagcgcatg gcacaaggcc agacctcaca gatcaaccgc tcccggatgc ggatcacaca 5820
tggtataccg acggctcctc tctgctccaa gagggccaaa ggaaagccgg cgccgcggtg 5880
accacagaaa cagaagtgat ctgggccaag gccctcccag ccggcacatc cgcgcaaagg 5940
gcggaactca tcgcgctcac acaagccctc aagatggccg agggcaagaa gctcaacgtc 6000
tacacagact cccgctatgc cttcgccacc gcccacattc acggcgaaat ctataggagg 6060
cgcggctggc tcacaagcga ggggaaggag atcaagaaca aggatgagat cctcgcgctg 6120
ctcaaggccc tctttctccc gaagcgcctc tccatcatcc actgtccggg ccaccaaaag 6180
gggcactccg cggaagcgag gggcaatagg atggccgatc aagccgcgcg caaagccgcg 6240
attaccgaaa ccccagacac atccaccctc ctcatcgaaa actcctcccc aagcggcggc 6300
agcccgaaga agaaaaggaa ggtgtga 6327

<210> SEQ ID NO 10
<211> LENGTH: 6342
<212> TYPE: DNA
<213> ORGANISM: Artificial sequence
<220> FEATURE:
<223> OTHER INFORMATION: nucleotide sequence of the fusion protein nCas9(H840A)-CaMV of the invention

<400> SEQUENCE: 10
atgcctaaga aaaagagaaa agtggacaag aagtactcga tcggcctcga tattgggact 60
aactctgttg gctgggccgt gatcaccgac gagtacaagg tgccctcaaa gaagttcaag 120
gtcctgggca acaccgatcg gcattccatc aagaagaatc tcattggcgc tctcctgttc 180
gacagcggcg agacggctga ggctacgcgg ctcaagcgca ccgcccgcag gcggtacacg 240
cgcaggaaga atcgcatctg ctacctgcag gagattttct ccaacgagat ggcgaaggtt 300
gacgattctt tcttccacag gctggaggag tcattcctcg tggaggagga taagaagcac 360
gagcggcatc caatcttcgg caacattgtc gacgaggttg cctaccacga gaagtaccct 420
acgatctacc atctgcggaa gaagctcgtg gactccacag ataaggcgga cctccgcctg 480
atctacctcg ctctggccca catgattaag ttcaggggcc atttcctgat cgagggggat 540
ctcaacccgg acaatagcga tgttgacaag ctgttcatcc agctcgtgca gacgtacaac 600
cagctcttcg aggagaaccc cattaatgcg tcaggcgtcg acgcgaaggc tatcctgtcc 660
gctaggctct cgaagtctcg gcgcctcgag aacctgatcg cccagctgcc gggcgagaag 720
aagaacggcc tgttcgggaa tctcattgcg ctcagcctgg ggctcacgcc caacttcaag 780
tcgaatttcg atctcgctga ggacgccaag ctgcagctct ccaaggacac atacgacgat 840
gacctggata acctcctggc ccagatcggc gatcagtacg cggacctgtt cctcgctgcc 900
aagaatctgt cggacgccat cctcctgtct gatattctca gggtgaacac cgagattacg 960
aaggctccgc tctcagcctc catgatcaag cgctacgacg agcaccatca ggatctgacc 1020
ctcctgaagg cgctggtcag gcagcagctc cccgagaagt acaaggagat cttcttcgat 1080
cagtcgaaga acggctacgc tgggtacatt gacggcgggg cctctcagga ggagttctac 1140
aagttcatca agccgattct ggagaagatg gacggcacgg aggagctgct ggtgaagctc 1200
aatcgcgagg acctcctgag gaagcagcgg acattcgata acggcagcat cccacaccag 1260
attcatctcg ggagctgca cgctatcctg aggaggcagg aggacttcta ccctttcctc 1320
aaggataacc gcgagaagat cgagaagatt ctgactttca ggatcccgta ctacgtcggc 1380
ccactcgcta ggggcaactc ccgcttcgct tggatgaccc gcaagtcaga ggagacgatc 1440
acgccgtgga acttcgagga ggtggtcgac aagggcgcta gcgctcagtc gttcatcgag 1500
aggatgacga atttcgacaa gaacctgcca aatgagaagg tgctccctaa gcactcgctc 1560
ctgtacgagt acttcacagt ctacaacgag ctgactaagg tgaagtatgt gaccgagggc 1620
atgaggaagc cggctttcct gtctggggag cagaagaagg ccatcgtgga cctcctgttc 1680
aagaccaacc ggaaggtcac ggttaagcag ctcaaggagg actacttcaa gaagattgag 1740
tgcttcgatt cggtcgagat ctctggcgtt gaggaccgct tcaacgcctc cctggggacc 1800
taccacgatc tcctgaagat cattaaggat aaggacttcc tggacaacga ggagaatgag 1860
gatatcctcg aggacattgt gctgacactc actctgttcg aggaccggga gatgatcgag 1920
gagcgcctga agacttacgc ccatctcttc gatgacaagg tcatgaagca gctcaagagg 1980
aggaggtaca ccggctgggg gaggctgagc aggaagctca tcaacggcat tcgggacaag 2040
cagtccggga agacgatcct cgacttcctg aagagcgatg gcttcgcgaa ccgcaatttc 2100
atgcagctga ttcacgatga cagcctcaca ttcaaggagg atatccagaa ggctcaggtg 2160
agcggccagg gggactcgct gcacgagcat atcgcgaacc tcgctggctc gccagctatc 2220
aagaagggga ttctgcagac cgtgaaggtt gtggacgagc tggtgaaggt catgggcagg 2280
cacaagcctg agaacatcgt cattgagatg gcccgggaga atcagaccac gcagaagggc 2340
cagaagaact cacgcgagag gatgaagagg atcgaggagg gcattaagga gctggggtcc 2400
cagatcctca aggagcaccc ggtggagaac acgcagctgc agaatgagaa gctctacctg 2460
tactacctcc agaatggccg cgatatgtat gtggaccagg agctggatat taacaggctc 2520
agcgattacg acgtcgatgc catcgttcca cagtcattcc tgaaggatga ctccattgac 2580
aacaaggtcc tcaccaggtc ggacaagaac cggggcaagt ctgataatgt tccttcagag 2640
gaggtcgtta agaagatgaa gaactactgg cgccagctcc tgaatgccaa gctgatcacg 2700
cagcggaagt tcgataacct cacaaaggct gagaggggcg ggctctctga gctggacaag 2760
gcgggcttca tcaagaggca gctggtcgag acacggcaga tcactaagca cgttgcgcag 2820
attctcgact cacggatgaa cactaagtac gatgagaatg acaagctgat ccgcgaggtg 2880
aaggtcatca ccctgaagtc aaagctcgtc tccgacttca ggaaggattt ccagttctac 2940
aaggttcggg agatcaacaa ttaccaccat gcccatgacg cgtacctgaa cgcggtggtc 3000
ggcacagctc tgatcaagaa gtacccaaag ctcgagagcg agttcgtgta cggggactac 3060
aaggtttacg atgtgaggaa gatgatcgcc aagtcggagc aggagattgg caaggctacc 3120
gccaagtact tcttctactc taacattatg aatttcttca agacagagat cactctggcc 3180
aatggcgaga tccggaagcg cccccctcatc gagacgaacg gcgagacggg ggagatcgtg 3240
tgggacaagg gcagggattt cgcgaccgtc aggaaggttc tctccatgcc acaagtgaat 3300
atcgtcaaga agacagaggt ccagactggc gggttctcta aggagtcaat tctgcctaag 3360
cggaacagcg acaagctcat cgcccgcaag aaggactggg atccgaagaa gtacggcggg 3420
ttcgacagcc ccactgtggc ctactcggtc ctggttgtgg cgaaggttga gaagggcaag 3480
tccaagaagc tcaagagcgt gaaggagctg ctggggatca cgattatgga gcgctccagc 3540
ttcgagaaga acccgatcga tttcctggag gcgaagggct acaaggaggt gaagaaggac 3600
ctgatcatta agctccccaa gtactcactc ttcgagctgg agaacggcag gaagcggatg 3660
ctggcttccg ctggcgagct gcagaagggg aacgagctgg ctctgccgtc caagtatgtg 3720
aacttcctct acctggcctc ccactacgag aagctcaagg gcagccccga ggacaacgag 3780
cagaagcagc tgttcgtcga gcagcacaag cattacctcg acgagatcat tgagcagatt 3840
tccgagttct ccaagcgcgt gatcctggcc gacgcgaatc tggataaggt cctctccgcg 3900
tacaacaagc accgcgacaa gccaatcagg gagcaggctg agaatatcat tcatctcttc 3960
accctgacga acctcggcgc ccctgctgct ttcaagtact tcgacacaac tatcgatcgc 4020
aagaggtaca caagcactaa ggaggtcctg gacgcgaccc tcatccacca gtcgattacc 4080

```
ggcctctacg agacgcgcat cgacctgtct cagctcgggg gcgacgaatt cccaaagaag   4140
aagcggaagg tggagctcag cggaggatct tccggaggat ctagcggctc cgagacacca   4200
ggaacatccg aaagcgctac accagaatct agcggaggct cttccggagg atctaggcct   4260
gatcatctgc tcctcaagac acagacccag accgagcaag tgatgaatgt gaccaacccg   4320
aactccatct acatcaaggg gcgcctctat ttcaagggct ataagaagat cgaactccat   4380
tgctttgtcg acaccggcgc gtccctctgc atcgcgagca agttcgtcat cccagaagag   4440
cattgggtga acgcggagag gccgatcatg gtgaagatcg ccgacggctc ctccatcacc   4500
atcagcaagg tgtgcaagga tatcgatctc atcatcgccg gcgagatctt ccgcattcca   4560
accgtctacc agcaagagtc cggcatcgac tttattatcg gcaacaactt ctgccagctg   4620
tacgaaccgt tcatccagtt caccgaccgc gtgatcttca caaagaacaa gtcctacccg   4680
gtccacatcg ccaaactgac aagggcggtg agggtgggga cagagggctt tctcgagagc   4740
atgaagaaga ggagcaagac acagcagcca gagccggtga atatcagcac caacaagatc   4800
gaaaacccgc tggaggagat tgccattctc agcgaggggga ggaggctctc cgaggagaag   4860
ctctttatta cccagcagcg catgcagaag atcgaagaac tgctcgagaa agtctgctcc   4920
gagaacccac tcgacccgaa taagaccaag cagtggatga aggcgagcat caaactctcc   4980
gatccgagca aagcgatcaa agtgaagccg atgaagtact ccccgatgga tcgcgaggag   5040
ttcgacaagc agattaagga gctgctggac ctcaaagtca tcaagccgtc caaatccccg   5100
cacatggccc cagcctttct cgtgaataat gaggcggaga agaggagggg caagaagagg   5160
atggtcgtga actacaaggc gatgaacaaa gcgaccgtgg gggatgcgta taatctgccg   5220
aacaaggacg agctgctcac actgattcgc ggcaagaaga tcttctccag cttcgattgc   5280
aagtccgggt tctggcaagt gctcctcgac caagaatctc gcccactcac cgcctttaca   5340
tgcccgcaag gccactacga gtggaacgtc gtgccattcg ggctcaagca agccccaagc   5400
atcttccagc gccacatgga tgaagccttc cgcgtgttcc gcaaattctg ctgcgtctac   5460
gtcgatgaca tcctcgtgtt ttccaacaac gaggaggacc acctcctcca tgtggccatg   5520
attctccaga agtgcaatca gcacggcatc attctctcca agaagaaagc gcagctgttc   5580
aagaaaaaaa tcaactttct cggcctcgag attgatgagg gcacccataa gccgcaaggc   5640
catattctcg agcacatcaa caagtttccg gacaccctcg aggacaagaa gcaactgcaa   5700
cgctttctcg gcatcctcac atacgcgagc gactatatcc caaaactcgc ccagatccgc   5760
aagccactcc aagccaaact gaaggaaaac gtcccgtggc gctggaccaa agaggacacc   5820
ctctacatgc agaaagtgaa gaaaaatctc caaggctttc cgccgctgca ccatccactc   5880
ccggaggaaa agctcatcat tgaaaccgac gcgagcgatg attactgggg cgggatgctc   5940
aaggccatca agattaacga gggcaccaac accgaactca tctgtcgcta cgcgtccggg   6000
tcctttaagg cggccgagaa gaactaccac agcaacgata aggaaaccct cgcggtcatc   6060
aacaccatca aaaagttcag catctatctc accccggtgc actttctcat ccgcaccgac   6120
aacacacact ttaagagctt cgtcaacctc aactataagg gcgattccaa gctcgggcgc   6180
aacattaggt ggcaagcgtg gctctcccac tacagctttg acgtcgagca catcaagggc   6240
accgacaacc atttcgccga ctttctcagc cgcgagttca acaaggtcaa ttccagcggg   6300
ggcagcagcg gcggcagccc gaagaagaaa aggaaggtgt ga                       6342
```

<210> SEQ ID NO 11

<211> LENGTH: 5280
<212> TYPE: DNA
<213> ORGANISM: Artificial sequence
<220> FEATURE:
<223> OTHER INFORMATION: nucleotide sequence of the fusion protein nCas9(H840A)-retron of the invention

<400> SEQUENCE: 11

```
atgcctaaga aaaagagaaa agtggacaag aagtactcga tcggcctcga tattgggact      60

aactctgttg gctgggccgt gatcaccgac gagtacaagg tgccctcaaa gaagttcaag     120

gtcctgggca acaccgatcg gcattccatc aagaagaatc tcattggcgc tctcctgttc     180

gacagcggcg agacggctga ggctacgcgg ctcaagcgca ccgcccgcag gcggtacacg     240

cgcaggaaga atcgcatctg ctacctgcag gagattttct ccaacgagat ggcgaaggtt     300

gacgattctt tcttccacag gctggaggag tcattcctcg tggaggagga taagaagcac     360

gagcggcatc caatcttcgg caacattgtc gacgaggttg cctaccacga gaagtaccct     420

acgatctacc atctgcggaa gaagctcgtg gactccacag ataaggcgga cctccgcctg     480

atctacctcg ctctggccca catgattaag ttcaggggcc atttcctgat cgagggggat     540

ctcaacccgg acaatagcga tgttgacaag ctgttcatcc agctcgtgca gacgtacaac     600

cagctcttcg aggagaaccc cattaatgcg tcaggcgtcg acgcgaaggc tatcctgtcc     660

gctaggctct cgaagtctcg gcgcctcgag aacctgatcg cccagctgcc gggcgagaag     720

aagaacggcc tgttcgggaa tctcattgcg ctcagcctgg ggctcacgcc caacttcaag     780

tcgaatttcg atctcgctga ggacgccaag ctgcagctct ccaaggacac atacgacgat     840

gacctggata acctcctggc ccagatcggc gatcagtacg cggacctgtt cctcgctgcc     900

aagaatctgt cggacgccat cctcctgtct gatattctca gggtgaacac cgagattacg     960

aaggctccgc tctcagcctc catgatcaag cgctacgacg agcaccatca ggatctgacc    1020

ctcctgaagg cgctggtcag gcagcagctc cccgagaagt acaaggagat cttcttcgat    1080

cagtcgaaga acggctacgc tgggtacatt gacggcgggg cctctcagga ggagttctac    1140

aagttcatca agccgattct ggagaagatg gacggcacgg aggagctgct ggtgaagctc    1200

aatcgcgagg acctcctgag gaagcagcgg acattcgata acggcagcat cccacaccag    1260

attcatctcg gggagctgca cgctatcctg aggaggcagg aggacttcta ccctttcctc    1320

aaggataacc gcgagaagat cgagaagatt ctgactttca ggatcccgta ctacgtcggc    1380

ccactcgcta ggggcaactc ccgcttcgct tggatgaccc gcaagtcaga ggagacgatc    1440

acgccgtgga acttcgagga ggtggtcgac aagggcgcta gcgctcagtc gttcatcgag    1500

aggatgacga atttcgacaa gaacctgcca aatgagaagg tgctccctaa gcactcgctc    1560

ctgtacgagt acttcacagt ctacaacgag ctgactaagg tgaagtatgt gaccgagggc    1620

atgaggaagc cggctttcct gtctggggag cagaagaagg ccatcgtgga cctcctgttc    1680

aagaccaacc ggaaggtcac ggttaagcag ctcaaggagg actacttcaa gaagattgag    1740

tgcttcgatt cggtcgagat ctctggcgtt gaggaccgct tcaacgcctc cctggggacc    1800

taccacgatc tcctgaagat cattaaggat aaggacttcc tggacaacga ggagaatgag    1860

gatatcctcg aggacattgt gctgacactc actctgttcg aggaccggga gatgatcgag    1920

gagcgcctga agacttacgc ccatctcttc gatgacaagg tcatgaagca gctcaagagg    1980

aggaggtaca ccggctgggg gaggctgagc aggaagctca tcaacggcat tcgggacaag    2040

cagtccggga agacgatcct cgacttcctg aagagcgatg gcttcgcgaa ccgcaatttc    2100
```

atgcagctga ttcacgatga cagcctcaca ttcaaggagg atatccagaa ggctcaggtg 2160
agcggccagg gggactcgct gcacgagcat atcgcgaacc tcgctggctc gccagctatc 2220
aagaagggga ttctgcagac cgtgaaggtt gtggacgagc tggtgaaggt catgggcagg 2280
cacaagcctg agaacatcgt cattgagatg gcccgggaga atcagaccac gcagaagggc 2340
cagaagaact cacgcgagag gatgaagagg atcgaggagg gcattaagga gctggggtcc 2400
cagatcctca aggagcaccc ggtggagaac acgcagctgc agaatgagaa gctctacctg 2460
tactacctcc agaatggccg cgatatgtat gtggaccagg agctggatat taacaggctc 2520
agcgattacg acgtcgatgc catcgttcca cagtcattcc tgaaggatga ctccattgac 2580
aacaaggtcc tcaccaggtc ggacaagaac cggggcaagt ctgataatgt tccttcagag 2640
gaggtcgtta agaagatgaa gaactactgg cgccagctcc tgaatgccaa gctgatcacg 2700
cagcggaagt tcgataacct cacaaaggct gagagggggg ggctctctga gctggacaag 2760
gcgggcttca tcaagaggca gctggtcgag acacggcaga tcactaagca cgttgcgcag 2820
attctcgact cacggatgaa cactaagtac gatgagaatg acaagctgat ccgcgaggtg 2880
aaggtcatca ccctgaagtc aaagctcgtc tccgacttca ggaaggattt ccagttctac 2940
aaggttcggg agatcaacaa ttaccaccat gcccatgacg cgtacctgaa cgcggtggtc 3000
ggcacagctc tgatcaagaa gtacccaaag ctcgagagcg agttcgtgta cggggactac 3060
aaggtttacg atgtgaggaa gatgatcgcc aagtcggagc aggagattgg caaggctacc 3120
gccaagtact tcttctactc taacattatg aatttcttca agacagagat cactctggcc 3180
aatggcgaga tccggaagcg cccccctcatc gagacgaacg gcgagacggg ggagatcgtg 3240
tgggacaagg gcagggattt cgcgaccgtc aggaaggttc tctccatgcc acaagtgaat 3300
atcgtcaaga agacagaggt ccagactggc gggttctcta aggagtcaat tctgcctaag 3360
cggaacagcg acaagctcat cgcccgcaag aaggactggg atccgaagaa gtacggcggg 3420
ttcgacagcc ccactgtggc ctactcggtc ctggttgtgg cgaaggttga gaagggcaag 3480
tccaagaagc tcaagagcgt gaaggagctg ctggggatca cgattatgga gcgctccagc 3540
ttcgagaaga acccgatcga tttcctggag gcgaagggct acaaggaggt gaagaaggac 3600
ctgatcatta agctccccaa gtactcactc ttcgagctgg agaacggcag gaagcggatg 3660
ctggcttccg ctggcgagct gcagaagggg aacgagctgg ctctgccgtc caagtatgtg 3720
aacttcctct acctggcctc ccactacgag aagctcaagg gcagccccga ggacaacgag 3780
cagaagcagc tgttcgtcga gcagcacaag cattacctcg acgagatcat tgagcagatt 3840
tccgagttct ccaagcgcgt gatcctggcc gacgcgaatc tggataaggt cctctccgcg 3900
tacaacaagc accgcgacaa gccaatcagg gagcaggctg agaatatcat tcatctcttc 3960
accctgacga acctcggcgc ccctgctgct ttcaagtact tcgacacaac tatcgatcgc 4020
aagaggtaca caagcactaa ggaggtcctg gacgcgaccc tcatccacca gtcgattacc 4080
ggcctctacg agacgcgcat cgacctgtct cagctcgggg gcgacgaatt cccaaagaag 4140
aagcggaagg tggagctcag cggaggatct tccggaggat ctagcggctc cgagacacca 4200
ggaacatccg aaagcgctac accagaatct agcggaggct cttccggagg atctaggcct 4260
ggtattcacg gcgttcctgc ggcgatgaag tcggctgagt acctgaacac cttccggctg 4320
agaaacctcg ggctgccagt gatgaacaac ctccacgata tgtctaaggc tacccggatc 4380
tccgttgaga cgctgagact cctgatctac accgctgact tccggtacag aatctacacg 4440
gtggagaaga aggggcccga gaagaggatg cgcaccatct accaacctag cagagagctc 4500
aaggcgctgc agggctgggt gctgagaaac atcctcgata agctgtccag ctcgcccttc 4560
tctatcgggt tcgagaagca ccaatccatc ctcaacaacg ccaccccctca tatcggcgcg 4620 aacttcatcc tcaacatcga cctggaggat ttcttcccca gcctcacggc caacaaggtt 4680
ttcggggtgt tccactcgct cggctacaac aggctgatct catctgtcct caccaagatc 4740
tgctgctaca agaacctcct gcctcaaggc gctccatcca gcccgaagct cgccaacctg 4800
atctgctcaa agctggacta ccgcatccag ggctacgctg ggtccagggg cctcatctac 4860
acccgctacg cggacgatct cacgctgagc gctcagtcga tgaagaaggt ggtcaaggcg 4920
cgggatttcc tgttctcaat catcccatct gagggcctcg tcatcaacag caagaagacc 4980
tgcatctccg ggccgcggag ccaaagaaag gtcacgggcc tggttatctc ccaggagaag 5040
gttggcatcg ggagggagaa gtacaaggag atccgcgcca agatccacca tatcttctgc 5100
gggaagtcgt cagagatcga gcacgtgcgc ggctggctct cgttcatcct gtcagtcgac 5160
tctaagtccc ataggcgcct catcacctac atctctaagc tggagaagaa gtacggcaag 5220
aaccccctga acaaggctaa gaccagcggc ggcagcccga agaagaaaag gaaggtgtga 5280

<210> SEQ ID NO 12
<211> LENGTH: 2108
<212> TYPE: PRT
<213> ORGANISM: Artificial sequence
<220> FEATURE:
<223> OTHER INFORMATION: amino acid sequence of the fusion protein nCas9(H840A)-M-MLV of the invention

<400> SEQUENCE: 12

Met Pro Lys Lys Lys Arg Lys Val Asp Lys Lys Tyr Ser Ile Gly Leu
1 5 10 15

Asp Ile Gly Thr Asn Ser Val Gly Trp Ala Val Ile Thr Asp Glu Tyr
20 25 30

Lys Val Pro Ser Lys Lys Phe Lys Val Leu Gly Asn Thr Asp Arg His
35 40 45

Ser Ile Lys Lys Asn Leu Ile Gly Ala Leu Leu Phe Asp Ser Gly Glu
50 55 60

Thr Ala Glu Ala Thr Arg Leu Lys Arg Thr Ala Arg Arg Arg Tyr Thr
65 70 75 80

Arg Arg Lys Asn Arg Ile Cys Tyr Leu Gln Glu Ile Phe Ser Asn Glu
85 90 95

Met Ala Lys Val Asp Asp Ser Phe Phe His Arg Leu Glu Glu Ser Phe
100 105 110

Leu Val Glu Glu Asp Lys Lys His Glu Arg His Pro Ile Phe Gly Asn
115 120 125

Ile Val Asp Glu Val Ala Tyr His Glu Lys Tyr Pro Thr Ile Tyr His
130 135 140

Leu Arg Lys Lys Leu Val Asp Ser Thr Asp Lys Ala Asp Leu Arg Leu
145 150 155 160

Ile Tyr Leu Ala Leu Ala His Met Ile Lys Phe Arg Gly His Phe Leu
165 170 175

Ile Glu Gly Asp Leu Asn Pro Asp Asn Ser Asp Val Asp Lys Leu Phe
180 185 190

Ile Gln Leu Val Gln Thr Tyr Asn Gln Leu Phe Glu Glu Asn Pro Ile
195 200 205

Asn Ala Ser Gly Val Asp Ala Lys Ala Ile Leu Ser Ala Arg Leu Ser
210 215 220

-continued

```
Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
    530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
        595                 600                 605

Lys Asp Lys Asp Phe Leu Asp Asn Glu Glu Asn Glu Asp Ile Leu Glu
    610                 615                 620

Asp Ile Val Leu Thr Leu Thr Leu Phe Glu Asp Arg Glu Met Ile Glu
625                 630                 635                 640
```

-continued

```
Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
        675                 680                 685

Phe Leu Lys Ser Asp Gly Phe Ala Asn Arg Asn Phe Met Gln Leu Ile
    690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
        755                 760                 765

Glu Met Ala Arg Glu Asn Gln Thr Thr Gln Lys Gly Gln Lys Asn Ser
    770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp Ala Ile
        835                 840                 845

Val Pro Gln Ser Phe Leu Lys Asp Asp Ser Ile Asp Asn Lys Val Leu
    850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
        915                 920                 925

Val Glu Thr Arg Gln Ile Thr Lys His Val Ala Gln Ile Leu Asp Ser
    930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val  Gly Thr Ala Leu Ile  Lys Lys Tyr
        995                 1000                1005

Pro Lys  Leu Glu Ser Glu Phe  Val Tyr Gly Asp Tyr  Lys Val Tyr
    1010                1015                1020

Asp Val  Arg Lys Met Ile Ala  Lys Ser Glu Gln Glu  Ile Gly Lys
    1025                1030                1035

Ala Thr  Ala Lys Tyr Phe Phe  Tyr Ser Asn Ile Met  Asn Phe Phe
    1040                1045                1050

Lys Thr  Glu Ile Thr Leu Ala  Asn Gly Glu Ile Arg  Lys Arg Pro
```

```
    1055                1060                1065

Leu Ile  Glu Thr Asn Gly Glu  Thr Gly Glu Ile Val  Trp Asp Lys
    1070                1075                1080

Gly Arg  Asp Phe Ala Thr Val  Arg Lys Val Leu Ser  Met Pro Gln
    1085                1090                1095

Val Asn  Ile Val Lys Lys Thr  Glu Val Gln Thr Gly  Gly Phe Ser
    1100                1105                1110

Lys Glu  Ser Ile Leu Pro Lys  Arg Asn Ser Asp Lys  Leu Ile Ala
    1115                1120                1125

Arg Lys  Lys Asp Trp Asp Pro  Lys Lys Tyr Gly Gly  Phe Asp Ser
    1130                1135                1140

Pro Thr  Val Ala Tyr Ser Val  Leu Val Val Ala Lys  Val Glu Lys
    1145                1150                1155

Gly Lys  Ser Lys Lys Leu Lys  Ser Val Lys Glu Leu  Leu Gly Ile
    1160                1165                1170

Thr Ile  Met Glu Arg Ser Ser  Phe Glu Lys Asn Pro  Ile Asp Phe
    1175                1180                1185

Leu Glu  Ala Lys Gly Tyr Lys  Glu Val Lys Lys Asp  Leu Ile Ile
    1190                1195                1200

Lys Leu  Pro Lys Tyr Ser Leu  Phe Glu Leu Glu Asn  Gly Arg Lys
    1205                1210                1215

Arg Met  Leu Ala Ser Ala Gly  Glu Leu Gln Lys Gly  Asn Glu Leu
    1220                1225                1230

Ala Leu  Pro Ser Lys Tyr Val  Asn Phe Leu Tyr Leu  Ala Ser His
    1235                1240                1245

Tyr Glu  Lys Leu Lys Gly Ser  Pro Glu Asp Asn Glu  Gln Lys Gln
    1250                1255                1260

Leu Phe  Val Glu Gln His Lys  His Tyr Leu Asp Glu  Ile Ile Glu
    1265                1270                1275

Gln Ile  Ser Glu Phe Ser Lys  Arg Val Ile Leu Ala  Asp Ala Asn
    1280                1285                1290

Leu Asp  Lys Val Leu Ser Ala  Tyr Asn Lys His Arg  Asp Lys Pro
    1295                1300                1305

Ile Arg  Glu Gln Ala Glu Asn  Ile Ile His Leu Phe  Thr Leu Thr
    1310                1315                1320

Asn Leu  Gly Ala Pro Ala Ala  Phe Lys Tyr Phe Asp  Thr Thr Ile
    1325                1330                1335

Asp Arg  Lys Arg Tyr Thr Ser  Thr Lys Glu Val Leu  Asp Ala Thr
    1340                1345                1350

Leu Ile  His Gln Ser Ile Thr  Gly Leu Tyr Glu Thr  Arg Ile Asp
    1355                1360                1365

Leu Ser  Gln Leu Gly Gly Asp  Glu Phe Pro Lys Lys  Lys Arg Lys
    1370                1375                1380

Val Glu  Leu Ser Gly Gly Ser  Ser Gly Gly Ser Ser  Gly Ser Glu
    1385                1390                1395

Thr Pro  Gly Thr Ser Glu Ser  Ala Thr Pro Glu Ser  Ser Gly Gly
    1400                1405                1410

Ser Ser  Gly Gly Ser Arg Pro  Thr Leu Asn Ile Glu  Asp Glu Tyr
    1415                1420                1425

Arg Leu  His Glu Thr Ser Lys  Glu Pro Asp Val Ser  Leu Gly Ser
    1430                1435                1440

Thr Trp  Leu Ser Asp Phe Pro  Gln Ala Trp Ala Glu  Thr Gly Gly
    1445                1450                1455
```

```
Met Gly Leu Ala Val Arg Gln Ala Pro Leu Ile Ile Pro Leu Lys
    1460                1465                1470

Ala Thr Ser Thr Pro Val Ser Ile Lys Gln Tyr Pro Met Ser Gln
    1475                1480                1485

Glu Ala Arg Leu Gly Ile Lys Pro His Ile Gln Arg Leu Leu Asp
    1490                1495                1500

Gln Gly Ile Leu Val Pro Cys Gln Ser Pro Trp Asn Thr Pro Leu
    1505                1510                1515

Leu Pro Val Lys Lys Pro Gly Thr Asn Asp Tyr Arg Pro Val Gln
    1520                1525                1530

Asp Leu Arg Glu Val Asn Lys Arg Val Glu Asp Ile His Pro Thr
    1535                1540                1545

Val Pro Asn Pro Tyr Asn Leu Leu Ser Gly Leu Pro Pro Ser His
    1550                1555                1560

Gln Trp Tyr Thr Val Leu Asp Leu Lys Asp Ala Phe Phe Cys Leu
    1565                1570                1575

Arg Leu His Pro Thr Ser Gln Pro Leu Phe Ala Phe Glu Trp Arg
    1580                1585                1590

Asp Pro Glu Met Gly Ile Ser Gly Gln Leu Thr Trp Thr Arg Leu
    1595                1600                1605

Pro Gln Gly Phe Lys Asn Ser Pro Thr Leu Phe Asn Glu Ala Leu
    1610                1615                1620

His Arg Asp Leu Ala Asp Phe Arg Ile Gln His Pro Asp Leu Ile
    1625                1630                1635

Leu Leu Gln Tyr Val Asp Asp Leu Leu Leu Ala Ala Thr Ser Glu
    1640                1645                1650

Leu Asp Cys Gln Gln Gly Thr Arg Ala Leu Leu Gln Thr Leu Gly
    1655                1660                1665

Asn Leu Gly Tyr Arg Ala Ser Ala Lys Lys Ala Gln Ile Cys Gln
    1670                1675                1680

Lys Gln Val Lys Tyr Leu Gly Tyr Leu Leu Lys Glu Gly Gln Arg
    1685                1690                1695

Trp Leu Thr Glu Ala Arg Lys Glu Thr Val Met Gly Gln Pro Thr
    1700                1705                1710

Pro Lys Thr Pro Arg Gln Leu Arg Glu Phe Leu Gly Lys Ala Gly
    1715                1720                1725

Phe Cys Arg Leu Phe Ile Pro Gly Phe Ala Glu Met Ala Ala Pro
    1730                1735                1740

Leu Tyr Pro Leu Thr Lys Pro Gly Thr Leu Phe Asn Trp Gly Pro
    1745                1750                1755

Asp Gln Gln Lys Ala Tyr Gln Glu Ile Lys Gln Ala Leu Leu Thr
    1760                1765                1770

Ala Pro Ala Leu Gly Leu Pro Asp Leu Thr Lys Pro Phe Glu Leu
    1775                1780                1785

Phe Val Asp Glu Lys Gln Gly Tyr Ala Lys Gly Val Leu Thr Gln
    1790                1795                1800

Lys Leu Gly Pro Trp Arg Arg Pro Val Ala Tyr Leu Ser Lys Lys
    1805                1810                1815

Leu Asp Pro Val Ala Ala Gly Trp Pro Pro Cys Leu Arg Met Val
    1820                1825                1830

Ala Ala Ile Ala Val Leu Thr Lys Asp Ala Gly Lys Leu Thr Met
    1835                1840                1845
```

Gly Gln Pro Leu Val Ile Leu Ala Pro His Ala Val Glu Ala Leu
1850 1855 1860

Val Lys Gln Pro Pro Asp Arg Trp Leu Ser Asn Ala Arg Met Thr
1865 1870 1875

His Tyr Gln Ala Leu Leu Leu Asp Thr Asp Arg Val Gln Phe Gly
1880 1885 1890

Pro Val Val Ala Leu Asn Pro Ala Thr Leu Leu Pro Leu Pro Glu
1895 1900 1905

Glu Gly Leu Gln His Asn Cys Leu Asp Ile Leu Ala Glu Ala His
1910 1915 1920

Gly Thr Arg Pro Asp Leu Thr Asp Gln Pro Leu Pro Asp Ala Asp
1925 1930 1935

His Thr Trp Tyr Thr Asp Gly Ser Ser Leu Leu Gln Glu Gly Gln
1940 1945 1950

Arg Lys Ala Gly Ala Ala Val Thr Thr Glu Thr Glu Val Ile Trp
1955 1960 1965

Ala Lys Ala Leu Pro Ala Gly Thr Ser Ala Gln Arg Ala Glu Leu
1970 1975 1980

Ile Ala Leu Thr Gln Ala Leu Lys Met Ala Glu Gly Lys Lys Leu
1985 1990 1995

Asn Val Tyr Thr Asp Ser Arg Tyr Ala Phe Ala Thr Ala His Ile
2000 2005 2010

His Gly Glu Ile Tyr Arg Arg Arg Gly Trp Leu Thr Ser Glu Gly
2015 2020 2025

Lys Glu Ile Lys Asn Lys Asp Glu Ile Leu Ala Leu Leu Lys Ala
2030 2035 2040

Leu Phe Leu Pro Lys Arg Leu Ser Ile Ile His Cys Pro Gly His
2045 2050 2055

Gln Lys Gly His Ser Ala Glu Ala Arg Gly Asn Arg Met Ala Asp
2060 2065 2070

Gln Ala Ala Arg Lys Ala Ala Ile Thr Glu Thr Pro Asp Thr Ser
2075 2080 2085

Thr Leu Leu Ile Glu Asn Ser Ser Pro Ser Gly Gly Ser Pro Lys
2090 2095 2100

Lys Lys Arg Lys Val
2105

<210> SEQ ID NO 13
<211> LENGTH: 2113
<212> TYPE: PRT
<213> ORGANISM: Artificial sequence
<220> FEATURE:
<223> OTHER INFORMATION: amino acid sequence of the fusion protein nCas9(H840A)-CaMV of the invention

<400> SEQUENCE: 13

Met Pro Lys Lys Lys Arg Lys Val Asp Lys Lys Tyr Ser Ile Gly Leu
1 5 10 15

Asp Ile Gly Thr Asn Ser Val Gly Trp Ala Val Ile Thr Asp Glu Tyr
20 25 30

Lys Val Pro Ser Lys Lys Phe Lys Val Leu Gly Asn Thr Asp Arg His
35 40 45

Ser Ile Lys Lys Asn Leu Ile Gly Ala Leu Leu Phe Asp Ser Gly Glu
50 55 60

Thr Ala Glu Ala Thr Arg Leu Lys Arg Thr Ala Arg Arg Arg Tyr Thr
65 70 75 80

```
Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495
```

-continued

```
Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
    530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
        595                 600                 605

Lys Asp Lys Asp Phe Leu Asp Asn Glu Glu Asn Glu Asp Ile Leu Glu
    610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
        675                 680                 685

Phe Leu Lys Ser Asp Gly Phe Ala Asn Arg Asn Phe Met Gln Leu Ile
    690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
        755                 760                 765

Glu Met Ala Arg Glu Asn Gln Thr Thr Gln Lys Gly Gln Lys Asn Ser
    770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp Ala Ile
        835                 840                 845

Val Pro Gln Ser Phe Leu Lys Asp Asp Ser Ile Asp Asn Lys Val Leu
    850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
```

```
        915                 920                 925

Val Glu Thr Arg Gln Ile Thr Lys His Val Ala Gln Ile Leu Asp Ser
    930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val  Gly Thr Ala Leu Ile  Lys Lys Tyr
        995                 1000                1005

Pro Lys  Leu Glu Ser Glu Phe  Val Tyr Gly Asp Tyr  Lys Val Tyr
    1010                1015                1020

Asp Val  Arg Lys Met Ile Ala  Lys Ser Glu Gln Glu  Ile Gly Lys
    1025                1030                1035

Ala Thr  Ala Lys Tyr Phe Phe  Tyr Ser Asn Ile Met  Asn Phe Phe
    1040                1045                1050

Lys Thr  Glu Ile Thr Leu Ala  Asn Gly Glu Ile Arg  Lys Arg Pro
    1055                1060                1065

Leu Ile  Glu Thr Asn Gly Glu  Thr Gly Glu Ile Val  Trp Asp Lys
    1070                1075                1080

Gly Arg  Asp Phe Ala Thr Val  Arg Lys Val Leu Ser  Met Pro Gln
    1085                1090                1095

Val Asn  Ile Val Lys Lys Thr  Glu Val Gln Thr Gly  Gly Phe Ser
    1100                1105                1110

Lys Glu  Ser Ile Leu Pro Lys  Arg Asn Ser Asp Lys  Leu Ile Ala
    1115                1120                1125

Arg Lys  Lys Asp Trp Asp Pro  Lys Lys Tyr Gly Gly  Phe Asp Ser
    1130                1135                1140

Pro Thr  Val Ala Tyr Ser Val  Leu Val Val Ala Lys  Val Glu Lys
    1145                1150                1155

Gly Lys  Ser Lys Lys Leu Lys  Ser Val Lys Glu Leu  Leu Gly Ile
    1160                1165                1170

Thr Ile  Met Glu Arg Ser Ser  Phe Glu Lys Asn Pro  Ile Asp Phe
    1175                1180                1185

Leu Glu  Ala Lys Gly Tyr Lys  Glu Val Lys Lys Asp  Leu Ile Ile
    1190                1195                1200

Lys Leu  Pro Lys Tyr Ser Leu  Phe Glu Leu Glu Asn  Gly Arg Lys
    1205                1210                1215

Arg Met  Leu Ala Ser Ala Gly  Glu Leu Gln Lys Gly  Asn Glu Leu
    1220                1225                1230

Ala Leu  Pro Ser Lys Tyr Val  Asn Phe Leu Tyr Leu  Ala Ser His
    1235                1240                1245

Tyr Glu  Lys Leu Lys Gly Ser  Pro Glu Asp Asn Glu  Gln Lys Gln
    1250                1255                1260

Leu Phe  Val Glu Gln His Lys  His Tyr Leu Asp Glu  Ile Ile Glu
    1265                1270                1275

Gln Ile  Ser Glu Phe Ser Lys  Arg Val Ile Leu Ala  Asp Ala Asn
    1280                1285                1290

Leu Asp  Lys Val Leu Ser Ala  Tyr Asn Lys His Arg  Asp Lys Pro
    1295                1300                1305

Ile Arg  Glu Gln Ala Glu Asn  Ile Ile His Leu Phe  Thr Leu Thr
    1310                1315                1320
```

```
Asn Leu Gly Ala Pro Ala Ala Phe Lys Tyr Phe Asp Thr Thr Ile
    1325                1330                1335

Asp Arg Lys Arg Tyr Thr Ser Thr Lys Glu Val Leu Asp Ala Thr
    1340                1345                1350

Leu Ile His Gln Ser Ile Thr Gly Leu Tyr Glu Thr Arg Ile Asp
    1355                1360                1365

Leu Ser Gln Leu Gly Gly Asp Glu Phe Pro Lys Lys Lys Arg Lys
    1370                1375                1380

Val Glu Leu Ser Gly Gly Ser Ser Gly Gly Ser Ser Gly Ser Glu
    1385                1390                1395

Thr Pro Gly Thr Ser Glu Ser Ala Thr Pro Glu Ser Ser Gly Gly
    1400                1405                1410

Ser Ser Gly Gly Ser Arg Pro Asp His Leu Leu Leu Lys Thr Gln
    1415                1420                1425

Thr Gln Thr Glu Gln Val Met Asn Val Thr Asn Pro Asn Ser Ile
    1430                1435                1440

Tyr Ile Lys Gly Arg Leu Tyr Phe Lys Gly Tyr Lys Lys Ile Glu
    1445                1450                1455

Leu His Cys Phe Val Asp Thr Gly Ala Ser Leu Cys Ile Ala Ser
    1460                1465                1470

Lys Phe Val Ile Pro Glu Glu His Trp Val Asn Ala Glu Arg Pro
    1475                1480                1485

Ile Met Val Lys Ile Ala Asp Gly Ser Ser Ile Thr Ile Ser Lys
    1490                1495                1500

Val Cys Lys Asp Ile Asp Leu Ile Ile Ala Gly Glu Ile Phe Arg
    1505                1510                1515

Ile Pro Thr Val Tyr Gln Gln Glu Ser Gly Ile Asp Phe Ile Ile
    1520                1525                1530

Gly Asn Asn Phe Cys Gln Leu Tyr Glu Pro Phe Ile Gln Phe Thr
    1535                1540                1545

Asp Arg Val Ile Phe Thr Lys Asn Lys Ser Tyr Pro Val His Ile
    1550                1555                1560

Ala Lys Leu Thr Arg Ala Val Arg Val Gly Thr Glu Gly Phe Leu
    1565                1570                1575

Glu Ser Met Lys Lys Arg Ser Lys Thr Gln Gln Pro Glu Pro Val
    1580                1585                1590

Asn Ile Ser Thr Asn Lys Ile Glu Asn Pro Leu Glu Glu Ile Ala
    1595                1600                1605

Ile Leu Ser Glu Gly Arg Arg Leu Ser Glu Glu Lys Leu Phe Ile
    1610                1615                1620

Thr Gln Gln Arg Met Gln Lys Ile Glu Glu Leu Leu Glu Lys Val
    1625                1630                1635

Cys Ser Glu Asn Pro Leu Asp Pro Asn Lys Thr Lys Gln Trp Met
    1640                1645                1650

Lys Ala Ser Ile Lys Leu Ser Asp Pro Ser Lys Ala Ile Lys Val
    1655                1660                1665

Lys Pro Met Lys Tyr Ser Pro Met Asp Arg Glu Glu Phe Asp Lys
    1670                1675                1680

Gln Ile Lys Glu Leu Leu Asp Leu Lys Val Ile Lys Pro Ser Lys
    1685                1690                1695

Ser Pro His Met Ala Pro Ala Phe Leu Val Asn Asn Glu Ala Glu
    1700                1705                1710
```

-continued

```
Lys Arg  Arg Gly Lys Lys Arg  Met Val Val Asn Tyr  Lys Ala Met
    1715                1720                1725

Asn Lys  Ala Thr Val Gly Asp  Ala Tyr Asn Leu Pro  Asn Lys Asp
    1730                1735                1740

Glu Leu  Leu Thr Leu Ile Arg  Gly Lys Lys Ile Phe  Ser Ser Phe
    1745                1750                1755

Asp Cys  Lys Ser Gly Phe Trp  Gln Val Leu Leu Asp  Gln Glu Ser
    1760                1765                1770

Arg Pro  Leu Thr Ala Phe Thr  Cys Pro Gln Gly His  Tyr Glu Trp
    1775                1780                1785

Asn Val  Val Pro Phe Gly Leu  Lys Gln Ala Pro Ser  Ile Phe Gln
    1790                1795                1800

Arg His  Met Asp Glu Ala Phe  Arg Val Phe Arg Lys  Phe Cys Cys
    1805                1810                1815

Val Tyr  Val Asp Asp Ile Leu  Val Phe Ser Asn Asn  Glu Glu Asp
    1820                1825                1830

His Leu  Leu His Val Ala Met  Ile Leu Gln Lys Cys  Asn Gln His
    1835                1840                1845

Gly Ile  Ile Leu Ser Lys Lys  Lys Ala Gln Leu Phe  Lys Lys Lys
    1850                1855                1860

Ile Asn  Phe Leu Gly Leu Glu  Ile Asp Glu Gly Thr  His Lys Pro
    1865                1870                1875

Gln Gly  His Ile Leu Glu His  Ile Asn Lys Phe Pro  Asp Thr Leu
    1880                1885                1890

Glu Asp  Lys Lys Gln Leu Gln  Arg Phe Leu Gly Ile  Leu Thr Tyr
    1895                1900                1905

Ala Ser  Asp Tyr Ile Pro Lys  Leu Ala Gln Ile Arg  Lys Pro Leu
    1910                1915                1920

Gln Ala  Lys Leu Lys Glu Asn  Val Pro Trp Arg Trp  Thr Lys Glu
    1925                1930                1935

Asp Thr  Leu Tyr Met Gln Lys  Val Lys Lys Asn Leu  Gln Gly Phe
    1940                1945                1950

Pro Pro  Leu His His Pro Leu  Pro Glu Glu Lys Leu  Ile Ile Glu
    1955                1960                1965

Thr Asp  Ala Ser Asp Asp Tyr  Trp Gly Gly Met Leu  Lys Ala Ile
    1970                1975                1980

Lys Ile  Asn Glu Gly Thr Asn  Thr Glu Leu Ile Cys  Arg Tyr Ala
    1985                1990                1995

Ser Gly  Ser Phe Lys Ala Ala  Glu Lys Asn Tyr His  Ser Asn Asp
    2000                2005                2010

Lys Glu  Thr Leu Ala Val Ile  Asn Thr Ile Lys Lys  Phe Ser Ile
    2015                2020                2025

Tyr Leu  Thr Pro Val His Phe  Leu Ile Arg Thr Asp  Asn Thr His
    2030                2035                2040

Phe Lys  Ser Phe Val Asn Leu  Asn Tyr Lys Gly Asp  Ser Lys Leu
    2045                2050                2055

Gly Arg  Asn Ile Arg Trp Gln  Ala Trp Leu Ser His  Tyr Ser Phe
    2060                2065                2070

Asp Val  Glu His Ile Lys Gly  Thr Asp Asn His Phe  Ala Asp Phe
    2075                2080                2085

Leu Ser  Arg Glu Phe Asn Lys  Val Asn Ser Ser Gly  Gly Ser Ser
    2090                2095                2100

Gly Gly  Ser Pro Lys Lys Lys  Arg Lys Val
```

2105 2110

<210> SEQ ID NO 14
<211> LENGTH: 1759
<212> TYPE: PRT
<213> ORGANISM: Artificial sequence
<220> FEATURE:
<223> OTHER INFORMATION: amino acid sequence of the fusion protein
nCas9(H840A)-retron of the invention

<400> SEQUENCE: 14

Met Pro Lys Lys Lys Arg Lys Val Asp Lys Lys Tyr Ser Ile Gly Leu
1 5 10 15

Asp Ile Gly Thr Asn Ser Val Gly Trp Ala Val Ile Thr Asp Glu Tyr
20 25 30

Lys Val Pro Ser Lys Lys Phe Lys Val Leu Gly Asn Thr Asp Arg His
35 40 45

Ser Ile Lys Lys Asn Leu Ile Gly Ala Leu Leu Phe Asp Ser Gly Glu
50 55 60

Thr Ala Glu Ala Thr Arg Leu Lys Arg Thr Ala Arg Arg Arg Tyr Thr
65 70 75 80

Arg Arg Lys Asn Arg Ile Cys Tyr Leu Gln Glu Ile Phe Ser Asn Glu
85 90 95

Met Ala Lys Val Asp Asp Ser Phe Phe His Arg Leu Glu Glu Ser Phe
100 105 110

Leu Val Glu Glu Asp Lys Lys His Glu Arg His Pro Ile Phe Gly Asn
115 120 125

Ile Val Asp Glu Val Ala Tyr His Glu Lys Tyr Pro Thr Ile Tyr His
130 135 140

Leu Arg Lys Lys Leu Val Asp Ser Thr Asp Lys Ala Asp Leu Arg Leu
145 150 155 160

Ile Tyr Leu Ala Leu Ala His Met Ile Lys Phe Arg Gly His Phe Leu
165 170 175

Ile Glu Gly Asp Leu Asn Pro Asp Asn Ser Asp Val Asp Lys Leu Phe
180 185 190

Ile Gln Leu Val Gln Thr Tyr Asn Gln Leu Phe Glu Glu Asn Pro Ile
195 200 205

Asn Ala Ser Gly Val Asp Ala Lys Ala Ile Leu Ser Ala Arg Leu Ser
210 215 220

Lys Ser Arg Arg Leu Glu Asn Leu Ile Ala Gln Leu Pro Gly Glu Lys
225 230 235 240

Lys Asn Gly Leu Phe Gly Asn Leu Ile Ala Leu Ser Leu Gly Leu Thr
245 250 255

Pro Asn Phe Lys Ser Asn Phe Asp Leu Ala Glu Asp Ala Lys Leu Gln
260 265 270

Leu Ser Lys Asp Thr Tyr Asp Asp Asp Leu Asp Asn Leu Leu Ala Gln
275 280 285

Ile Gly Asp Gln Tyr Ala Asp Leu Phe Leu Ala Ala Lys Asn Leu Ser
290 295 300

Asp Ala Ile Leu Leu Ser Asp Ile Leu Arg Val Asn Thr Glu Ile Thr
305 310 315 320

Lys Ala Pro Leu Ser Ala Ser Met Ile Lys Arg Tyr Asp Glu His His
325 330 335

Gln Asp Leu Thr Leu Leu Lys Ala Leu Val Arg Gln Gln Leu Pro Glu
340 345 350

```
Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
    530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590

Arg Phe Asn Ala Ser Leu Gly Thr Tyr His Asp Leu Leu Lys Ile Ile
        595                 600                 605

Lys Asp Lys Asp Phe Leu Asp Asn Glu Glu Asn Glu Asp Ile Leu Glu
    610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
        675                 680                 685

Phe Leu Lys Ser Asp Gly Phe Ala Asn Arg Asn Phe Met Gln Leu Ile
    690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
        755                 760                 765

Glu Met Ala Arg Glu Asn Gln Thr Thr Gln Lys Gly Gln Lys Asn Ser
```

```
    770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp Ala Ile
        835                 840                 845

Val Pro Gln Ser Phe Leu Lys Asp Asp Ser Ile Asp Asn Lys Val Leu
    850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
        915                 920                 925

Val Glu Thr Arg Gln Ile Thr Lys His Val Ala Gln Ile Leu Asp Ser
    930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val  Gly Thr Ala Leu Ile  Lys Lys Tyr
        995                 1000                1005

Pro Lys  Leu Glu Ser Glu Phe  Val Tyr Gly Asp Tyr  Lys Val Tyr
    1010                1015                1020

Asp Val  Arg Lys Met Ile Ala  Lys Ser Glu Gln Glu  Ile Gly Lys
    1025                1030                1035

Ala Thr  Ala Lys Tyr Phe Phe  Tyr Ser Asn Ile Met  Asn Phe Phe
    1040                1045                1050

Lys Thr  Glu Ile Thr Leu Ala  Asn Gly Glu Ile Arg  Lys Arg Pro
    1055                1060                1065

Leu Ile  Glu Thr Asn Gly Glu  Thr Gly Glu Ile Val  Trp Asp Lys
    1070                1075                1080

Gly Arg  Asp Phe Ala Thr Val  Arg Lys Val Leu Ser  Met Pro Gln
    1085                1090                1095

Val Asn  Ile Val Lys Lys Thr  Glu Val Gln Thr Gly  Gly Phe Ser
    1100                1105                1110

Lys Glu  Ser Ile Leu Pro Lys  Arg Asn Ser Asp Lys  Leu Ile Ala
    1115                1120                1125

Arg Lys  Lys Asp Trp Asp Pro  Lys Lys Tyr Gly Gly  Phe Asp Ser
    1130                1135                1140

Pro Thr  Val Ala Tyr Ser Val  Leu Val Val Ala Lys  Val Glu Lys
    1145                1150                1155

Gly Lys  Ser Lys Lys Leu Lys  Ser Val Lys Glu Leu  Leu Gly Ile
    1160                1165                1170

Thr Ile  Met Glu Arg Ser Ser  Phe Glu Lys Asn Pro  Ile Asp Phe
    1175                1180                1185
```

```
Leu Glu  Ala Lys Gly Tyr Lys  Glu Val Lys Lys Asp  Leu Ile Ile
    1190                 1195                 1200

Lys Leu  Pro Lys Tyr Ser Leu  Phe Glu Leu Glu Asn  Gly Arg Lys
    1205                 1210                 1215

Arg Met  Leu Ala Ser Ala Gly  Glu Leu Gln Lys Gly  Asn Glu Leu
    1220                 1225                 1230

Ala Leu  Pro Ser Lys Tyr Val  Asn Phe Leu Tyr Leu  Ala Ser His
    1235                 1240                 1245

Tyr Glu  Lys Leu Lys Gly Ser  Pro Glu Asp Asn Glu  Gln Lys Gln
    1250                 1255                 1260

Leu Phe  Val Glu Gln His Lys  His Tyr Leu Asp Glu  Ile Ile Glu
    1265                 1270                 1275

Gln Ile  Ser Glu Phe Ser Lys  Arg Val Ile Leu Ala  Asp Ala Asn
    1280                 1285                 1290

Leu Asp  Lys Val Leu Ser Ala  Tyr Asn Lys His Arg  Asp Lys Pro
    1295                 1300                 1305

Ile Arg  Glu Gln Ala Glu Asn  Ile Ile His Leu Phe  Thr Leu Thr
    1310                 1315                 1320

Asn Leu  Gly Ala Pro Ala Ala  Phe Lys Tyr Phe Asp  Thr Thr Ile
    1325                 1330                 1335

Asp Arg  Lys Arg Tyr Thr Ser  Thr Lys Glu Val Leu  Asp Ala Thr
    1340                 1345                 1350

Leu Ile  His Gln Ser Ile Thr  Gly Leu Tyr Glu Thr  Arg Ile Asp
    1355                 1360                 1365

Leu Ser  Gln Leu Gly Gly Asp  Glu Phe Pro Lys Lys  Lys Arg Lys
    1370                 1375                 1380

Val Glu  Leu Ser Gly Gly Ser  Ser Gly Gly Ser Ser  Gly Ser Glu
    1385                 1390                 1395

Thr Pro  Gly Thr Ser Glu Ser  Ala Thr Pro Glu Ser  Ser Gly Gly
    1400                 1405                 1410

Ser Ser  Gly Gly Ser Arg Pro  Gly Ile His Gly Val  Pro Ala Ala
    1415                 1420                 1425

Met Lys  Ser Ala Glu Tyr Leu  Asn Thr Phe Arg Leu  Arg Asn Leu
    1430                 1435                 1440

Gly Leu  Pro Val Met Asn Asn  Leu His Asp Met Ser  Lys Ala Thr
    1445                 1450                 1455

Arg Ile  Ser Val Glu Thr Leu  Arg Leu Leu Ile Tyr  Thr Ala Asp
    1460                 1465                 1470

Phe Arg  Tyr Arg Ile Tyr Thr  Val Glu Lys Lys Gly  Pro Glu Lys
    1475                 1480                 1485

Arg Met  Arg Thr Ile Tyr Gln  Pro Ser Arg Glu Leu  Lys Ala Leu
    1490                 1495                 1500

Gln Gly  Trp Val Leu Arg Asn  Ile Leu Asp Lys Leu  Ser Ser Ser
    1505                 1510                 1515

Pro Phe  Ser Ile Gly Phe Glu  Lys His Gln Ser Ile  Leu Asn Asn
    1520                 1525                 1530

Ala Thr  Pro His Ile Gly Ala  Asn Phe Ile Leu Asn  Ile Asp Leu
    1535                 1540                 1545

Glu Asp  Phe Phe Pro Ser Leu  Thr Ala Asn Lys Val  Phe Gly Val
    1550                 1555                 1560

Phe His  Ser Leu Gly Tyr Asn  Arg Leu Ile Ser Ser  Val Leu Thr
    1565                 1570                 1575
```

Lys Ile Cys Cys Tyr Lys Asn Leu Leu Pro Gln Gly Ala Pro Ser
1580 1585 1590

Ser Pro Lys Leu Ala Asn Leu Ile Cys Ser Lys Leu Asp Tyr Arg
1595 1600 1605

Ile Gln Gly Tyr Ala Gly Ser Arg Gly Leu Ile Tyr Thr Arg Tyr
1610 1615 1620

Ala Asp Asp Leu Thr Leu Ser Ala Gln Ser Met Lys Lys Val Val
1625 1630 1635

Lys Ala Arg Asp Phe Leu Phe Ser Ile Ile Pro Ser Glu Gly Leu
1640 1645 1650

Val Ile Asn Ser Lys Lys Thr Cys Ile Ser Gly Pro Arg Ser Gln
1655 1660 1665

Arg Lys Val Thr Gly Leu Val Ile Ser Gln Glu Lys Val Gly Ile
1670 1675 1680

Gly Arg Glu Lys Tyr Lys Glu Ile Arg Ala Lys Ile His His Ile
1685 1690 1695

Phe Cys Gly Lys Ser Ser Glu Ile Glu His Val Arg Gly Trp Leu
1700 1705 1710

Ser Phe Ile Leu Ser Val Asp Ser Lys Ser His Arg Arg Leu Ile
1715 1720 1725

Thr Tyr Ile Ser Lys Leu Glu Lys Lys Tyr Gly Lys Asn Pro Leu
1730 1735 1740

Asn Lys Ala Lys Thr Ser Gly Gly Ser Pro Lys Lys Lys Arg Lys
1745 1750 1755

Val

<210> SEQ ID NO 15
<211> LENGTH: 5
<212> TYPE: PRT
<213> ORGANISM: Artificial sequence
<220> FEATURE:
<223> OTHER INFORMATION: GGGGS Linker

<400> SEQUENCE: 15

Gly Gly Gly Gly Ser
1 5

<210> SEQ ID NO 16
<211> LENGTH: 15
<212> TYPE: PRT
<213> ORGANISM: Artificial sequence
<220> FEATURE:
<223> OTHER INFORMATION: (GGGGS)x3 Linker

<400> SEQUENCE: 16

Gly Gly Gly Gly Ser Gly Gly Gly Gly Ser Gly Gly Gly Gly Ser
1 5 10 15

<210> SEQ ID NO 17
<211> LENGTH: 21
<212> TYPE: PRT
<213> ORGANISM: Artificial sequence
<220> FEATURE:
<223> OTHER INFORMATION: (GGS)x7 Linker

<400> SEQUENCE: 17

Gly Gly Ser Gly Gly Ser Gly Gly Ser Gly Gly Ser Gly Gly Ser Gly
1 5 10 15

Gly Ser Gly Gly Ser
20

<210> SEQ ID NO 18
<211> LENGTH: 23
<212> TYPE: DNA
<213> ORGANISM: Artificial sequence
<220> FEATURE:
<223> OTHER INFORMATION: BFP-peg01

<400> SEQUENCE: 18
ctcgtgacca ccttcaccca cgg 23

<210> SEQ ID NO 19
<211> LENGTH: 26
<212> TYPE: DNA
<213> ORGANISM: Artificial sequence
<220> FEATURE:
<223> OTHER INFORMATION: BFP-peg01

<400> SEQUENCE: 19
tgcacgccgt acgtgaaggt ggtcac 26

<210> SEQ ID NO 20
<211> LENGTH: 23
<212> TYPE: DNA
<213> ORGANISM: Artificial sequence
<220> FEATURE:
<223> OTHER INFORMATION: OsAAT-peg01

<400> SEQUENCE: 20
caaggatccc agccccgtga agg 23

<210> SEQ ID NO 21
<211> LENGTH: 25
<212> TYPE: DNA
<213> ORGANISM: Artificial sequence
<220> FEATURE:
<223> OTHER INFORMATION: OsAAT-peg01

<400> SEQUENCE: 21
agattgacct ggacggggct gggat 25

<210> SEQ ID NO 22
<211> LENGTH: 23
<212> TYPE: DNA
<213> ORGANISM: Artificial sequence
<220> FEATURE:
<223> OTHER INFORMATION: OsALS-T1-peg01

<400> SEQUENCE: 22
gggtatggtg gtgcaatggg agg 23

<210> SEQ ID NO 23
<211> LENGTH: 28
<212> TYPE: DNA
<213> ORGANISM: Artificial sequence
<220> FEATURE:
<223> OTHER INFORMATION: OsALS-T1-peg01

<400> SEQUENCE: 23
taaaacctat cctccaattg caccacca 28

<210> SEQ ID NO 24
<211> LENGTH: 23
<212> TYPE: DNA
<213> ORGANISM: Artificial sequence
<220> FEATURE:

<223> OTHER INFORMATION: OsALS-T2-peg01

<400> SEQUENCE: 24
gtgctgccta tgatcccaag tgg 23

<210> SEQ ID NO 25
<211> LENGTH: 27
<212> TYPE: DNA
<213> ORGANISM: Artificial sequence
<220> FEATURE:
<223> OTHER INFORMATION: OsALS-T2-peg01

<400> SEQUENCE: 25
tgaatgcgcc cccaattggg atcatag 27

<210> SEQ ID NO 26
<211> LENGTH: 23
<212> TYPE: DNA
<213> ORGANISM: Artificial sequence
<220> FEATURE:
<223> OTHER INFORMATION: OsALS-T2-peg02

<400> SEQUENCE: 26
gtgctgccta tgatcccaag tgg 23

<210> SEQ ID NO 27
<211> LENGTH: 27
<212> TYPE: DNA
<213> ORGANISM: Artificial sequence
<220> FEATURE:
<223> OTHER INFORMATION: OsALS-T2-peg02

<400> SEQUENCE: 27
tgaatgcgcc cccacctggg atcatag 27

<210> SEQ ID NO 28
<211> LENGTH: 23
<212> TYPE: DNA
<213> ORGANISM: Artificial sequence
<220> FEATURE:
<223> OTHER INFORMATION: OsALS-T2-pegAT

<400> SEQUENCE: 28
gtgctgccta tgatcccaag tgg 23

<210> SEQ ID NO 29
<211> LENGTH: 27
<212> TYPE: DNA
<213> ORGANISM: Artificial sequence
<220> FEATURE:
<223> OTHER INFORMATION: OsALS-T2-pegAT

<400> SEQUENCE: 29
tgaatgcgcc cccacatggg atcatag 27

<210> SEQ ID NO 30
<211> LENGTH: 23
<212> TYPE: DNA
<213> ORGANISM: Artificial sequence
<220> FEATURE:
<223> OTHER INFORMATION: OsALS-T2-pegAC

<400> SEQUENCE: 30
gtgctgccta tgatcccaag tgg 23

<210> SEQ ID NO 31
<211> LENGTH: 27
<212> TYPE: DNA
<213> ORGANISM: Artificial sequence
<220> FEATURE:
<223> OTHER INFORMATION: OsALS-T2-pegAC

<400> SEQUENCE: 31
tgaatgcgcc cccacgtggg atcatag 27

<210> SEQ ID NO 32
<211> LENGTH: 23
<212> TYPE: DNA
<213> ORGANISM: Artificial sequence
<220> FEATURE:
<223> OTHER INFORMATION: OsALS-T2-pegTA

<400> SEQUENCE: 32
gtgctgccta tgatcccaag tgg 23

<210> SEQ ID NO 33
<211> LENGTH: 27
<212> TYPE: DNA
<213> ORGANISM: Artificial sequence
<220> FEATURE:
<223> OTHER INFORMATION: OsALS-T2-pegTA

<400> SEQUENCE: 33
tgaatgcgcc ccctcttggg atcatag 27

<210> SEQ ID NO 34
<211> LENGTH: 23
<212> TYPE: DNA
<213> ORGANISM: Artificial sequence
<220> FEATURE:
<223> OTHER INFORMATION: OsALS-T2-pegTC

<400> SEQUENCE: 34
gtgctgccta tgatcccaag tgg 23

<210> SEQ ID NO 35
<211> LENGTH: 27
<212> TYPE: DNA
<213> ORGANISM: Artificial sequence
<220> FEATURE:
<223> OTHER INFORMATION: OsALS-T2-pegTC

<400> SEQUENCE: 35
tgaatgcgcc cccgcttggg atcatag 27

<210> SEQ ID NO 36
<211> LENGTH: 23
<212> TYPE: DNA
<213> ORGANISM: Artificial sequence
<220> FEATURE:
<223> OTHER INFORMATION: OsALS-T2-pegTG

<400> SEQUENCE: 36
gtgctgccta tgatcccaag tgg 23

<210> SEQ ID NO 37

<400> SEQUENCE: 37

000

<210> SEQ ID NO 38
<211> LENGTH: 23
<212> TYPE: DNA
<213> ORGANISM: Artificial sequence
<220> FEATURE:
<223> OTHER INFORMATION: OsALS-T2-pegGA

<400> SEQUENCE: 38
gtgctgccta tgatcccaag tgg 23

<210> SEQ ID NO 39
<211> LENGTH: 27
<212> TYPE: DNA
<213> ORGANISM: Artificial sequence
<220> FEATURE:
<223> OTHER INFORMATION: OsALS-T2-pegGA

<400> SEQUENCE: 39
tgaatgcgcc cccatttggg atcatag 27

<210> SEQ ID NO 40
<211> LENGTH: 23
<212> TYPE: DNA
<213> ORGANISM: Artificial sequence
<220> FEATURE:
<223> OTHER INFORMATION: OsALS-T2-pegAGCA

<400> SEQUENCE: 40
gtgctgccta tgatcccaag tgg 23

<210> SEQ ID NO 41
<211> LENGTH: 27
<212> TYPE: DNA
<213> ORGANISM: Artificial sequence
<220> FEATURE:
<223> OTHER INFORMATION: OsALS-T2-pegAGCA

<400> SEQUENCE: 41
tgaatgcgcc cccatgtggg atcatag 27

<210> SEQ ID NO 42

<400> SEQUENCE: 42

000

<210> SEQ ID NO 43
<211> LENGTH: 23
<212> TYPE: DNA
<213> ORGANISM: Artificial sequence
<220> FEATURE:
<223> OTHER INFORMATION: OsALS-T2-pegPBS6

<400> SEQUENCE: 43
tgaatgcgcc cccacctggg atc 23

<210> SEQ ID NO 44

<400> SEQUENCE: 44

000

<210> SEQ ID NO 45
<211> LENGTH: 25
<212> TYPE: DNA
<213> ORGANISM: Artificial sequence
<220> FEATURE:

<223> OTHER INFORMATION: OsALS-T2-pegPBS8

<400> SEQUENCE: 45
tgaatgcgcc cccacctggg atcat 25

<210> SEQ ID NO 46
<211> LENGTH: 23
<212> TYPE: DNA
<213> ORGANISM: Artificial sequence
<220> FEATURE:
<223> OTHER INFORMATION: OsALS-T2-pegPBS12

<400> SEQUENCE: 46
gtgctgccta tgatcccaag tgg 23

<210> SEQ ID NO 47
<211> LENGTH: 29
<212> TYPE: DNA
<213> ORGANISM: Artificial sequence
<220> FEATURE:
<223> OTHER INFORMATION: OsALS-T2-pegPBS12

<400> SEQUENCE: 47
tgaatgcgcc cccacctggg atcataggc 29

<210> SEQ ID NO 48

<400> SEQUENCE: 48

000

<210> SEQ ID NO 49
<211> LENGTH: 31
<212> TYPE: DNA
<213> ORGANISM: Artificial sequence
<220> FEATURE:
<223> OTHER INFORMATION: OsALS-T2-pegPBS14

<400> SEQUENCE: 49
tgaatgcgcc cccacctggg atcataggca g 31

<210> SEQ ID NO 50
<211> LENGTH: 23
<212> TYPE: DNA
<213> ORGANISM: Artificial sequence
<220> FEATURE:
<223> OTHER INFORMATION: OsALS-T2-pegPBS16

<400> SEQUENCE: 50
gtgctgccta tgatcccaag tgg 23

<210> SEQ ID NO 51
<211> LENGTH: 33
<212> TYPE: DNA
<213> ORGANISM: Artificial sequence
<220> FEATURE:
<223> OTHER INFORMATION: OsALS-T2-pegPBS16

<400> SEQUENCE: 51
tgaatgcgcc cccacctggg atcataggca gca 33

<210> SEQ ID NO 52
<211> LENGTH: 23
<212> TYPE: DNA
<213> ORGANISM: Artificial sequence
<220> FEATURE:

<223> OTHER INFORMATION: OsALS-T2-pegRT10

<400> SEQUENCE: 52
gtgctgccta tgatcccaag tgg 23

<210> SEQ ID NO 53
<211> LENGTH: 20
<212> TYPE: DNA
<213> ORGANISM: Artificial sequence
<220> FEATURE:
<223> OTHER INFORMATION: OsALS-T2-pegRT10

<400> SEQUENCE: 53
gcccccacct gggatcatag 20

<210> SEQ ID NO 54
<211> LENGTH: 23
<212> TYPE: DNA
<213> ORGANISM: Artificial sequence
<220> FEATURE:
<223> OTHER INFORMATION: OsALS-T2-pegRT11

<400> SEQUENCE: 54
gtgctgccta tgatcccaag tgg 23

<210> SEQ ID NO 55
<211> LENGTH: 21
<212> TYPE: DNA
<213> ORGANISM: Artificial sequence
<220> FEATURE:
<223> OTHER INFORMATION: OsALS-T2-pegRT11

<400> SEQUENCE: 55
cgcccccacc tgggatcata g 21

<210> SEQ ID NO 56
<211> LENGTH: 23
<212> TYPE: DNA
<213> ORGANISM: Artificial sequence
<220> FEATURE:
<223> OTHER INFORMATION: OsALS-T2-pegRT13

<400> SEQUENCE: 56
gtgctgccta tgatcccaag tgg 23

<210> SEQ ID NO 57
<211> LENGTH: 23
<212> TYPE: DNA
<213> ORGANISM: Artificial sequence
<220> FEATURE:
<223> OTHER INFORMATION: OsALS-T2-pegRT13

<400> SEQUENCE: 57
tgcgccccca cctgggatca tag 23

<210> SEQ ID NO 58
<211> LENGTH: 23
<212> TYPE: DNA
<213> ORGANISM: Artificial sequence
<220> FEATURE:
<223> OTHER INFORMATION: OsALS-T2-pegRT15

<400> SEQUENCE: 58
gtgctgccta tgatcccaag tgg 23

<210> SEQ ID NO 59
<211> LENGTH: 25
<212> TYPE: DNA
<213> ORGANISM: Artificial sequence
<220> FEATURE:
<223> OTHER INFORMATION: OsALS-T2-pegRT15

<400> SEQUENCE: 59
aatgcgcccc cacctgggat catag 25

<210> SEQ ID NO 60
<211> LENGTH: 23
<212> TYPE: DNA
<213> ORGANISM: Artificial sequence
<220> FEATURE:
<223> OTHER INFORMATION: OsALS-T2-pegRT18

<400> SEQUENCE: 60
gtgctgccta tgatcccaag tgg 23

<210> SEQ ID NO 61
<211> LENGTH: 28
<212> TYPE: DNA
<213> ORGANISM: Artificial sequence
<220> FEATURE:
<223> OTHER INFORMATION: OsALS-T2-pegRT18

<400> SEQUENCE: 61
ttgaatgcgc ccccacctgg gatcatag 28

<210> SEQ ID NO 62
<211> LENGTH: 23
<212> TYPE: DNA
<213> ORGANISM: Artificial sequence
<220> FEATURE:
<223> OTHER INFORMATION: OsALS-T2-pegRT19

<400> SEQUENCE: 62
gtgctgccta tgatcccaag tgg 23

<210> SEQ ID NO 63
<211> LENGTH: 29
<212> TYPE: DNA
<213> ORGANISM: Artificial sequence
<220> FEATURE:
<223> OTHER INFORMATION: OsALS-T2-pegRT19

<400> SEQUENCE: 63
cttgaatgcg cccccacctg ggatcatag 29

<210> SEQ ID NO 64
<211> LENGTH: 23
<212> TYPE: DNA
<213> ORGANISM: Artificial sequence
<220> FEATURE:
<223> OTHER INFORMATION: OsALS-T2-pegRT21

<400> SEQUENCE: 64
gtgctgccta tgatcccaag tgg 23

<210> SEQ ID NO 65
<211> LENGTH: 31
<212> TYPE: DNA
<213> ORGANISM: Artificial sequence
<220> FEATURE:
<223> OTHER INFORMATION: OsALS-T2-pegRT21

<400> SEQUENCE: 65
tccttgaatg cgcccccacc tgggatcata g 31

<210> SEQ ID NO 66
<211> LENGTH: 23
<212> TYPE: DNA
<213> ORGANISM: Artificial sequence
<220> FEATURE:
<223> OTHER INFORMATION: OsALS-T2-pegRT23

<400> SEQUENCE: 66
gtgctgccta tgatcccaag tgg 23

<210> SEQ ID NO 67
<211> LENGTH: 33
<212> TYPE: DNA
<213> ORGANISM: Artificial sequence
<220> FEATURE:
<223> OTHER INFORMATION: OsALS-T2-pegRT23

<400> SEQUENCE: 67
tgtccttgaa tgcgccccca cctgggatca tag 33

<210> SEQ ID NO 68
<211> LENGTH: 23
<212> TYPE: DNA
<213> ORGANISM: Artificial sequence
<220> FEATURE:
<223> OTHER INFORMATION: OsCDC48-T1-peg01

<400> SEQUENCE: 68
gctagctttg acataatctc cgg 23

<210> SEQ ID NO 69
<211> LENGTH: 21
<212> TYPE: DNA
<213> ORGANISM: Artificial sequence
<220> FEATURE:
<223> OTHER INFORMATION: OsCDC48-T1-peg01

<400> SEQUENCE: 69
attaatggca ttatgtcaaa g 21

<210> SEQ ID NO 70
<211> LENGTH: 23
<212> TYPE: DNA
<213> ORGANISM: Artificial sequence
<220> FEATURE:
<223> OTHER INFORMATION: OsCDC48-T1-peg02

<400> SEQUENCE: 70
gctagctttg acataatctc cgg 23

<210> SEQ ID NO 71
<211> LENGTH: 27
<212> TYPE: DNA
<213> ORGANISM: Artificial sequence
<220> FEATURE:
<223> OTHER INFORMATION: OsCDC48-T1-peg02

<400> SEQUENCE: 71
attaatggcc ttaagattat gtcaaag 27

<210> SEQ ID NO 72
<211> LENGTH: 23

<212> TYPE: DNA
<213> ORGANISM: Artificial sequence
<220> FEATURE:
<223> OTHER INFORMATION: OsCDC48-T1-peg03

<400> SEQUENCE: 72
gctagctttg acataatctc cgg 23

<210> SEQ ID NO 73
<211> LENGTH: 30
<212> TYPE: DNA
<213> ORGANISM: Artificial sequence
<220> FEATURE:
<223> OTHER INFORMATION: OsCDC48-T1-peg03

<400> SEQUENCE: 73
attaatggcc cggatccgat tatgtcaaag 30

<210> SEQ ID NO 74
<211> LENGTH: 23
<212> TYPE: DNA
<213> ORGANISM: Artificial sequence
<220> FEATURE:
<223> OTHER INFORMATION: OsCDC48-T1-pegAT

<400> SEQUENCE: 74
gctagctttg acataatctc cgg 23

<210> SEQ ID NO 75
<211> LENGTH: 39
<212> TYPE: DNA
<213> ORGANISM: Artificial sequence
<220> FEATURE:
<223> OTHER INFORMATION: OsCDC48-T1-pegAT

<400> SEQUENCE: 75
ttcttctttc tgattaaagg cccggagatt atgtcaaag 39

<210> SEQ ID NO 76
<211> LENGTH: 23
<212> TYPE: DNA
<213> ORGANISM: Artificial sequence
<220> FEATURE:
<223> OTHER INFORMATION: OsCDC48-T1-pegAC

<400> SEQUENCE: 76
gctagctttg acataatctc cgg 23

<210> SEQ ID NO 77
<211> LENGTH: 39
<212> TYPE: DNA
<213> ORGANISM: Artificial sequence
<220> FEATURE:
<223> OTHER INFORMATION: OsCDC48-T1-pegAC

<400> SEQUENCE: 77
ttcttctttc tgattaaggg cccggagatt atgtcaaag 39

<210> SEQ ID NO 78
<211> LENGTH: 23
<212> TYPE: DNA
<213> ORGANISM: Artificial sequence
<220> FEATURE:
<223> OTHER INFORMATION: OsCDC48-T1-pegAG

<400> SEQUENCE: 78
gctagctttg acataatctc cgg 23

<210> SEQ ID NO 79
<211> LENGTH: 39
<212> TYPE: DNA
<213> ORGANISM: Artificial sequence
<220> FEATURE:
<223> OTHER INFORMATION: OsCDC48-T1-pegAG

<400> SEQUENCE: 79
ttcttctttc tgattaacgg cccggagatt atgtcaaag 39

<210> SEQ ID NO 80
<211> LENGTH: 23
<212> TYPE: DNA
<213> ORGANISM: Artificial sequence
<220> FEATURE:
<223> OTHER INFORMATION: OsCDC48-T1-pegCA

<400> SEQUENCE: 80
gctagctttg acataatctc cgg 23

<210> SEQ ID NO 81
<211> LENGTH: 27
<212> TYPE: DNA
<213> ORGANISM: Artificial sequence
<220> FEATURE:
<223> OTHER INFORMATION: OsCDC48-T1-pegCA

<400> SEQUENCE: 81
attaatggcc cggatattat gtcaaag 27

<210> SEQ ID NO 82
<211> LENGTH: 23
<212> TYPE: DNA
<213> ORGANISM: Artificial sequence
<220> FEATURE:
<223> OTHER INFORMATION: OsCDC48-T1-pegCT

<400> SEQUENCE: 82
gctagctttg acataatctc cgg 23

<210> SEQ ID NO 83
<211> LENGTH: 27
<212> TYPE: DNA
<213> ORGANISM: Artificial sequence
<220> FEATURE:
<223> OTHER INFORMATION: OsCDC48-T1-pegCT

<400> SEQUENCE: 83
attaatggcc cggaaattat gtcaaag 27

<210> SEQ ID NO 84
<211> LENGTH: 23
<212> TYPE: DNA
<213> ORGANISM: Artificial sequence
<220> FEATURE:
<223> OTHER INFORMATION: OsCDC48-T1-pegCG

<400> SEQUENCE: 84
gctagctttg acataatctc cgg 23

<210> SEQ ID NO 85
<211> LENGTH: 27
<212> TYPE: DNA
<213> ORGANISM: Artificial sequence
<220> FEATURE:
<223> OTHER INFORMATION: OsCDC48-T1-pegCG

<400> SEQUENCE: 85
attaatggcc cggacattat gtcaaag 27

<210> SEQ ID NO 86
<211> LENGTH: 23
<212> TYPE: DNA
<213> ORGANISM: Artificial sequence
<220> FEATURE:
<223> OTHER INFORMATION: OsCDC48-T1-pegGA

<400> SEQUENCE: 86
gctagctttg acataatctc cgg 23

<210> SEQ ID NO 87
<211> LENGTH: 27
<212> TYPE: DNA
<213> ORGANISM: Artificial sequence
<220> FEATURE:
<223> OTHER INFORMATION: OsCDC48-T1-pegGA

<400> SEQUENCE: 87
attaatggcc tggagattat gtcaaag 27

<210> SEQ ID NO 88
<211> LENGTH: 23
<212> TYPE: DNA
<213> ORGANISM: Artificial sequence
<220> FEATURE:
<223> OTHER INFORMATION: OsCDC48-T1-pegGC

<400> SEQUENCE: 88
gctagctttg acataatctc cgg 23

<210> SEQ ID NO 89
<211> LENGTH: 27
<212> TYPE: DNA
<213> ORGANISM: Artificial sequence
<220> FEATURE:
<223> OTHER INFORMATION: OsCDC48-T1-pegGC

<400> SEQUENCE: 89
attaatggcc gggagattat gtcaaag 27

<210> SEQ ID NO 90
<211> LENGTH: 23
<212> TYPE: DNA
<213> ORGANISM: Artificial sequence
<220> FEATURE:
<223> OTHER INFORMATION: OsCDC48-T1-pegGT

<400> SEQUENCE: 90
gctagctttg acataatctc cgg 23

<210> SEQ ID NO 91
<211> LENGTH: 27
<212> TYPE: DNA
<213> ORGANISM: Artificial sequence
<220> FEATURE:
<223> OTHER INFORMATION: OsCDC48-T1-pegGT

<400> SEQUENCE: 91
attaatggcc aggagattat gtcaaag 27

<210> SEQ ID NO 92
<211> LENGTH: 23
<212> TYPE: DNA
<213> ORGANISM: Artificial sequence
<220> FEATURE:
<223> OTHER INFORMATION: OsCDC48-T1-pegTA

<400> SEQUENCE: 92
gctagctttg acataatctc cgg 23

<210> SEQ ID NO 93
<211> LENGTH: 27
<212> TYPE: DNA
<213> ORGANISM: Artificial sequence
<220> FEATURE:
<223> OTHER INFORMATION: OsCDC48-T1-pegTA

<400> SEQUENCE: 93
attaatggcc cggtgattat gtcaaag 27

<210> SEQ ID NO 94
<211> LENGTH: 23
<212> TYPE: DNA
<213> ORGANISM: Artificial sequence
<220> FEATURE:
<223> OTHER INFORMATION: OsCDC48-T1-pegTC

<400> SEQUENCE: 94
gctagctttg acataatctc cgg 23

<210> SEQ ID NO 95
<211> LENGTH: 27
<212> TYPE: DNA
<213> ORGANISM: Artificial sequence
<220> FEATURE:
<223> OTHER INFORMATION: OsCDC48-T1-pegTC

<400> SEQUENCE: 95
attaatggcc cggggattat gtcaaag 27

<210> SEQ ID NO 96
<211> LENGTH: 23
<212> TYPE: DNA
<213> ORGANISM: Artificial sequence
<220> FEATURE:
<223> OTHER INFORMATION: OsCDC48-T1-pegTG

<400> SEQUENCE: 96
gctagctttg acataatctc cgg 23

<210> SEQ ID NO 97
<211> LENGTH: 27
<212> TYPE: DNA
<213> ORGANISM: Artificial sequence
<220> FEATURE:
<223> OTHER INFORMATION: OsCDC48-T1-pegTG

<400> SEQUENCE: 97
attaatggcc cggcgattat gtcaaag 27

<210> SEQ ID NO 98
<211> LENGTH: 23
<212> TYPE: DNA
<213> ORGANISM: Artificial sequence
<220> FEATURE:
<223> OTHER INFORMATION: OsCDC48-T1-pegPBS8

<400> SEQUENCE: 98
gctagctttg acataatctc cgg 23

<210> SEQ ID NO 99
<211> LENGTH: 17
<212> TYPE: DNA
<213> ORGANISM: Artificial sequence
<220> FEATURE:
<223> OTHER INFORMATION: OsCDC48-T1-pegPBS8

<400> SEQUENCE: 99
attaatggca ttatgtc 17

<210> SEQ ID NO 100
<211> LENGTH: 23
<212> TYPE: DNA
<213> ORGANISM: Artificial sequence
<220> FEATURE:
<223> OTHER INFORMATION: OsCDC48-T1-pegPBS10

<400> SEQUENCE: 100
gctagctttg acataatctc cgg 23

<210> SEQ ID NO 101
<211> LENGTH: 19
<212> TYPE: DNA
<213> ORGANISM: Artificial sequence
<220> FEATURE:
<223> OTHER INFORMATION: OsCDC48-T1-pegPBS10

<400> SEQUENCE: 101
attaatggca ttatgtcaa 19

<210> SEQ ID NO 102
<211> LENGTH: 23
<212> TYPE: DNA
<213> ORGANISM: Artificial sequence
<220> FEATURE:
<223> OTHER INFORMATION: OsCDC48-T1-pegPBS14

<400> SEQUENCE: 102
gctagctttg acataatctc cgg 23

<210> SEQ ID NO 103
<211> LENGTH: 23
<212> TYPE: DNA
<213> ORGANISM: Artificial sequence
<220> FEATURE:
<223> OTHER INFORMATION: OsCDC48-T1-pegPBS14

<400> SEQUENCE: 103
attaatggca ttatgtcaaa gct 23

<210> SEQ ID NO 104
<211> LENGTH: 23
<212> TYPE: DNA
<213> ORGANISM: Artificial sequence
<220> FEATURE:
<223> OTHER INFORMATION: OsCDC48-T1-pegPBS16

<400> SEQUENCE: 104
gctagctttg acataatctc cgg 23

<210> SEQ ID NO 105

<211> LENGTH: 25
<212> TYPE: DNA
<213> ORGANISM: Artificial sequence
<220> FEATURE:
<223> OTHER INFORMATION: OsCDC48-T1-pegPBS16

<400> SEQUENCE: 105
attaatggca ttatgtcaaa gctag 25

<210> SEQ ID NO 106
<211> LENGTH: 23
<212> TYPE: DNA
<213> ORGANISM: Artificial sequence
<220> FEATURE:
<223> OTHER INFORMATION: OsCDC48-T1-pegRT7

<400> SEQUENCE: 106
gctagctttg acataatctc cgg 23

<210> SEQ ID NO 107
<211> LENGTH: 19
<212> TYPE: DNA
<213> ORGANISM: Artificial sequence
<220> FEATURE:
<223> OTHER INFORMATION: OsCDC48-T1-pegRT7

<400> SEQUENCE: 107
taatggcatt atgtcaaag 19

<210> SEQ ID NO 108
<211> LENGTH: 23
<212> TYPE: DNA
<213> ORGANISM: Artificial sequence
<220> FEATURE:
<223> OTHER INFORMATION: OsCDC48-T1-pegRT11

<400> SEQUENCE: 108
gctagctttg acataatctc cgg 23

<210> SEQ ID NO 109
<211> LENGTH: 23
<212> TYPE: DNA
<213> ORGANISM: Artificial sequence
<220> FEATURE:
<223> OTHER INFORMATION: OsCDC48-T1-pegRT11

<400> SEQUENCE: 109
tgattaatgg cattatgtca aag 23

<210> SEQ ID NO 110
<211> LENGTH: 23
<212> TYPE: DNA
<213> ORGANISM: Artificial sequence
<220> FEATURE:
<223> OTHER INFORMATION: OsCDC48-T1-pegRT13

<400> SEQUENCE: 110
gctagctttg acataatctc cgg 23

<210> SEQ ID NO 111
<211> LENGTH: 25
<212> TYPE: DNA
<213> ORGANISM: Artificial sequence
<220> FEATURE:
<223> OTHER INFORMATION: OsCDC48-T1-pegRT13

<400> SEQUENCE: 111
tctgattaat ggcattatgt caaag 25

<210> SEQ ID NO 112
<211> LENGTH: 23
<212> TYPE: DNA
<213> ORGANISM: Artificial sequence
<220> FEATURE:
<223> OTHER INFORMATION: OsCDC48-T1-pegRT15

<400> SEQUENCE: 112
gctagctttg acataatctc cgg 23

<210> SEQ ID NO 113
<211> LENGTH: 27
<212> TYPE: DNA
<213> ORGANISM: Artificial sequence
<220> FEATURE:
<223> OTHER INFORMATION: OsCDC48-T1-pegRT15

<400> SEQUENCE: 113
tttctgatta atggcattat gtcaaag 27

<210> SEQ ID NO 114
<211> LENGTH: 23
<212> TYPE: DNA
<213> ORGANISM: Artificial sequence
<220> FEATURE:
<223> OTHER INFORMATION: OsCDC48-T1-pegins3

<400> SEQUENCE: 114
gctagctttg acataatctc cgg 23

<210> SEQ ID NO 115
<211> LENGTH: 30
<212> TYPE: DNA
<213> ORGANISM: Artificial sequence
<220> FEATURE:
<223> OTHER INFORMATION: OsCDC48-T1-pegins3

<400> SEQUENCE: 115
attaatggcc cggagaccat tatgtcaaag 30

<210> SEQ ID NO 116
<211> LENGTH: 23
<212> TYPE: DNA
<213> ORGANISM: Artificial sequence
<220> FEATURE:
<223> OTHER INFORMATION: OsCDC48-T1-pegins6

<400> SEQUENCE: 116
gctagctttg acataatctc cgg 23

<210> SEQ ID NO 117
<211> LENGTH: 33
<212> TYPE: DNA
<213> ORGANISM: Artificial sequence
<220> FEATURE:
<223> OTHER INFORMATION: OsCDC48-T1-pegins6

<400> SEQUENCE: 117
attaatggcc cggagaccaa cattatgtca aag 33

<210> SEQ ID NO 118
<211> LENGTH: 23
<212> TYPE: DNA

<213> ORGANISM: Artificial sequence
<220> FEATURE:
<223> OTHER INFORMATION: OsCDC48-T1-pegins15

<400> SEQUENCE: 118
gctagctttg acataatctc cgg 23

<210> SEQ ID NO 119
<211> LENGTH: 42
<212> TYPE: DNA
<213> ORGANISM: Artificial sequence
<220> FEATURE:
<223> OTHER INFORMATION: OsCDC48-T1-pegins15

<400> SEQUENCE: 119
attaatggcc cggagaccaa cctgtccgac attatgtcaa ag 42

<210> SEQ ID NO 120
<211> LENGTH: 23
<212> TYPE: DNA
<213> ORGANISM: Artificial sequence
<220> FEATURE:
<223> OTHER INFORMATION: OsCDC48-T1-pegins30

<400> SEQUENCE: 120
gctagctttg acataatctc cgg 23

<210> SEQ ID NO 121
<211> LENGTH: 57
<212> TYPE: DNA
<213> ORGANISM: Artificial sequence
<220> FEATURE:
<223> OTHER INFORMATION: OsCDC48-T1-pegins30

<400> SEQUENCE: 121
attaatggcc cggagaccaa cctgtccgac atcatcgaga aggagattat gtcaaag 57

<210> SEQ ID NO 122
<211> LENGTH: 23
<212> TYPE: DNA
<213> ORGANISM: Artificial sequence
<220> FEATURE:
<223> OTHER INFORMATION: OsCDC48-T1-pegins60

<400> SEQUENCE: 122
gctagctttg acataatctc cgg 23

<210> SEQ ID NO 123
<211> LENGTH: 87
<212> TYPE: DNA
<213> ORGANISM: Artificial sequence
<220> FEATURE:
<223> OTHER INFORMATION: OsCDC48-T1-pegins60

<400> SEQUENCE: 123
attaatggcc cggagaccaa cctgtccgac atcatcgaga aggagacggg caagcaactc 60
gtgatccagg agagcattat gtcaaag 87

<210> SEQ ID NO 124
<211> LENGTH: 23
<212> TYPE: DNA
<213> ORGANISM: Artificial sequence
<220> FEATURE:
<223> OTHER INFORMATION: OsCDC48-T1-pegdel12

<400> SEQUENCE: 124
gctagctttg acataatctc cgg 23

<210> SEQ ID NO 125
<211> LENGTH: 21
<212> TYPE: DNA
<213> ORGANISM: Artificial sequence
<220> FEATURE:
<223> OTHER INFORMATION: OsCDC48-T1-pegdel12

<400> SEQUENCE: 125
tttctgatta ttatgtcaaa g 21

<210> SEQ ID NO 126
<211> LENGTH: 23
<212> TYPE: DNA
<213> ORGANISM: Artificial sequence
<220> FEATURE:
<223> OTHER INFORMATION: OsCDC48-T1-pegdel20

<400> SEQUENCE: 126
gctagctttg acataatctc cgg 23

<210> SEQ ID NO 127
<211> LENGTH: 22
<212> TYPE: DNA
<213> ORGANISM: Artificial sequence
<220> FEATURE:
<223> OTHER INFORMATION: OsCDC48-T1-pegdel20

<400> SEQUENCE: 127
gctttcttct attatgtcaa ag 22

<210> SEQ ID NO 128
<211> LENGTH: 23
<212> TYPE: DNA
<213> ORGANISM: Artificial sequence
<220> FEATURE:
<223> OTHER INFORMATION: OsCDC48-T1-pegdel40

<400> SEQUENCE: 128
gctagctttg acataatctc cgg 23

<210> SEQ ID NO 129
<211> LENGTH: 21
<212> TYPE: DNA
<213> ORGANISM: Artificial sequence
<220> FEATURE:
<223> OTHER INFORMATION: OsCDC48-T1-pegdel40

<400> SEQUENCE: 129
tgttgctaaa ttatgtcaaa g 21

<210> SEQ ID NO 130
<211> LENGTH: 23
<212> TYPE: DNA
<213> ORGANISM: Artificial sequence
<220> FEATURE:
<223> OTHER INFORMATION: OsCDC48-T1-pegdel70

<400> SEQUENCE: 130
gctagctttg acataatctc cgg 23

<210> SEQ ID NO 131
<211> LENGTH: 21
<212> TYPE: DNA

<213> ORGANISM: Artificial sequence
<220> FEATURE:
<223> OTHER INFORMATION: OsCDC48-T1-pegdel70

<400> SEQUENCE: 131
tggctctgga ttatgtcaaa g 21

<210> SEQ ID NO 132
<211> LENGTH: 23
<212> TYPE: DNA
<213> ORGANISM: Artificial sequence
<220> FEATURE:
<223> OTHER INFORMATION: OsCDC48-T2-peg01

<400> SEQUENCE: 132
gaccagccag cgtctggcgc cgg 23

<210> SEQ ID NO 133
<211> LENGTH: 25
<212> TYPE: DNA
<213> ORGANISM: Artificial sequence
<220> FEATURE:
<223> OTHER INFORMATION: OsCDC48-T2-peg01

<400> SEQUENCE: 133
ggcgccggct ttgccagacg ctggc 25

<210> SEQ ID NO 134
<211> LENGTH: 23
<212> TYPE: DNA
<213> ORGANISM: Artificial sequence
<220> FEATURE:
<223> OTHER INFORMATION: OsCDC48-T2-peg02

<400> SEQUENCE: 134
gaccagccag cgtctggcgc cgg 23

<210> SEQ ID NO 135
<211> LENGTH: 30
<212> TYPE: DNA
<213> ORGANISM: Artificial sequence
<220> FEATURE:
<223> OTHER INFORMATION: OsCDC48-T2-peg02

<400> SEQUENCE: 135
tcagcggcgg cgctggcgcc agacgctggc 30

<210> SEQ ID NO 136
<211> LENGTH: 23
<212> TYPE: DNA
<213> ORGANISM: Artificial sequence
<220> FEATURE:
<223> OTHER INFORMATION: OsCDC48-T2-pegGT

<400> SEQUENCE: 136
gaccagccag cgtctggcgc cgg 23

<210> SEQ ID NO 137
<211> LENGTH: 30
<212> TYPE: DNA
<213> ORGANISM: Artificial sequence
<220> FEATURE:
<223> OTHER INFORMATION: OsCDC48-T2-pegGT

<400> SEQUENCE: 137
tcagcggcgg cgcaggcgcc agacgctggc 30

<210> SEQ ID NO 138
<211> LENGTH: 23
<212> TYPE: DNA
<213> ORGANISM: Artificial sequence
<220> FEATURE:
<223> OTHER INFORMATION: OsCDC48-T2-pegGC

<400> SEQUENCE: 138
gaccagccag cgtctggcgc cgg 23

<210> SEQ ID NO 139
<211> LENGTH: 30
<212> TYPE: DNA
<213> ORGANISM: Artificial sequence
<220> FEATURE:
<223> OTHER INFORMATION: OsCDC48-T2-pegGC

<400> SEQUENCE: 139
tcagcggcgg cgcgggcgcc agacgctggc 30

<210> SEQ ID NO 140
<211> LENGTH: 23
<212> TYPE: DNA
<213> ORGANISM: Artificial sequence
<220> FEATURE:
<223> OTHER INFORMATION: OsCDC48-T2-pegCA

<400> SEQUENCE: 140
gaccagccag cgtctggcgc cgg 23

<210> SEQ ID NO 141
<211> LENGTH: 30
<212> TYPE: DNA
<213> ORGANISM: Artificial sequence
<220> FEATURE:
<223> OTHER INFORMATION: OsCDC48-T2-pegCA

<400> SEQUENCE: 141
tcagcggcgg cgcctgcgcc agacgctggc 30

<210> SEQ ID NO 142
<211> LENGTH: 23
<212> TYPE: DNA
<213> ORGANISM: Artificial sequence
<220> FEATURE:
<223> OTHER INFORMATION: OsCDC48-T2-pegCT

<400> SEQUENCE: 142
gaccagccag cgtctggcgc cgg 23

<210> SEQ ID NO 143
<211> LENGTH: 30
<212> TYPE: DNA
<213> ORGANISM: Artificial sequence
<220> FEATURE:
<223> OTHER INFORMATION: OsCDC48-T2-pegCT

<400> SEQUENCE: 143
tcagcggcgg cgccagcgcc agacgctggc 30

<210> SEQ ID NO 144
<211> LENGTH: 23
<212> TYPE: DNA
<213> ORGANISM: Artificial sequence
<220> FEATURE:

<223> OTHER INFORMATION: OsCDC48-T2-pegDel

<400> SEQUENCE: 144
gaccagccag cgtctggcgc cgg 23

<210> SEQ ID NO 145
<211> LENGTH: 27
<212> TYPE: DNA
<213> ORGANISM: Artificial sequence
<220> FEATURE:
<223> OTHER INFORMATION: OsCDC48-T2-pegDel

<400> SEQUENCE: 145
tcagcggcgg cggcgccaga cgctggc 27

<210> SEQ ID NO 146
<211> LENGTH: 23
<212> TYPE: DNA
<213> ORGANISM: Artificial sequence
<220> FEATURE:
<223> OTHER INFORMATION: OsCDC48-T2-pegPBS8

<400> SEQUENCE: 146
gaccagccag cgtctggcgc cgg 23

<210> SEQ ID NO 147
<211> LENGTH: 21
<212> TYPE: DNA
<213> ORGANISM: Artificial sequence
<220> FEATURE:
<223> OTHER INFORMATION: OsCDC48-T2-pegPBS8

<400> SEQUENCE: 147
ggcgccggct ttgccagacg c 21

<210> SEQ ID NO 148
<211> LENGTH: 23
<212> TYPE: DNA
<213> ORGANISM: Artificial sequence
<220> FEATURE:
<223> OTHER INFORMATION: OsCDC48-T2-pegPBS10

<400> SEQUENCE: 148
gaccagccag cgtctggcgc cgg 23

<210> SEQ ID NO 149
<211> LENGTH: 23
<212> TYPE: DNA
<213> ORGANISM: Artificial sequence
<220> FEATURE:
<223> OTHER INFORMATION: OsCDC48-T2-pegPBS10

<400> SEQUENCE: 149
ggcgccggct ttgccagacg ctg 23

<210> SEQ ID NO 150
<211> LENGTH: 23
<212> TYPE: DNA
<213> ORGANISM: Artificial sequence
<220> FEATURE:
<223> OTHER INFORMATION: OsCDC48-T2-pegPBS14

<400> SEQUENCE: 150
gaccagccag cgtctggcgc cgg 23

<210> SEQ ID NO 151
<211> LENGTH: 27
<212> TYPE: DNA
<213> ORGANISM: Artificial sequence
<220> FEATURE:
<223> OTHER INFORMATION: OsCDC48-T2-pegPBS14

<400> SEQUENCE: 151
ggcgccggct ttgccagacg ctggctg 27

<210> SEQ ID NO 152
<211> LENGTH: 23
<212> TYPE: DNA
<213> ORGANISM: Artificial sequence
<220> FEATURE:
<223> OTHER INFORMATION: OsCDC48-T2-pegPBS16

<400> SEQUENCE: 152
gaccagccag cgtctggcgc cgg 23

<210> SEQ ID NO 153
<211> LENGTH: 29
<212> TYPE: DNA
<213> ORGANISM: Artificial sequence
<220> FEATURE:
<223> OTHER INFORMATION: OsCDC48-T2-pegPBS16

<400> SEQUENCE: 153
ggcgccggct ttgccagacg ctggctggt 29

<210> SEQ ID NO 154
<211> LENGTH: 23
<212> TYPE: DNA
<213> ORGANISM: Artificial sequence
<220> FEATURE:
<223> OTHER INFORMATION: OsCDC48-T2-pegRT10

<400> SEQUENCE: 154
gaccagccag cgtctggcgc cgg 23

<210> SEQ ID NO 155
<211> LENGTH: 22
<212> TYPE: DNA
<213> ORGANISM: Artificial sequence
<220> FEATURE:
<223> OTHER INFORMATION: OsCDC48-T2-pegRT10

<400> SEQUENCE: 155
gccggctttg ccagacgctg gc 22

<210> SEQ ID NO 156
<211> LENGTH: 23
<212> TYPE: DNA
<213> ORGANISM: Artificial sequence
<220> FEATURE:
<223> OTHER INFORMATION: OsCDC48-T2-pegRT11

<400> SEQUENCE: 156
gaccagccag cgtctggcgc cgg 23

<210> SEQ ID NO 157
<211> LENGTH: 23
<212> TYPE: DNA
<213> ORGANISM: Artificial sequence
<220> FEATURE:
<223> OTHER INFORMATION: OsCDC48-T2-pegRT11

<400> SEQUENCE: 157
cgccggcttt gccagacgct ggc 23

<210> SEQ ID NO 158
<211> LENGTH: 23
<212> TYPE: DNA
<213> ORGANISM: Artificial sequence
<220> FEATURE:
<223> OTHER INFORMATION: OsCDC48-T2-pegRT15

<400> SEQUENCE: 158
gaccagccag cgtctggcgc cgg 23

<210> SEQ ID NO 159

<400> SEQUENCE: 159

000

<210> SEQ ID NO 160
<211> LENGTH: 23
<212> TYPE: DNA
<213> ORGANISM: Artificial sequence
<220> FEATURE:
<223> OTHER INFORMATION: OsCDC48-T2-pegRT16

<400> SEQUENCE: 160
gaccagccag cgtctggcgc cgg 23

<210> SEQ ID NO 161
<211> LENGTH: 28
<212> TYPE: DNA
<213> ORGANISM: Artificial sequence
<220> FEATURE:
<223> OTHER INFORMATION: OsCDC48-T2-pegRT16

<400> SEQUENCE: 161
ggcggcgccg gctttgccag acgctggc 28

<210> SEQ ID NO 162
<211> LENGTH: 23
<212> TYPE: DNA
<213> ORGANISM: Artificial sequence
<220> FEATURE:
<223> OTHER INFORMATION: OsCDC48-T2-pegRT17

<400> SEQUENCE: 162
gaccagccag cgtctggcgc cgg 23

<210> SEQ ID NO 163
<211> LENGTH: 29
<212> TYPE: DNA
<213> ORGANISM: Artificial sequence
<220> FEATURE:
<223> OTHER INFORMATION: OsCDC48-T2-pegRT17

<400> SEQUENCE: 163
cggcggcgcc ggctttgcca gacgctggc 29

<210> SEQ ID NO 164
<211> LENGTH: 23
<212> TYPE: DNA
<213> ORGANISM: Artificial sequence
<220> FEATURE:
<223> OTHER INFORMATION: OsCDC48-T2-pegRT19

<400> SEQUENCE: 164
gaccagccag cgtctggcgc cgg 23

<210> SEQ ID NO 165
<211> LENGTH: 31
<212> TYPE: DNA
<213> ORGANISM: Artificial sequence
<220> FEATURE:
<223> OTHER INFORMATION: OsCDC48-T2-pegRT19

<400> SEQUENCE: 165
agcggcggcg ccggctttgc cagacgctgg c 31

<210> SEQ ID NO 166
<211> LENGTH: 23
<212> TYPE: DNA
<213> ORGANISM: Artificial sequence
<220> FEATURE:
<223> OTHER INFORMATION: OsCDC48-T2-pegRT21

<400> SEQUENCE: 166
gaccagccag cgtctggcgc cgg 23

<210> SEQ ID NO 167
<211> LENGTH: 33
<212> TYPE: DNA
<213> ORGANISM: Artificial sequence
<220> FEATURE:
<223> OTHER INFORMATION: OsCDC48-T2-pegRT21

<400> SEQUENCE: 167
tcagcggcgg cgccggcttt gccagacgct ggc 33

<210> SEQ ID NO 168
<211> LENGTH: 23
<212> TYPE: DNA
<213> ORGANISM: Artificial sequence
<220> FEATURE:
<223> OTHER INFORMATION: OsCDC48-T3-peg01

<400> SEQUENCE: 168
tagcacccat gacaatgaca tgg 23

<210> SEQ ID NO 169
<211> LENGTH: 27
<212> TYPE: DNA
<213> ORGANISM: Artificial sequence
<220> FEATURE:
<223> OTHER INFORMATION: OsCDC48-T3-peg01

<400> SEQUENCE: 169
agctcgttcc cgggtcattg tcatggg 27

<210> SEQ ID NO 170
<211> LENGTH: 23
<212> TYPE: DNA
<213> ORGANISM: Artificial sequence
<220> FEATURE:
<223> OTHER INFORMATION: OsDEP1-peg01

<400> SEQUENCE: 170
gtgggtttgt ttctagctca agg 23

<210> SEQ ID NO 171
<211> LENGTH: 26

<212> TYPE: DNA
<213> ORGANISM: Artificial sequence
<220> FEATURE:
<223> OTHER INFORMATION: OsDEP1-peg01

<400> SEQUENCE: 171
atttcctcct taagctagaa acaaac 26

<210> SEQ ID NO 172
<211> LENGTH: 23
<212> TYPE: DNA
<213> ORGANISM: Artificial sequence
<220> FEATURE:
<223> OTHER INFORMATION: OsDEP1-peg02

<400> SEQUENCE: 172
gtgggtttgt ttctagctca agg 23

<210> SEQ ID NO 173
<211> LENGTH: 26
<212> TYPE: DNA
<213> ORGANISM: Artificial sequence
<220> FEATURE:
<223> OTHER INFORMATION: OsDEP1-peg02

<400> SEQUENCE: 173
atttcctcct cgagctagaa acaaac 26

<210> SEQ ID NO 174
<211> LENGTH: 23
<212> TYPE: DNA
<213> ORGANISM: Artificial sequence
<220> FEATURE:
<223> OTHER INFORMATION: OsEPSPS-T1-peg01

<400> SEQUENCE: 174
tactaaatat acaatccctt ggg 23

<210> SEQ ID NO 175
<211> LENGTH: 24
<212> TYPE: DNA
<213> ORGANISM: Artificial sequence
<220> FEATURE:
<223> OTHER INFORMATION: OsEPSPS-T1-peg01

<400> SEQUENCE: 175
ataaacccat gggattgtat attt 24

<210> SEQ ID NO 176
<211> LENGTH: 23
<212> TYPE: DNA
<213> ORGANISM: Artificial sequence
<220> FEATURE:
<223> OTHER INFORMATION: OsEPSPS-T1-peg02

<400> SEQUENCE: 176
tactaaatat acaatccctt ggg 23

<210> SEQ ID NO 177
<211> LENGTH: 33
<212> TYPE: DNA
<213> ORGANISM: Artificial sequence
<220> FEATURE:
<223> OTHER INFORMATION: OsEPSPS-T1-peg02

<400> SEQUENCE: 177
tggaaacaaa taaacacaag ggattgtata ttt 33

<210> SEQ ID NO 178
<211> LENGTH: 23
<212> TYPE: DNA
<213> ORGANISM: Artificial sequence
<220> FEATURE:
<223> OTHER INFORMATION: OsEPSPS-T2-peg01

<400> SEQUENCE: 178
gaaaatatgt atggaattca tgg 23

<210> SEQ ID NO 179
<211> LENGTH: 31
<212> TYPE: DNA
<213> ORGANISM: Artificial sequence
<220> FEATURE:
<223> OTHER INFORMATION: OsEPSPS-T2-peg01

<400> SEQUENCE: 179
ataaaacata ccccattaat tccatacata t 31

<210> SEQ ID NO 180
<211> LENGTH: 23
<212> TYPE: DNA
<213> ORGANISM: Artificial sequence
<220> FEATURE:
<223> OTHER INFORMATION: OsGAPDH-peg01

<400> SEQUENCE: 180
gagtatgtcg tggagtccac cgg 23

<210> SEQ ID NO 181
<211> LENGTH: 28
<212> TYPE: DNA
<213> ORGANISM: Artificial sequence
<220> FEATURE:
<223> OTHER INFORMATION: OsGAPDH-peg01

<400> SEQUENCE: 181
agtgaagaca ccgttggact ccacgaca 28

<210> SEQ ID NO 182
<211> LENGTH: 23
<212> TYPE: DNA
<213> ORGANISM: Artificial sequence
<220> FEATURE:
<223> OTHER INFORMATION: OsGAPDH-pegCT

<400> SEQUENCE: 182
gagtatgtcg tggagtccac cgg 23

<210> SEQ ID NO 183
<211> LENGTH: 28
<212> TYPE: DNA
<213> ORGANISM: Artificial sequence
<220> FEATURE:
<223> OTHER INFORMATION: OsGAPDH-pegCT

<400> SEQUENCE: 183
agtgaagaca ccgatggact ccacgaca 28

<210> SEQ ID NO 184
<211> LENGTH: 23
<212> TYPE: DNA
<213> ORGANISM: Artificial sequence
<220> FEATURE:
<223> OTHER INFORMATION: OsGAPDH-pegCG

<400> SEQUENCE: 184
gagtatgtcg tggagtccac cgg 23

<210> SEQ ID NO 185
<211> LENGTH: 28
<212> TYPE: DNA
<213> ORGANISM: Artificial sequence
<220> FEATURE:
<223> OTHER INFORMATION: OsGAPDH-pegCG

<400> SEQUENCE: 185
agtgaagaca ccgctggact ccacgaca 28

<210> SEQ ID NO 186
<211> LENGTH: 23
<212> TYPE: DNA
<213> ORGANISM: Artificial sequence
<220> FEATURE:
<223> OTHER INFORMATION: OsGAPDH-pegAT

<400> SEQUENCE: 186
gagtatgtcg tggagtccac cgg 23

<210> SEQ ID NO 187
<211> LENGTH: 28
<212> TYPE: DNA
<213> ORGANISM: Artificial sequence
<220> FEATURE:
<223> OTHER INFORMATION: OsGAPDH-pegAT

<400> SEQUENCE: 187
agtgaagaca ccggaggact ccacgaca 28

<210> SEQ ID NO 188
<211> LENGTH: 23
<212> TYPE: DNA
<213> ORGANISM: Artificial sequence
<220> FEATURE:
<223> OTHER INFORMATION: OsGAPDH-pegAC

<400> SEQUENCE: 188
gagtatgtcg tggagtccac cgg 23

<210> SEQ ID NO 189
<211> LENGTH: 28
<212> TYPE: DNA
<213> ORGANISM: Artificial sequence
<220> FEATURE:
<223> OTHER INFORMATION: OsGAPDH-pegAC

<400> SEQUENCE: 189
agtgaagaca ccgggggact ccacgaca 28

<210> SEQ ID NO 190
<211> LENGTH: 23
<212> TYPE: DNA
<213> ORGANISM: Artificial sequence
<220> FEATURE:
<223> OTHER INFORMATION: OsGAPDH-pegAG

<400> SEQUENCE: 190
gagtatgtcg tggagtccac cgg 23

<210> SEQ ID NO 191
<211> LENGTH: 28
<212> TYPE: DNA
<213> ORGANISM: Artificial sequence
<220> FEATURE:
<223> OTHER INFORMATION: OsGAPDH-pegAG

<400> SEQUENCE: 191
agtgaagaca ccggcggact ccacgaca 28

<210> SEQ ID NO 192
<211> LENGTH: 23
<212> TYPE: DNA
<213> ORGANISM: Artificial sequence
<220> FEATURE:
<223> OTHER INFORMATION: OsGAPDH-pegGA

<400> SEQUENCE: 192
gagtatgtcg tggagtccac cgg 23

<210> SEQ ID NO 193
<211> LENGTH: 28
<212> TYPE: DNA
<213> ORGANISM: Artificial sequence
<220> FEATURE:
<223> OTHER INFORMATION: OsGAPDH-pegGA

<400> SEQUENCE: 193
agtgaagaca ctggtggact ccacgaca 28

<210> SEQ ID NO 194
<211> LENGTH: 23
<212> TYPE: DNA
<213> ORGANISM: Artificial sequence
<220> FEATURE:
<223> OTHER INFORMATION: OsGAPDH-pegGT

<400> SEQUENCE: 194
gagtatgtcg tggagtccac cgg 23

<210> SEQ ID NO 195
<211> LENGTH: 28
<212> TYPE: DNA
<213> ORGANISM: Artificial sequence
<220> FEATURE:
<223> OTHER INFORMATION: OsGAPDH-pegGT

<400> SEQUENCE: 195
agtgaagaca caggtggact ccacgaca 28

<210> SEQ ID NO 196
<211> LENGTH: 23
<212> TYPE: DNA
<213> ORGANISM: Artificial sequence
<220> FEATURE:
<223> OTHER INFORMATION: OsGAPDH-pegGC

<400> SEQUENCE: 196
gagtatgtcg tggagtccac cgg 23

<210> SEQ ID NO 197
<211> LENGTH: 28
<212> TYPE: DNA
<213> ORGANISM: Artificial sequence
<220> FEATURE:
<223> OTHER INFORMATION: OsGAPDH-pegGC

<400> SEQUENCE: 197
agtgaagaca caggtggact ccacgaca 28

<210> SEQ ID NO 198
<211> LENGTH: 23
<212> TYPE: DNA
<213> ORGANISM: Artificial sequence
<220> FEATURE:
<223> OTHER INFORMATION: OsGAPDH-pegTA

<400> SEQUENCE: 198
gagtatgtcg tggagtccac cgg 23

<210> SEQ ID NO 199
<211> LENGTH: 28
<212> TYPE: DNA
<213> ORGANISM: Artificial sequence
<220> FEATURE:
<223> OTHER INFORMATION: OsGAPDH-pegTA

<400> SEQUENCE: 199
agtgaagact ccggtggact ccacgaca 28

<210> SEQ ID NO 200
<211> LENGTH: 23
<212> TYPE: DNA
<213> ORGANISM: Artificial sequence
<220> FEATURE:
<223> OTHER INFORMATION: OsGAPDH-pegTC

<400> SEQUENCE: 200
gagtatgtcg tggagtccac cgg 23

<210> SEQ ID NO 201
<211> LENGTH: 28
<212> TYPE: DNA
<213> ORGANISM: Artificial sequence
<220> FEATURE:
<223> OTHER INFORMATION: OsGAPDH-pegTC

<400> SEQUENCE: 201
agtgaagacg ccggtggact ccacgaca 28

<210> SEQ ID NO 202
<211> LENGTH: 23
<212> TYPE: DNA
<213> ORGANISM: Artificial sequence
<220> FEATURE:
<223> OTHER INFORMATION: OsGAPDH-pegTG

<400> SEQUENCE: 202
gagtatgtcg tggagtccac cgg 23

<210> SEQ ID NO 203
<211> LENGTH: 28
<212> TYPE: DNA
<213> ORGANISM: Artificial sequence
<220> FEATURE:
<223> OTHER INFORMATION: OsGAPDH-pegTG

<400> SEQUENCE: 203
agtgaagacc ccggtggact ccacgaca 28

<210> SEQ ID NO 204

<211> LENGTH: 23
<212> TYPE: DNA
<213> ORGANISM: Artificial sequence
<220> FEATURE:
<223> OTHER INFORMATION: OsLDMAR-peg01

<400> SEQUENCE: 204
gtgcatcctg ggaaagcttg tgg 23

<210> SEQ ID NO 205
<211> LENGTH: 28
<212> TYPE: DNA
<213> ORGANISM: Artificial sequence
<220> FEATURE:
<223> OTHER INFORMATION: OsLDMAR-peg01

<400> SEQUENCE: 205
aaacttgcta ccactagctt tcccagga 28

<210> SEQ ID NO 206
<211> LENGTH: 23
<212> TYPE: DNA
<213> ORGANISM: Artificial sequence
<220> FEATURE:
<223> OTHER INFORMATION: TaGW2-peg01

<400> SEQUENCE: 206
cacaagaaaa tccaccagga tgg 23

<210> SEQ ID NO 207
<211> LENGTH: 22
<212> TYPE: DNA
<213> ORGANISM: Artificial sequence
<220> FEATURE:
<223> OTHER INFORMATION: TaGW2-peg01

<400> SEQUENCE: 207
atgccccatc gtggtggatt tt 22

<210> SEQ ID NO 208

<400> SEQUENCE: 208

000

<210> SEQ ID NO 209
<211> LENGTH: 29
<212> TYPE: DNA
<213> ORGANISM: Artificial sequence
<220> FEATURE:
<223> OTHER INFORMATION: TaUbi10-T1-peg01

<400> SEQUENCE: 209
agaaaaggct ccagtacagt ttcatacat 29

<210> SEQ ID NO 210
<211> LENGTH: 23
<212> TYPE: DNA
<213> ORGANISM: Artificial sequence
<220> FEATURE:
<223> OTHER INFORMATION: TaUbi10-T2-peg01

<400> SEQUENCE: 210
gctggtgcaa ctggtggccc agg 23

<210> SEQ ID NO 211

<211> LENGTH: 24
<212> TYPE: DNA
<213> ORGANISM: Artificial sequence
<220> FEATURE:
<223> OTHER INFORMATION: TaUbi10-T2-peg01

<400> SEQUENCE: 211
agccctcctg gcccaccagt tgca 24

<210> SEQ ID NO 212
<211> LENGTH: 23
<212> TYPE: DNA
<213> ORGANISM: Artificial sequence
<220> FEATURE:
<223> OTHER INFORMATION: TaLOX2-peg01

<400> SEQUENCE: 212
gtgccgcgcg acgagctctt cgg 23

<210> SEQ ID NO 213
<211> LENGTH: 26
<212> TYPE: DNA
<213> ORGANISM: Artificial sequence
<220> FEATURE:
<223> OTHER INFORMATION: TaLOX2-peg01

<400> SEQUENCE: 213
tgaggtggcc gaacagctcg tcgcgc 26

<210> SEQ ID NO 214
<211> LENGTH: 23
<212> TYPE: DNA
<213> ORGANISM: Artificial sequence
<220> FEATURE:
<223> OTHER INFORMATION: TaMLO-peg01

<400> SEQUENCE: 214
ggagattggg tcctgcgtga cgg 23

<210> SEQ ID NO 215

<400> SEQUENCE: 215

000

<210> SEQ ID NO 216
<211> LENGTH: 23
<212> TYPE: DNA
<213> ORGANISM: Artificial sequence
<220> FEATURE:
<223> OTHER INFORMATION: TaDME- peg01

<400> SEQUENCE: 216
tttgatggtt tcaggacctt tgg 23

<210> SEQ ID NO 217
<211> LENGTH: 27
<212> TYPE: DNA
<213> ORGANISM: Artificial sequence
<220> FEATURE:
<223> OTHER INFORMATION: TaDME- peg01

<400> SEQUENCE: 217
agcacaggcc aaatgtcctg aaaccat 27

<210> SEQ ID NO 218

<211> LENGTH: 23
<212> TYPE: DNA
<213> ORGANISM: Artificial sequence
<220> FEATURE:
<223> OTHER INFORMATION: TaGASR7-peg01

<400> SEQUENCE: 218
gccgggcacc tacggcaaca agg 23

<210> SEQ ID NO 219
<211> LENGTH: 30
<212> TYPE: DNA
<213> ORGANISM: Artificial sequence
<220> FEATURE:
<223> OTHER INFORMATION: TaGASR7-peg01

<400> SEQUENCE: 219
aggggcaggc gcgcttgttg ccgtaggtgc 30

<210> SEQ ID NO 220
<211> LENGTH: 23
<212> TYPE: DNA
<213> ORGANISM: Artificial sequence
<220> FEATURE:
<223> OTHER INFORMATION: OsCDC48 (I)

<400> SEQUENCE: 220
gaccagccag cgtctggcgc cgg 23

<210> SEQ ID NO 221
<211> LENGTH: 30
<212> TYPE: DNA
<213> ORGANISM: Artificial sequence
<220> FEATURE:
<223> OTHER INFORMATION: OsCDC48 (I)

<400> SEQUENCE: 221
tcagcggcgg cgcctgcgcc agacgctggc 30

<210> SEQ ID NO 222
<211> LENGTH: 23
<212> TYPE: DNA
<213> ORGANISM: Artificial sequence
<220> FEATURE:
<223> OTHER INFORMATION: OsCDC48 (II)

<400> SEQUENCE: 222
ccggcgccag acgctggctg gtc 23

<210> SEQ ID NO 223
<211> LENGTH: 30
<212> TYPE: DNA
<213> ORGANISM: Artificial sequence
<220> FEATURE:
<223> OTHER INFORMATION: OsCDC48 (II)

<400> SEQUENCE: 223
cagcgtctgg cgcaggcgcc gccgctgacc 30

<210> SEQ ID NO 224
<211> LENGTH: 23
<212> TYPE: DNA
<213> ORGANISM: Artificial sequence
<220> FEATURE:
<223> OTHER INFORMATION: OsCDC48 (III)

<400> SEQUENCE: 224
gaccagccag cgtctggcgc cgg 23

<210> SEQ ID NO 225
<211> LENGTH: 30
<212> TYPE: DNA
<213> ORGANISM: Artificial sequence
<220> FEATURE:
<223> OTHER INFORMATION: OsCDC48 (III)

<400> SEQUENCE: 225
tcagcggcgg cgctggcgcc agacgctggc 30

<210> SEQ ID NO 226
<211> LENGTH: 23
<212> TYPE: DNA
<213> ORGANISM: Artificial sequence
<220> FEATURE:
<223> OTHER INFORMATION: OsCDC48 (IV)

<400> SEQUENCE: 226
ccggcgccag acgctggctg gtc 23

<210> SEQ ID NO 227
<211> LENGTH: 30
<212> TYPE: DNA
<213> ORGANISM: Artificial sequence
<220> FEATURE:
<223> OTHER INFORMATION: OsCDC48 (IV)

<400> SEQUENCE: 227
cagcgtctgg cgccagcgcc gccgctgacc 30

<210> SEQ ID NO 228
<211> LENGTH: 23
<212> TYPE: DNA
<213> ORGANISM: Artificial sequence
<220> FEATURE:
<223> OTHER INFORMATION: OsALS (I)

<400> SEQUENCE: 228
gtgctgccta tgatcccaag tgg 23

<210> SEQ ID NO 229
<211> LENGTH: 27
<212> TYPE: DNA
<213> ORGANISM: Artificial sequence
<220> FEATURE:
<223> OTHER INFORMATION: OsALS (I)

<400> SEQUENCE: 229
tgaatgcgcc cccaattggg atcatag 27

<210> SEQ ID NO 230

<400> SEQUENCE: 230

000

<210> SEQ ID NO 231
<211> LENGTH: 27
<212> TYPE: DNA
<213> ORGANISM: Artificial sequence
<220> FEATURE:
<223> OTHER INFORMATION: OsALS (II)

<400> SEQUENCE: 231
tgcctatgat cccaattggg ggcgcat 27

<210> SEQ ID NO 232
<211> LENGTH: 23
<212> TYPE: DNA
<213> ORGANISM: Artificial sequence
<220> FEATURE:
<223> OTHER INFORMATION: OsALS (III)

<400> SEQUENCE: 232
gtgctgccta tgatcccaag tgg 23

<210> SEQ ID NO 233
<211> LENGTH: 27
<212> TYPE: DNA
<213> ORGANISM: Artificial sequence
<220> FEATURE:
<223> OTHER INFORMATION: OsALS (III)

<400> SEQUENCE: 233
tgaatgcgcc cccacctggg atcatag 27

<210> SEQ ID NO 234
<211> LENGTH: 23
<212> TYPE: DNA
<213> ORGANISM: Artificial sequence
<220> FEATURE:
<223> OTHER INFORMATION: OsALS (IV)

<400> SEQUENCE: 234
ccaagtgggg gcgcattcaa gga 23

<210> SEQ ID NO 235
<211> LENGTH: 27
<212> TYPE: DNA
<213> ORGANISM: Artificial sequence
<220> FEATURE:
<223> OTHER INFORMATION: OsALS (IV)

<400> SEQUENCE: 235
tgcctatgat cccaggtggg ggcgcat 27

<210> SEQ ID NO 236
<211> LENGTH: 23
<212> TYPE: DNA
<213> ORGANISM: Artificial sequence
<220> FEATURE:
<223> OTHER INFORMATION: OsEPSPS (I)

<400> SEQUENCE: 236
tactaaatat acaatccctt ggg 23

<210> SEQ ID NO 237
<211> LENGTH: 24
<212> TYPE: DNA
<213> ORGANISM: Artificial sequence
<220> FEATURE:
<223> OTHER INFORMATION: OsEPSPS (I)

<400> SEQUENCE: 237
ataaacccat gggattgtat attt 24

<210> SEQ ID NO 238
<211> LENGTH: 23
<212> TYPE: DNA

<213> ORGANISM: Artificial sequence
<220> FEATURE:
<223> OTHER INFORMATION: OsEPSPS (II)

<400> SEQUENCE: 238
cccttgggtt tatttgtttc caa 23

<210> SEQ ID NO 239
<211> LENGTH: 24
<212> TYPE: DNA
<213> ORGANISM: Artificial sequence
<220> FEATURE:
<223> OTHER INFORMATION: OsEPSPS (II)

<400> SEQUENCE: 239
acaatcccat gggtttattt gttt 24

<210> SEQ ID NO 240

<400> SEQUENCE: 240

000

<210> SEQ ID NO 241
<211> LENGTH: 31
<212> TYPE: DNA
<213> ORGANISM: Artificial sequence
<220> FEATURE:
<223> OTHER INFORMATION: OsEPSPS (III)

<400> SEQUENCE: 241
tgcaaactgg tagtaccaca accttgaact g 31

<210> SEQ ID NO 242
<211> LENGTH: 23
<212> TYPE: DNA
<213> ORGANISM: Artificial sequence
<220> FEATURE:
<223> OTHER INFORMATION: OsEPSPS (IV)

<400> SEQUENCE: 242
ccagtttgca ggtataactg tag 23

<210> SEQ ID NO 243

<400> SEQUENCE: 243

000

<210> SEQ ID NO 244
<211> LENGTH: 23
<212> TYPE: DNA
<213> ORGANISM: Artificial sequence
<220> FEATURE:
<223> OTHER INFORMATION: OsIPA1 (I)

<400> SEQUENCE: 244
ctcttctgtc aacccagcca tgg 23

<210> SEQ ID NO 245
<211> LENGTH: 22
<212> TYPE: DNA
<213> ORGANISM: Artificial sequence
<220> FEATURE:
<223> OTHER INFORMATION: OsIPA1 (I)

<400> SEQUENCE: 245
agtatcccat gcctgggttg ac 22

<210> SEQ ID NO 246
<211> LENGTH: 23
<212> TYPE: DNA
<213> ORGANISM: Artificial sequence
<220> FEATURE:
<223> OTHER INFORMATION: OsIPA1 (II)

<400> SEQUENCE: 246
cccagccatg ggatactact acc 23

<210> SEQ ID NO 247
<211> LENGTH: 22
<212> TYPE: DNA
<213> ORGANISM: Artificial sequence
<220> FEATURE:
<223> OTHER INFORMATION: OsIPA1 (II)

<400> SEQUENCE: 247
tgtcaaccca ggcatgggat ac 22

<210> SEQ ID NO 248
<211> LENGTH: 23
<212> TYPE: DNA
<213> ORGANISM: Artificial sequence
<220> FEATURE:
<223> OTHER INFORMATION: OsIPA1 (III)

<400> SEQUENCE: 248
tcttctgtca acccagccat tgg 23

<210> SEQ ID NO 249
<211> LENGTH: 28
<212> TYPE: DNA
<213> ORGANISM: Artificial sequence
<220> FEATURE:
<223> OTHER INFORMATION: OsIPA1 (III)

<400> SEQUENCE: 249
gtagtatcgc atggctgggt tgacagaa 28

<210> SEQ ID NO 250
<211> LENGTH: 23
<212> TYPE: DNA
<213> ORGANISM: Artificial sequence
<220> FEATURE:
<223> OTHER INFORMATION: OsIPA1 (IV)

<400> SEQUENCE: 250
ccatgggata ctactaccca cag 23

<210> SEQ ID NO 251
<211> LENGTH: 28
<212> TYPE: DNA
<213> ORGANISM: Artificial sequence
<220> FEATURE:
<223> OTHER INFORMATION: OsIPA1 (IV)

<400> SEQUENCE: 251
aacccagcca tgcgatacta ctacccac 28

<210> SEQ ID NO 252
<211> LENGTH: 23
<212> TYPE: DNA

<213> ORGANISM: Artificial sequence
<220> FEATURE:
<223> OTHER INFORMATION: OsROC5 (I)

<400> SEQUENCE: 252
tctcacctct agtaccaatt agg 23

<210> SEQ ID NO 253
<211> LENGTH: 27
<212> TYPE: DNA
<213> ORGANISM: Artificial sequence
<220> FEATURE:
<223> OTHER INFORMATION: OsROC5 (I)

<400> SEQUENCE: 253
tgtaacctcc ctatggtact agaggtg 27

<210> SEQ ID NO 254
<211> LENGTH: 23
<212> TYPE: DNA
<213> ORGANISM: Artificial sequence
<220> FEATURE:
<223> OTHER INFORMATION: OsROC5 (II)

<400> SEQUENCE: 254
ccaattaggg aggttacatt tct 23

<210> SEQ ID NO 255
<211> LENGTH: 27
<212> TYPE: DNA
<213> ORGANISM: Artificial sequence
<220> FEATURE:
<223> OTHER INFORMATION: OsROC5 (II)

<400> SEQUENCE: 255
cctctagtac catagggagg ttacatt 27

<210> SEQ ID NO 256
<211> LENGTH: 23
<212> TYPE: DNA
<213> ORGANISM: Artificial sequence
<220> FEATURE:
<223> OTHER INFORMATION: OsDEP1 (I)

<400> SEQUENCE: 256
gagacaagct tggccctctt tgg 23

<210> SEQ ID NO 257
<211> LENGTH: 25
<212> TYPE: DNA
<213> ORGANISM: Artificial sequence
<220> FEATURE:
<223> OTHER INFORMATION: OsDEP1 (I)

<400> SEQUENCE: 257
cgccacgccc aagagggcca agctt 25

<210> SEQ ID NO 258
<211> LENGTH: 23
<212> TYPE: DNA
<213> ORGANISM: Artificial sequence
<220> FEATURE:
<223> OTHER INFORMATION: OsDEP1 (II)

<400> SEQUENCE: 258
cctctttggg cgtggcgcca tgg 23

<210> SEQ ID NO 259
<211> LENGTH: 25
<212> TYPE: DNA
<213> ORGANISM: Artificial sequence
<220> FEATURE:
<223> OTHER INFORMATION: OsDEP1 (II)

<400> SEQUENCE: 259
agcttggccc tcttgggcgt ggcgc 25

<210> SEQ ID NO 260
<211> LENGTH: 23
<212> TYPE: DNA
<213> ORGANISM: Artificial sequence
<220> FEATURE:
<223> OTHER INFORMATION: OsDEP1 (III)

<400> SEQUENCE: 260
agcttggccc tctttgggcg tgg 23

<210> SEQ ID NO 261
<211> LENGTH: 28
<212> TYPE: DNA
<213> ORGANISM: Artificial sequence
<220> FEATURE:
<223> OTHER INFORMATION: OsDEP1 (III)

<400> SEQUENCE: 261
acagccatgg ctccacgccc aaagaggg 28

<210> SEQ ID NO 262
<211> LENGTH: 23
<212> TYPE: DNA
<213> ORGANISM: Artificial sequence
<220> FEATURE:
<223> OTHER INFORMATION: OsDEP1 (IV)

<400> SEQUENCE: 262
ccatggctgt actacctttg tcg 23

<210> SEQ ID NO 263
<211> LENGTH: 28
<212> TYPE: DNA
<213> ORGANISM: Artificial sequence
<220> FEATURE:
<223> OTHER INFORMATION: OsDEP1 (IV)

<400> SEQUENCE: 263
ttgggcgtgg agccatggct gtactacc 28

<210> SEQ ID NO 264
<211> LENGTH: 23
<212> TYPE: DNA
<213> ORGANISM: Artificial sequence
<220> FEATURE:
<223> OTHER INFORMATION: OsNRT1.1B (I)

<400> SEQUENCE: 264
actagatatc taaaccatta agg 23

<210> SEQ ID NO 265
<211> LENGTH: 30
<212> TYPE: DNA
<213> ORGANISM: Artificial sequence
<220> FEATURE:

<223> OTHER INFORMATION: OsNRT1.1B (I)

<400> SEQUENCE: 265
atttgaccta cctttaatgg tttagatatc 30

<210> SEQ ID NO 266
<211> LENGTH: 23
<212> TYPE: DNA
<213> ORGANISM: Artificial sequence
<220> FEATURE:
<223> OTHER INFORMATION: OsNRT1.1B (II)

<400> SEQUENCE: 266
ccattaaggt aggtcaaatc aag 23

<210> SEQ ID NO 267
<211> LENGTH: 30
<212> TYPE: DNA
<213> ORGANISM: Artificial sequence
<220> FEATURE:
<223> OTHER INFORMATION: OsNRT1.1B (II)

<400> SEQUENCE: 267
gatatctaaa ccattaaagg taggtcaaat 30

<210> SEQ ID NO 268
<211> LENGTH: 23
<212> TYPE: DNA
<213> ORGANISM: Artificial sequence
<220> FEATURE:
<223> OTHER INFORMATION: OsNRT1.1B (III)

<400> SEQUENCE: 268
cctgtaggtg tgtatatact tgg 23

<210> SEQ ID NO 269
<211> LENGTH: 27
<212> TYPE: DNA
<213> ORGANISM: Artificial sequence
<220> FEATURE:
<223> OTHER INFORMATION: OsNRT1.1B (III)

<400> SEQUENCE: 269
tagtgctggt tcaagtatat acacacc 27

<210> SEQ ID NO 270
<211> LENGTH: 23
<212> TYPE: DNA
<213> ORGANISM: Artificial sequence
<220> FEATURE:
<223> OTHER INFORMATION: OsNRT1.1B (IV)

<400> SEQUENCE: 270
ccagcactac tagatatcta aac 23

<210> SEQ ID NO 271
<211> LENGTH: 27
<212> TYPE: DNA
<213> ORGANISM: Artificial sequence
<220> FEATURE:
<223> OTHER INFORMATION: OsNRT1.1B (IV)

<400> SEQUENCE: 271
tatacttgaa ccagcactac tagatat 27

<210> SEQ ID NO 272
<211> LENGTH: 23
<212> TYPE: DNA
<213> ORGANISM: Artificial sequence
<220> FEATURE:
<223> OTHER INFORMATION: OsODEV (I)

<400> SEQUENCE: 272
cacacacaca ctagtacctc tgg 23

<210> SEQ ID NO 273
<211> LENGTH: 25
<212> TYPE: DNA
<213> ORGANISM: Artificial sequence
<220> FEATURE:
<223> OTHER INFORMATION: OsODEV (I)

<400> SEQUENCE: 273
aatagtcccc taggtactag tgtgt 25

<210> SEQ ID NO 274
<211> LENGTH: 23
<212> TYPE: DNA
<213> ORGANISM: Artificial sequence
<220> FEATURE:
<223> OTHER INFORMATION: OsODEV (II)

<400> SEQUENCE: 274
cctctgggac tattgtgtgt gtc 23

<210> SEQ ID NO 275
<211> LENGTH: 25
<212> TYPE: DNA
<213> ORGANISM: Artificial sequence
<220> FEATURE:
<223> OTHER INFORMATION: OsODEV (II)

<400> SEQUENCE: 275
actagtacct aggggactat tgtgt 25

<210> SEQ ID NO 276
<211> LENGTH: 23
<212> TYPE: DNA
<213> ORGANISM: Artificial sequence
<220> FEATURE:
<223> OTHER INFORMATION: OsGAPDH (I)

<400> SEQUENCE: 276
gagtatgtcg tggagtccac cgg 23

<210> SEQ ID NO 277
<211> LENGTH: 28
<212> TYPE: DNA
<213> ORGANISM: Artificial sequence
<220> FEATURE:
<223> OTHER INFORMATION: OsGAPDH (I)

<400> SEQUENCE: 277
agtgaagaca ccgctggact ccacgaca 28

<210> SEQ ID NO 278
<211> LENGTH: 23
<212> TYPE: DNA
<213> ORGANISM: Artificial sequence
<220> FEATURE:
<223> OTHER INFORMATION: OsGAPDH (II)

<400> SEQUENCE: 278
ccaccggtgt cttcactgac aag 23

<210> SEQ ID NO 279
<211> LENGTH: 28
<212> TYPE: DNA
<213> ORGANISM: Artificial sequence
<220> FEATURE:
<223> OTHER INFORMATION: OsGAPDH (II)

<400> SEQUENCE: 279
gtcgtggagt ccagcggtgt cttcactg 28

<210> SEQ ID NO 280
<211> LENGTH: 33
<212> TYPE: DNA
<213> ORGANISM: Artificial sequence
<220> FEATURE:
<223> OTHER INFORMATION: BFP-to-GFP reporter system, target sequence

<400> SEQUENCE: 280
ctcgtgacca ccttcaccca cggcgtgcag tgc 33

<210> SEQ ID NO 281
<211> LENGTH: 33
<212> TYPE: DNA
<213> ORGANISM: Artificial sequence
<220> FEATURE:
<223> OTHER INFORMATION: BFP-to-GFP reporter system, target sequence

<400> SEQUENCE: 281
gagcactggt ggaagtgggt gccgcacgtc acg 33

<210> SEQ ID NO 282
<211> LENGTH: 33
<212> TYPE: DNA
<213> ORGANISM: Artificial sequence
<220> FEATURE:
<223> OTHER INFORMATION: BFP-to-GFP reporter system, Intermediate
sequence

<400> SEQUENCE: 282
ctcgtgacca ccttcacgta cggcgtgcag tgc 33

<210> SEQ ID NO 283
<211> LENGTH: 33
<212> TYPE: DNA
<213> ORGANISM: Artificial sequence
<220> FEATURE:
<223> OTHER INFORMATION: BFP-to-GFP reporter system, Intermediate
sequence

<400> SEQUENCE: 283
gagcactggt ggaagtgggt gccgcacgtc acg 33

<210> SEQ ID NO 284
<211> LENGTH: 33
<212> TYPE: DNA
<213> ORGANISM: Artificial sequence
<220> FEATURE:
<223> OTHER INFORMATION: BFP-to-GFP reporter system, obtained sequence

<400> SEQUENCE: 284
ctcgtgacca ccttcacgta cggcgtgcag tgc 33

<210> SEQ ID NO 285
<211> LENGTH: 33
<212> TYPE: DNA
<213> ORGANISM: Artificial sequence
<220> FEATURE:
<223> OTHER INFORMATION: BFP-to-GFP reporter system, obtained sequence

<400> SEQUENCE: 285
gagcactggt ggaagtgcat gccgcacgtc acg 33

<210> SEQ ID NO 286
<211> LENGTH: 26
<212> TYPE: DNA
<213> ORGANISM: Artificial sequence
<220> FEATURE:
<223> OTHER INFORMATION: OsCDC48-T1, unedited sequence

<400> SEQUENCE: 286
taatctccgg gccattaatc agaaag 26

<210> SEQ ID NO 287
<211> LENGTH: 20
<212> TYPE: DNA
<213> ORGANISM: Artificial sequence
<220> FEATURE:
<223> OTHER INFORMATION: OsCDC48-T1, Precisely edited sequence

<400> SEQUENCE: 287
taatgccatt aatcagaaag 20

<210> SEQ ID NO 288
<211> LENGTH: 20
<212> TYPE: DNA
<213> ORGANISM: Artificial sequence
<220> FEATURE:
<223> OTHER INFORMATION: OsCDC48-T1, edit with byproduct

<400> SEQUENCE: 288
taatgccatt aatgagaaag 20

<210> SEQ ID NO 289
<211> LENGTH: 20
<212> TYPE: DNA
<213> ORGANISM: Artificial sequence
<220> FEATURE:
<223> OTHER INFORMATION: OsCDC48-T1, edit with byproduct

<400> SEQUENCE: 289
taatgccatt aatgcgaaag 20

<210> SEQ ID NO 290
<211> LENGTH: 21
<212> TYPE: DNA
<213> ORGANISM: Artificial sequence
<220> FEATURE:
<223> OTHER INFORMATION: OsCDC48-T1, edit with byproduct

<400> SEQUENCE: 290
taatgccatt aatgcagaaa g 21

<210> SEQ ID NO 291
<211> LENGTH: 20
<212> TYPE: DNA
<213> ORGANISM: Artificial sequence
<220> FEATURE:
<223> OTHER INFORMATION: OsCDC48-T1, edit with byproduct

<400> SEQUENCE: 291
taatgccatt aatgcaccag 20

<210> SEQ ID NO 292
<211> LENGTH: 20
<212> TYPE: DNA
<213> ORGANISM: Artificial sequence
<220> FEATURE:
<223> OTHER INFORMATION: OsCDC48-T1, edit with byproduct

<400> SEQUENCE: 292
taaggccatt aatcagaaag 20

<210> SEQ ID NO 293
<211> LENGTH: 50
<212> TYPE: DNA
<213> ORGANISM: Artificial sequence
<220> FEATURE:
<223> OTHER INFORMATION: OsCDC48-T2, unedited sequence
<220> FEATURE:
<221> NAME/KEY: misc_feature
<222> LOCATION: (25)..(39)
<223> OTHER INFORMATION: n is a, c, g, or t

<400> SEQUENCE: 293
tggcgccggc gccgccgctg acccnnnnnn nnnnnnnnnc gccgcagctg 50

<210> SEQ ID NO 294
<211> LENGTH: 50
<212> TYPE: DNA
<213> ORGANISM: Artificial sequence
<220> FEATURE:
<223> OTHER INFORMATION: OsCDC48-T2, Precisely edited sequence
<220> FEATURE:
<221> NAME/KEY: misc_feature
<222> LOCATION: (25)..(39)
<223> OTHER INFORMATION: n is a, c, g, or t

<400> SEQUENCE: 294
tggcgccagc gccgccgctg acccnnnnnn nnnnnnnnnc gccgcagctg 50

<210> SEQ ID NO 295
<211> LENGTH: 50
<212> TYPE: DNA
<213> ORGANISM: Artificial sequence
<220> FEATURE:
<223> OTHER INFORMATION: OsCDC48-T2, edit with byproduct
<220> FEATURE:
<221> NAME/KEY: misc_feature
<222> LOCATION: (25)..(39)
<223> OTHER INFORMATION: n is a, c, g, or t

<400> SEQUENCE: 295
tggcgccggc gccgccgctg agccnnnnnn nnnnnnnnnc gccgcagctg 50

<210> SEQ ID NO 296
<211> LENGTH: 50
<212> TYPE: DNA
<213> ORGANISM: Artificial sequence
<220> FEATURE:
<223> OTHER INFORMATION: OsCDC48-T2, edit with byproduct
<220> FEATURE:
<221> NAME/KEY: misc_feature
<222> LOCATION: (25)..(39)
<223> OTHER INFORMATION: n is a, c, g, or t

<400> SEQUENCE: 296
tggcgccagc gccgccgctg agccnnnnnn nnnnnnnnnc gccgcagctg 50

<210> SEQ ID NO 297
<211> LENGTH: 50
<212> TYPE: DNA
<213> ORGANISM: Artificial sequence
<220> FEATURE:
<223> OTHER INFORMATION: OsCDC48-T2, edit with byproduct
<220> FEATURE:
<221> NAME/KEY: misc_feature
<222> LOCATION: (25)..(39)
<223> OTHER INFORMATION: n is a, c, g, or t

<400> SEQUENCE: 297
tggtgccggc gccgccgctg acccnnnnnn nnnnnnnnnc gccgcagctg 50

<210> SEQ ID NO 298
<211> LENGTH: 50
<212> TYPE: DNA
<213> ORGANISM: Artificial sequence
<220> FEATURE:
<223> OTHER INFORMATION: OsCDC48-T2, edit with byproduct
<220> FEATURE:
<221> NAME/KEY: misc_feature
<222> LOCATION: (25)..(39)
<223> OTHER INFORMATION: n is a, c, g, or t

<400> SEQUENCE: 298
tggtgccgac gccgccgctg acccnnnnnn nnnnnnnnnc gccgcagctg 50

<210> SEQ ID NO 299
<211> LENGTH: 50
<212> TYPE: DNA
<213> ORGANISM: Artificial sequence
<220> FEATURE:
<223> OTHER INFORMATION: OsCDC48-T2, edit with byproduct
<220> FEATURE:
<221> NAME/KEY: misc_feature
<222> LOCATION: (25)..(39)
<223> OTHER INFORMATION: n is a, c, g, or t

<400> SEQUENCE: 299
tggcgccagc gccgccgctg acccnnnnnn nnnnnnnnnc gccacagctg 50

<210> SEQ ID NO 300
<211> LENGTH: 72
<212> TYPE: DNA
<213> ORGANISM: Artificial sequence
<220> FEATURE:
<223> OTHER INFORMATION: OsEPSPS-T1, unedited sequence
<220> FEATURE:
<221> NAME/KEY: misc_feature
<222> LOCATION: (33)..(63)
<223> OTHER INFORMATION: n is a, c, g, or t

<400> SEQUENCE: 300
tcccttgggt ttatttgttt ccaagcatgt cannnnnnnn nnnnnnnnnn nnnnnnnnnn 60
nnntgcctgc tt 72

<210> SEQ ID NO 301
<211> LENGTH: 72
<212> TYPE: DNA
<213> ORGANISM: Artificial sequence
<220> FEATURE:
<223> OTHER INFORMATION: OsEPSPS-T1, precisely edited sequence
<220> FEATURE:
<221> NAME/KEY: misc_feature
<222> LOCATION: (33)..(63)
<223> OTHER INFORMATION: n is a, c, g, or t

<400> SEQUENCE: 301
tcccatgggt ttatttgttt ccaagcatgt cannnnnnnn nnnnnnnnnn nnnnnnnnnn 60
nnntgcctgc tt 72

<210> SEQ ID NO 302
<211> LENGTH: 72
<212> TYPE: DNA
<213> ORGANISM: Artificial sequence
<220> FEATURE:
<223> OTHER INFORMATION: OsEPSPS-T1, edit with byproduct
<220> FEATURE:
<221> NAME/KEY: misc_feature
<222> LOCATION: (33)..(63)
<223> OTHER INFORMATION: n is a, c, g, or t

<400> SEQUENCE: 302
tcccttgggt ttatgtgttt ccaagcatgt cannnnnnnn nnnnnnnnnn nnnnnnnnnn 60
nnntgcctgc tt 72

<210> SEQ ID NO 303
<211> LENGTH: 72
<212> TYPE: DNA
<213> ORGANISM: Artificial sequence
<220> FEATURE:
<223> OTHER INFORMATION: OsEPSPS-T1, edit with byproduct
<220> FEATURE:
<221> NAME/KEY: misc_feature
<222> LOCATION: (33)..(63)
<223> OTHER INFORMATION: n is a, c, g, or t

<400> SEQUENCE: 303
tcccatgggt ttatgtgttt ccaagcatgt cannnnnnnn nnnnnnnnnn nnnnnnnnnn 60
nnntgcctgc tt 72

<210> SEQ ID NO 304
<211> LENGTH: 72
<212> TYPE: DNA
<213> ORGANISM: Artificial sequence
<220> FEATURE:
<223> OTHER INFORMATION: OsEPSPS-T1, edit with byproduct
<220> FEATURE:
<221> NAME/KEY: misc_feature
<222> LOCATION: (33)..(63)
<223> OTHER INFORMATION: n is a, c, g, or t

<400> SEQUENCE: 304
tcccttgggt ttatttgttt ccaagcatgt cannnnnnnn nnnnnnnnnn nnnnnnnnnn 60
nnntgcctac tt 72

<210> SEQ ID NO 305
<211> LENGTH: 72
<212> TYPE: DNA
<213> ORGANISM: Artificial sequence
<220> FEATURE:
<223> OTHER INFORMATION: OsEPSPS-T1, edit with byproduct
<220> FEATURE:
<221> NAME/KEY: misc_feature
<222> LOCATION: (33)..(63)
<223> OTHER INFORMATION: n is a, c, g, or t

<400> SEQUENCE: 305
tcccttgggt ttatttgttt ccaagcatgc cannnnnnnn nnnnnnnnnn nnnnnnnnnn 60
nnntgcctgc tt 72

<210> SEQ ID NO 306
<211> LENGTH: 72
<212> TYPE: DNA
<213> ORGANISM: Artificial sequence
<220> FEATURE:
<223> OTHER INFORMATION: OsEPSPS-T1, byproduct
<220> FEATURE:
<221> NAME/KEY: misc_feature
<222> LOCATION: (33)..(63)
<223> OTHER INFORMATION: n is a, c, g, or t

<400> SEQUENCE: 306
tcccttgggt ttattcgttt ccaagcatgt cannnnnnnn nnnnnnnnnn nnnnnnnnnn 60
nnntgcctgc tt 72

<210> SEQ ID NO 307
<211> LENGTH: 100
<212> TYPE: DNA
<213> ORGANISM: Artificial sequence
<220> FEATURE:
<223> OTHER INFORMATION: OsCDC48-T1, reference sequence
<220> FEATURE:
<221> NAME/KEY: misc_feature
<222> LOCATION: (8)..(67)
<223> OTHER INFORMATION: n is a, c, g, or t

<400> SEQUENCE: 307
ctgctttnnn nnnnnnnnnn nnnnnnnnnn nnnnnnnnnn nnnnnnnnnn nnnnnnnnnn 60
nnnnnnnctt tcttctttct gattaatggc ccggagatta 100

<210> SEQ ID NO 308
<211> LENGTH: 100
<212> TYPE: DNA
<213> ORGANISM: Artificial sequence
<220> FEATURE:
<223> OTHER INFORMATION: OsCDC48-T1, wild-type
<220> FEATURE:
<221> NAME/KEY: misc_feature
<222> LOCATION: (8)..(67)
<223> OTHER INFORMATION: n is a, c, g, or t

<400> SEQUENCE: 308
ctgctttnnn nnnnnnnnnn nnnnnnnnnn nnnnnnnnnn nnnnnnnnnn nnnnnnnnnn 60
nnnnnnnctt tcttctttct gattaatggc ccggagatta 100

<210> SEQ ID NO 309
<211> LENGTH: 94
<212> TYPE: DNA
<213> ORGANISM: Artificial sequence
<220> FEATURE:
<223> OTHER INFORMATION: OsCDC48-T1, desired edit
<220> FEATURE:
<221> NAME/KEY: misc_feature
<222> LOCATION: (8)..(67)
<223> OTHER INFORMATION: n is a, c, g, or t

<400> SEQUENCE: 309
ctgctttnnn nnnnnnnnnn nnnnnnnnnn nnnnnnnnnn nnnnnnnnnn nnnnnnnnnn 60
nnnnnnnctt tcttctttct gattaatggc atta 94

```
<210> SEQ ID NO 310
<211> LENGTH: 27
<212> TYPE: DNA
<213> ORGANISM: Artificial sequence
<220> FEATURE:
<223> OTHER INFORMATION: OsCDC48-T1, edit with byproduct

<400> SEQUENCE: 310

ctgattgatg gtgcattaat ggcatta                                           27
```

METHOD FOR TARGETED MODIFICATION OF A PLANT GENOME SEQUENCE

CROSS-REFERENCE TO RELATED APPLICATIONS

This application is a U.S. National Phase of International Patent Application No. PCT/CN2020/117736, filed on Sep. 25, 2020, which claims priority to Chinese Application No. 202010036374.4, filed Jan. 14, 2020, and Chinese Application No. 201911062005.6, filed Nov. 1, 2019. The entire contents of these applications are incorporated herein by reference in their entirety.

SEQUENCE LISTING

This application contains a Sequence Listing which has been submitted in ASCII format via EFS-Web and is hereby incorporated by reference herein in its entirety. The ASCII text file was created on Jun. 17, 2026, is named 1022_Updated_Seq_Listing_20260617.txt and is 179,389 bytes in size.

TECHNICAL FIELD

The present invention relates to the field of plant genetic engineering. Specifically, the present invention relates to a method for targeted modification of a plant genome sequence. More specifically, the present invention relates to a method for targeted modification of a specific sequence in the plant genome into a target sequence of interest by a nuclease-reverse transcriptase fusion protein guided by a guide RNA, a genetically-modified plant produced by said method, and progenies of said plant.

BACKGROUND ART

Many important agronomic traits depend on sequences in the genome. By directionally changing specific sequences of the genome, new heritable traits may be conferred to organisms, providing possibility for disease treatment and breeding improvement. Currently, cleavage of a specific sequences can be achieved by the genome editing techniques (e.g., a CRISPR/Cas technique), so that a repairing pathway of cells is activated to repair injury site, and in turn the sequence at the target site is changed. Precise change to a genome sequence can be achieved based on a homologous recombination (HR) repairing pathway. However, in most higher organisms, especially plants, the homologous recombination efficiency is very low, so that wide application of the method is greatly limited. Furthermore, efficient conversion from cytosine to thymine (C-T) and efficient conversion from adenine to guanine (A-G) within the target site can be achieved by using a single base editing system. However, the method has limited base transition types, and precise insertions or deletions of fragments also cannot be achieved. Thus, there remains a need in the art for an efficient method capable of achieving precise directed modification of the plant genome sequences.

SUMMARY OF THE INVENTION

The present invention comprises a novel plant DNA precise editing system which is comprised of a Cas nuclease having target strand nicking activity (Cas9-H840A) and fused with a reverse transcriptase, and a pegRNA (prime editing gRNA) with a repair template (RT template) and a primer binding site (PBS) of a free single strand at the 3' end. According to the system, the PBS binds to the free single strand generated by a Cas nickase such as Cas9-H840A, a single-stranded DNA sequence is transcribed according to the given RT template, and any change of the DNA sequence in the genome located downstream part of −3 position of the PAM sequence can be achieved through cell repair. In addition, by introducing a new nicking sgRNA, nicks are generated in non-target strands of the pegRNA, which promote the cell to repair according to the donor template. Experimental results show that the system effectively induces precise modification at target sites in plants.

DETAILED DESCRIPTION OF THE INVENTION

1. Definition

Figure 1:
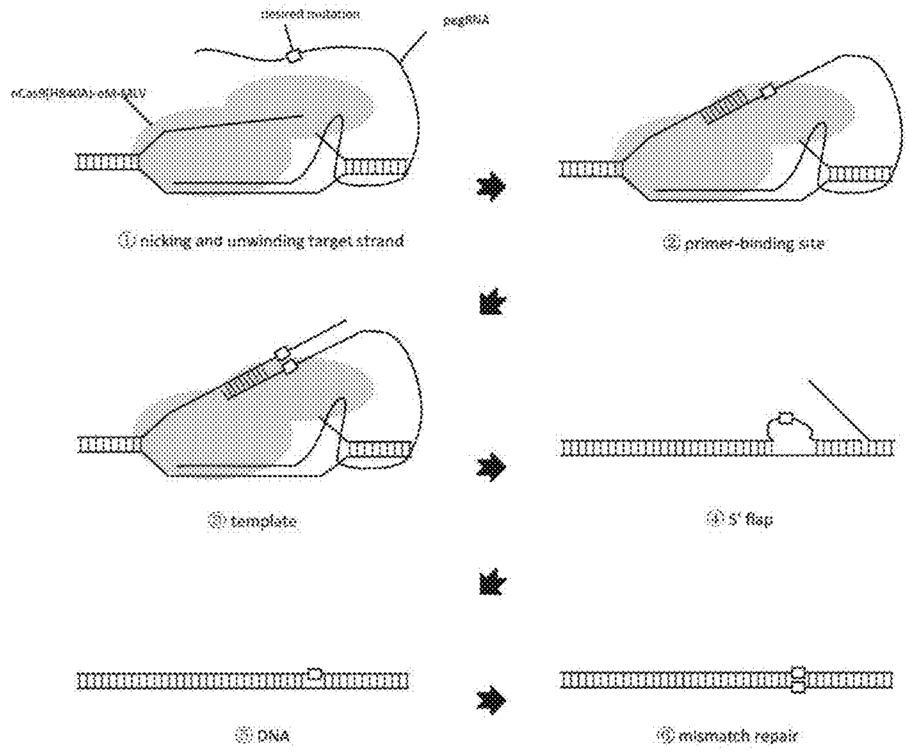
FIG. 1 shows a schematic diagram of mechanism underlying the present invention.

In the present invention, unless indicated otherwise, the scientific and technological terminologies used herein refer to meanings commonly understood by a person skilled in the art. Also, the terminologies and experimental procedures used herein relating to protein and nucleotide chemistry, molecular biology, cell and tissue cultivation, microbiology, immunology, all belong to terminologies and conventional methods generally used in the art. For example, the standard DNA recombination and molecular cloning technology used herein are well known to a person skilled in the art, and are described in details in the following references: Sambrook, J., Fritsch, E. F. and Maniatis, T., Molecular Cloning: A Laboratory Manual; Cold Spring Harbor Laboratory Press: Cold Spring Harbor, 1989. In the meantime, in order to better understand the present invention, definitions and explanations for the relevant terminologies are provided below.

As used herein, the term "and/or" encompasses all combinations of items connected by the term, and each combination should be regarded as individually listed herein. For example, "A and/or B" covers "A", "A and B", and "B". For example, "A, B, and/or C" covers "A", "B", "C", "A and B", "A and C", "B and C", and "A and B and C".

When the term "comprise" is used herein to describe the sequence of a protein or nucleic acid, the protein or nucleic acid may consist of the sequence, or may have additional amino acids or nucleotide at one or both ends of the protein or nucleic acid, but still have the activity described in this invention. In addition, those skilled in the art know that the methionine encoded by the start codon at the N-terminus of the polypeptide will be retained under certain practical conditions (for example, when expressed in a specific expression system), but does not substantially affect the function of the polypeptide. Therefore, when describing the amino acid sequence of specific polypeptide in the specification and claims of the present application, although it may not include the methionine encoded by the start codon at the N-terminus, the sequence containing the methionine is also encompassed, correspondingly, its coding nucleotide sequence may also contain a start codon; vice versa.

"Genome" as used herein encompasses not only chromosomal DNA present in the nucleus, but also organelle DNA present in the subcellular components (e.g., mitochondria, plastids) of the cell.

A "genetically modified plant" means a plant which comprises an exogenous polynucleotide or comprises a modified gene or expression regulatory sequence within its genome. For example, the exogenous polynucleotide can be stably integrated into the genome of the plant and inherited in successive generations. The exogenous polynucleotide may be integrated into the genome alone or as a part of a recombinant DNA construct. The modified gene or expression regulatory sequence is a gene or expression regulatory sequence comprising one or more nucleotide substitutions, deletions and additions in the plant genome.

The term "exogenous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

As used herein, an "expression construct" refers to a vector suitable for expression of a nucleotide sequence of interest in an organism, such as a recombinant vector. "Expression" refers to the production of a functional product. For example, the expression of a nucleotide sequence may refer to transcription of the nucleotide sequence (such as transcribe to produce an mRNA or a functional RNA) and/or translation of RNA into a protein precursor or a mature protein.

"Expression construct" of the invention may be a linear nucleic acid fragment, a circular plasmid, a viral vector, or, in some embodiments, an RNA that can be translated (such as an mRNA).

"Expression construct" of the invention may comprise regulatory sequences and nucleotide sequences of interest that are derived from different sources, or regulatory sequences and nucleotide sequences of interest derived from the same source, but arranged in a manner different than that normally found in nature.

"Regulatory sequence" or "regulatory element" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell. The promoter may be a constitutive promoter or a tissue-specific promoter or a developmentally-regulated promoter or an inducible promoter.

"Constitutive promoter" refers to a promoter that may cause expression of a gene in most circumstances in most cell types. "Tissue-specific promoter" and "tissue-preferred promoter" are used interchangeably, and refer to a promoter that is expressed predominantly but not necessarily exclusively in one tissue or organ, but that may also be expressed in one specific cell or cell type. "Developmentally regulated promoter" refers to a promoter whose activity is determined by developmental events. "Inducible promoter" selectively expresses a DNA sequence operably linked to it in response to an endogenous or exogenous stimulus (environment, hormones, or chemical signals, and so on).

Examples of promoters that can be used in the present invention include but are not limited to polymerase (pol) I, pol II or pol III promoters. Examples of pol I promoters include chicken RNA pol I promoter. Examples of pol II promoters include but are not limited to cytomegalovirus immediate early (CMV) promoter, rous sarcoma virus long terminal repeat (RSV-LTR) promoter and simian virus 40 (SV40) immediate early promoter. Examples of pol III promoters include U6 and H1 promoter. Inducible promoter such as metallothionein promoter can be used. Other examples of promoters include T7 bacteriophage promoter, T3 bacteriophage promoter, β-galactosidase promoter and Sp6 bacteriophage promoter etc. When used for plants, promoters that can be used include but are not limited to cauliflower mosaic virus 35S promoter, maize Ubi-1 promoter, wheat U6 promoter, rice U3 promoter, maize U3 promoter and rice actin promoter etc.

As used herein, the term "operably linked" means that a regulatory element (for example but not limited to, a promoter sequence, a transcription termination sequence, and so on) is associated to a nucleic acid sequence (such as a coding sequence or an open reading frame), such that the transcription of the nucleotide sequence is controlled and regulated by the transcriptional regulatory element. Techniques for operably linking a regulatory element region to a nucleic acid molecule are known in the art.

"Introduction" of a nucleic acid molecule (e.g., plasmid, linear nucleic acid fragment, RNA, etc.) or protein into an organism means that the nucleic acid or protein is used to transform a cell of the organism such that the nucleic acid or protein functions in the cell. As used in the present invention, "transformation" includes both stable and transient transformations. "Stable transformation" refers to the introduction of an exogenous nucleotide sequence into the genome, resulting in the stable inheritance of foreign genes. Once stably transformed, the exogenous nucleic acid sequence is stably integrated into the genome of the organism and any of its successive generations. "Transient transformation" refers to the introduction of a nucleic acid molecule or protein into a cell, performing its function without the stable inheritance of an exogenous gene. In transient transformation, the exogenous nucleic acid sequence is not integrated into the genome.

"Trait" refers to the physiological, morphological, biochemical, or physical characteristics of a cell or an organism.

"Agronomic trait" is a measurable parameter including but not limited to, leaf greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, disease resistance, cold resistance, salt tolerance, and tiller number and so on.

II. Plant Genome Editing System

In one aspect, the present invention relates to a genome editing system for targeted modification of a genomic DNA sequence of an organism, comprising i) a fusion protein and/or an expression construct comprising a nucleotide sequence encoding the fusion protein, wherein the fusion protein comprises a CRISPR nickase and a reverse transcriptase; and/or ii) at least one pegRNA and/or an expression construct comprising nucleotide sequence(s) encoding the at least one pegRNA, wherein each of the at least one pegRNA comprises a guide sequence, a scaffold sequence, a reverse transcription (RT) template sequence and a primer binding site (PBS) sequence in the direction from 5' to 3'.

In some embodiments, the at least one pegRNA is capable of forming a complex with the fusion protein and targeting the fusion protein to the target sequence in the genome, resulting in a nick in the target sequence.

In some embodiments, the organism is a plant.

As used herein, a "genome editing system" refers to a combination of components required for genome editing of the genome in a cell. The individual components, e.g., the fusion protein, the gRNA, etc., of the system may be present independently of each other, or may be present in any combination as a composition.

As used herein, a "target sequence" refer to a sequence which is approximately 20 nucleotides in length in the genome and is represented by the 5' or 3' flanking PAM (protospacer adjacent motif) sequence. In general, PAM is required for recognizing the target sequence by the complex formed by the CRISPR nuclease or a variant thereof and the guide RNA. For example, for the Cas9 nuclease and a variant thereof, the target sequence is, at the 3' end, closely adjacent to the PAM, for example, 5'-NGG-3'. Based on the presence of PAM, those skilled in the art may readily determine the target sequences available in the genome for targeting. In addition, depending on the locations of the PAMs, the target sequences may be located on any strand of genome DNA molecule. For Cas9 or derivatives thereof such as the Cas9 nickase, the target sequences are preferably 20 nucleotides in length.

In some embodiments, the CRISPR nickase in the fusion protein is capable of forming a nick within the target sequence in the genome DNA. In some embodiments, the CRISPR nickase is a Cas9 nickase.

In some embodiments, the Cas9 nickase is derived from *Streptococcus pyogenes* (*S. pyogenes*) SpCas9, and comprises at least an amino acid substitution H840A relative to wild type SpCas9. The exemplary wild type SpCas9 comprises an amino acid sequence set forth in SEQ ID NO: 1. In some embodiments, the Cas9 nickase comprises an amino acid sequence set forth in SEQ ID NO: 2. In some embodiments, the Cas9 nickase in the fusion protein is capable of forming a nick between the −3 position nucleotide (the first nucleotide at the 5' end of each PAM sequence is considered as the +1 site nucleotide) and the −4 position nucleotide of the PAM of the target sequence.

In some embodiments, the Cas9 nickase is a Cas9 nickase variant capable of recognizing an altered PAM sequence. In some preferred embodiments, the Cas9 nickase is a Cas9 variant that recognizes the PAM sequence 5'-NG-3'. In some embodiments, the Cas9 nickase variant that recognizes the PAM sequence 5'-NG-3' comprises the following amino acid substitutions H840A, R1335V, L1111R, D1135V, G1218R, E1219F, A1322R and T1337R relative to the wild type Cas9, wherein the amino acid numbering refers to SEQ ID NO: 1.

The nick formed by the Cas9 nickase of the present invention is capable of causing the target sequence to form a free single strand at the 3' terminal (3' free single strand) and a free single strand at the 5' terminal (5' free single strand).

In some embodiments, the reverse transcriptase in the fusion protein of the present invention may be derived from different sources. In some embodiments, the reverse transcriptase is a bacteria-derived reverse transcriptase. For example, in some embodiments, the reverse transcriptase is an M-MLV reverse transcriptase or a functional variant thereof. An exemplary wild type M-MLV reverse transcriptase sequence is set forth in SEQ ID NO: 3. In some embodiments, the reverse transcriptase is an enhanced M-MLV reverse transcriptase, for example, the amino acid sequence of the enhanced M-MLV reverse transcriptase is set forth in SEQ ID NO: 4. In some embodiments, the reverse transcriptase is CaMV-RT from Cauliflower mosaic viruses (CaMV), and an amino acid sequence of the CaMV-RT is set forth in SEQ ID NO: 5. In some embodiments, the reverse transcriptase is the bacteria-derived reverse transcriptase, for example, retron-RT from *Escherichia coli*, and an amino acid sequence of the retron-RT is set forth in SEQ ID NO: 6.

In some embodiments, the CRISPR nickase and the reverse transcriptase in the fusion protein are linked by a linker. As used herein, a "linker" may be a non-functional amino acid sequence which is 1-50 (e.g. 1, 2, 3, 4, 5, 6, 7, 8, 9, 10, 11, 12, 13, 14, 15, 16, 17, 18, 19, 20 or 20-25 or 25-50) or more amino acids in length and is free of secondary or higher structures. For example, the linker may be a flexible linker, for example, GGGGS (SEQ ID NO:15), GS, GAP, (GGGGS)x3 (SEQ ID NO:16), GGS, (GGS) x7 (SEQ ID NO:17), etc. For example, the linker may be a linker set forth in SEQ ID NO: 7.

In some embodiments, the CRISPR nickase in the fusion protein is fused to the N-terminus of the reverse transcriptase directly or through a linker. In some embodiments, the CRISPR nickase in the fusion protein is fused to the C-terminus of the reverse transcriptase directly or through a linker.

In some embodiments of the present invention, the fusion protein of the present invention may further comprise a nuclear localization sequence (NLS). In general, one or more NLSs in the fusion protein should be of sufficient strength to drive accumulation of the fusion protein in nuclei of the cells in an amount that can realize its editing function. In general, the strength of nuclear localization activity is determined by the number of NLS in the fusion protein, location of NLS in the fusion protein, the one or more specific NLSs as used in the fusion protein, or a combination of these factors.

The guide sequence (also referred to as seed sequence or spacer sequence) in at least one pegRNA of the present invention is configured to have sufficient sequence identity (preferably 100% identity) to the target sequence so as to achieve sequence-specific targeting by binding to complementary strand of the target sequence through base pairing.

A variety of scaffold sequences of the gRNAs suitable for genome editing based on the CRISPR nuclease (e.g. Cas9) are known in the field and may be used in the pegRNA of the present invention. In some embodiments, the scaffold sequence of the gRNA is set forth in SEQ ID NO: 8.

In some embodiments, the primer binding sequence is configured to be complementary to at least a portion of the target sequence (preferably fully paired with at least a portion of the target sequence), and preferably, the primer binding sequence is complementary to (preferably fully paired with at least a portion of the 3' free single strand) at least a portion of the 3' free single strand caused by the nick in the DNA strand where the target sequence is located, in particular complementary to (preferably fully paired with) the nucleotide sequences at the 3' terminal of the 3' free single strand. When the 3' free single strand of the strand binds to the primer binding sequence by base pairing, the 3' free single strand can serve as a primer, and the reverse transcription (RT) template sequence closely adjacent to the primer binding sequence can serve as a template for reverse transcription by the reverse transcriptase in the fusion protein, and the DNA sequence corresponding to the reverse transcription (RT) template sequence is obtained through extension.

The primer binding sequence depends on the length of the free single strand formed in the target sequence by the CRISPR nickase, however, they should have a minimum length capable of ensuring specific binding. In some embodiments, the primer binding sequence may be 4-20 nucleotides in length, for example, 4, 5, 6, 7, 8, 9, 10, 11, 12, 13, 14, 15, 16, 17, 18, 19 and 20 nucleotides in length.

In some embodiments, the primer binding sequence is configured to have a Tm (melting temperature) of no more than about 52° C. In some embodiments, the Tm (melting temperature) of the primer binding sequences is about 18° C.-52° C., preferably about 24° C.-36° C., more preferably about 28° C.-32° C., and most preferably about 30° C.

Methods for calculating the Tm of a nucleic acid sequence is well known in the field, for example, an Oligo Analysis Tool online analytical tool may be used for calculation. An exemplary calculation formula is $Tm=N_{G:C}*4+N_{A:T}*2$, wherein $N_{G:C}$ is the number of G and C bases in the sequence, and $N_{A:T}$ is the number of A and T bases in the sequence. The suitable Tm may be obtained by selecting a suitable PBS length. Alternatively, PBS sequence with the appropriate Tm may be obtained by selecting the appropriate target sequence.

In some embodiments, the RT template sequence may be any sequence. Through the above reverse transcription, sequence information thereof may be integrated into the DNA strand where the target sequence is located (namely, the strand containing the PAM of the target sequence), and then DNA double strands containing the sequence information of the RT template are formed through DNA repairing of the cell. In some embodiments, the RT template sequence comprises desired modification(s). For example, the desired modification comprises substitution, deletion and/or addition of one or more nucleotide. For example, the modification comprises one or more substitutions selected from: C to T substitution, C to G substitution, C to A substitution, G to T substitution, G to C substitution, G to A substitution, A to T substitution, A to G substitution, A to C substitution, T to C substitution, T to G substitution and T to A substitution; and/or comprises deletion of one or more nucleotides, for example, deletion of 1 to about 100 or more nucleotides, e.g. deletion of 1, 2, 3, 4, 5, about 10, about 20, about 30, about 40, about 50, about 75, about 100 nucleotides; and/or comprises insertion of one or more nucleotides, for example, insertion of 1 to about 100 or more nucleotides, for example, insertion of 1 to about 100 or more nucleotides, for example, insertion of 1, 2, 3, 4, 5, about 10, about 20, about 30, about 40, about 50, about 75, about 100 nucleotides.

In some embodiments, the RT template sequence is configured as corresponding to the sequence downstream the nick of the target sequence (e.g., being complementary to at least a portion of the sequence downstream the nick of the target sequence) and contain desired modification(s). For example, the desired modification comprises substitution, deletion and/or addition of one or more nucleotide. For example, the modification comprises one or more substitutions selected from: C to T substitution, C to G substitution, C to A substitution, G to T substitution, G to C substitution, G to A substitution, A to T substitution, A to G substitution, A to C substitution, T to C substitution, T to G substitution and T to A substitution; and/or comprises deletion of one or more nucleotides, for example, deletion of 1 to about 100 or more nucleotides, e.g. deletion of 1, 2, 3, 4, 5, about 10, about 20, about 30, about 40, about 50, about 75, about 100 nucleotides; and/or comprises insertion of one or more nucleotides, for example, insertion of 1 to about 100 or more nucleotides, for example, insertion of 1 to about 100 or more nucleotides, for example, insertion of 1, 2, 3, 4, 5, about 10, about 20, about 30, about 40, about 50, about 75, about 100 nucleotides.

In some embodiments, the RT template sequence may be about 1-300 or more nucleotides in length, for example, 1, 2, 3, 4, 5, about 10, about 20, about 30, about 40, about 50, about 75, about 100, about 125, about 150, about 175, about 200, about 225, about 250, about 275, about 300 nucleotides or more nucleotides in length. Preferably, the RT template sequence is 7, 8, 9, 10, 11, 12, 13, 14, 15, 16, 17, 18, 19, 20, 21, 22 and 23 nucleotides in length.

In some embodiments, the plant genome editing system further comprises a nicking gRNA (the nicking gRNA is used for generating an additional nick) and/or an expression construct comprising a nucleotide sequence encoding the nicking gRNA, wherein the nicking gRNA comprises a guide sequence and a scaffold sequence. In some preferred embodiments, the nicking gRNA does not contain the reverse transcription (RT) template sequence and the primer binding site (PBS) sequence.

The guide sequence (also referred to as seed sequence or spacer sequence) in the nicking gRNA of the present invention is configured to have sufficient sequence identity (preferably 100% identity) to a nicking target sequence in the genome, so that the fusion protein of the present invention is targeted to the nicking target sequence, resulting in a nick in the nicking target sequence, wherein the nicking target sequence and the target sequence (pegRNA target sequence) targeted by the pegRNA are located on the opposite strand of the genome DNA. In some embodiments, the nick formed by the nicking RNA and the nick formed by the pegRNA are about 1 to about 300 or more nucleotides apart, e.g., 1, 2, 3, 4, 5, about 10, about 20, about 30, about 40, about 50, about 75, about 100, about 125, about 150, about 175, about 200, about 225, about 250, about 275, about 300 nucleotides or more nucleotides apart. In some embodiments, the nick created by the nicking RNA is located upstream or downstream of the nick formed by the pegRNA (upstream or downstream refers to the DNA strand on which the pegRNA target sequence is located). In some embodiments, the guide sequence in the nicking gRNA has sufficient sequence identity (preferably 100% identity) to the pegRNA target sequence on the opposite strand after editing event occur (modified pegRNA target sequence), so that the nicking gRNA targets only the nicking target sequence that is generated after pegRNA-induced sequence targeting and modification. In some embodiments, the PAM of the nicking target sequence is located within the complementary sequence of the pegRNA target sequence.

In some embodiments, the sequence of the pegRNA and/or the nicking gRNA may be precisely processed by using a self-processing system. In some specific embodiments, the 5' end of the pegRNA and/or the nicking gRNA are linked to the 3' end of a first ribozyme, wherein the first ribozyme is designed to cleave the fusion at the 5' end of the pegRNA and/or the nicking gRNA; and/or the 3' end of the pegRNA and/or the nicking gRNA is linked to the 5' end of a second ribozyme, wherein the second ribozyme is designed to cleave the fusion at the 3' end of the pegRNA and/or the nicking gRNA. The design of the first or second ribozyme is within the capabilities of those skilled in the art. For example, see Gao et al. JIPB, apr, 2014; Vol 56, Issue 4, 343-349. As for a method for precise processing of gRNA, see, for example, WO 2018/149418.

In some embodiments, the genome editing system comprises at least one pair of pegRNAs and/or expression construct comprising the nucleotide sequence encoding the at least one pair of pegRNAs. In some embodiments, the two pegRNAs of the pair of pegRNAs are configured to target different target sequences on the same strand of the genome DNA. In some embodiments, the two pegRNAs of the pair of pegRNAs are configured to target the target sequences on different strands of the genome DNA. In some embodiments, the PAM for the target sequence of one pegRNA of the pair of pegRNAs is located on a sense strand, and the PAM for the other pegRNA is located on an antisense strand. In some embodiments, the induced nicks of the two pegRNAs are located on both sides of a site to be modified respectively. In some embodiments, the pegRNA-induced nick for the sense strand is located upstream (5' direction) of the site to be modified, and the pegRNA-induced nick for the antisense strand is located downstream (3' direction) of the site to be modified. The “upstream” or “downstream” refers to the sense strand. In some embodiments, the induced nicks of the two pegRNAs are about 1 to about 300 or more nucleotides apart, for example, 1-15 nucleotides apart.

In some embodiments, the two pegRNAs in the pair of pegRNAs are configured to introduce the same desired modification. For example, one pegRNA is configured to introduce a A to G substitution in the sense strand, and the other pegRNA is configured to introduce a T to C substitution at the corresponding position of the antisense strand. For another example, one pegRNA is configured to introduce two nucleotide deletions in the sense strand, and the other pegRNA is configured to similarly introduce two nucleotide deletions at the corresponding position of the antisense strand. Other types of modification may be made in a similar manner. Designing appropriate RT template sequences can allow the pegRNAs targeting two different strands to achieve the same desired modification.

In order to obtain efficient expression in plants, in some embodiments of the present invention, the nucleotide sequence encoding the fusion protein is subjected to codon optimization for plant species whose genome is to be modified.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y, et al. "Codon usage tabulated from the international DNA sequence databases: status for the year 2000" Nucl. Acids Res. 28:292 (2000).

In some embodiments, the fusion protein of the present invention is encoded by nucleotide sequence of any one of SEQ ID NOs: 9-11, or comprises amino acid sequence of any one of SEQ ID NOs: 12-14.

Plants that can be genome-modified by the genome editing system of the invention include monocots and dicots. For example, the plant may be a crop plant such as wheat, rice, corn, soybean, sunflower, sorghum, canola, alfalfa, cotton, barley, millet, sugar cane, tomato, tobacco, tapioca or potato.

In another aspect, the present invention provides a method of determining the PBS sequence in the pegRNA of the genome editing system of the present invention, comprising the steps of:

a) determining at least one candidate target sequence based on the PAM recognized by the CRISPR nickase as used and the site to be modified;
b) obtaining a series of PBS sequences based on the nick location which can be generated by the CRISPR nickase at the at least one candidate target sequence;
c) calculating the Tm of the PBS sequences; and
d) selecting the PBS sequences with Tm of not more than 52° C., for example, Tm of about 18° C. to 52° C., preferably about 24° C. to 36° C., more preferably about 28° C. to 32° C., and most preferably about 30° C.

III. Method of Producing a Genetically Modified Plant

In another aspect, the present invention provides a method of producing a genetically modified plant, comprising the step of introducing the genome editing system of the present invention into at least one plant, resulting in modification in genome of the at least one plant. The modification comprises substitution, deletion and/or addition of one or more nucleotide. For example, the modification comprises one or more substitutions selected from: C to T substitution, C to G substitution, C to A substitution, G to T substitution, G to C substitution, G to A substitution, A to T substitution, A to G substitution, A to C substitution, T to C substitution, T to G substitution and T to A substitution; and/or comprises deletion of one or more nucleotides, for example, deletion of 1 to about 100 or more nucleotides, e.g. deletion of 1, 2, 3, 4, 5, about 10, about 20, about 30, about 40, about 50, about 75, about 100 nucleotides; and/or comprises insertion of one or more nucleotides, for example, insertion of 1 to about 100 or more nucleotides, for example, insertion of 1 to about 100 or more nucleotides, for example, insertion of 1, 2, 3, 4, 5, about 10, about 20, about 30, about 40, about 50, about 75, about 100 nucleotides.

In some embodiments, the method further comprises the step of screening the plant with the desired modification from the at least one plant.

In the method of the present invention, the genome editing system may be introduced into the plants in a variety of methods well known to those skilled in the art. The methods used for introducing the genome editing system of the present invention into a plant include, but are not limited to a gene gun method, PEG-mediated protoplast transformation, *Agrobacterium*-mediated transformation, plant virus-mediated transformation, pollen tube pathway and ovary injection method. Preferably, the genome editing system is introduced into the plant by transient transformation.

In the method of the present invention, modification of the genome may be achieved by only introducing or producing the fusion protein and the gRNAs in the plant cells, and the modification can be stably inherited without stably transforming exogenous polynucleotides encoding the components of the genome editing system into the plant. This avoids the potential off-target effects due to the stably existing (continuously produced) genome editing system and also avoids the integration of the exogenous nucleotide sequences in the plant genome, thereby providing greater biosafety.

In some preferred embodiments, the introduction is carried out in the absence of selection pressure to avoid integration of the exogenous nucleotide sequence into the plant genome.

In some embodiments, the introduction comprises transforming the genome editing system of the present invention into an isolated plant cell or tissue and then regenerating the transformed plant cell or tissue into an intact plant. Preferably, the regeneration is carried out in the absence of selection pressure, i.e., no selection agent for the selectable gene on the expression vector is used during tissue culture. Avoiding the use of a selection agent can increase the regeneration efficiency of the plant, obtaining a modified plant free of exogenous nucleotide sequences.

In other embodiments, the genome editing system of the present invention can be transformed into specific parts of an intact plant, such as leaves, shoot tips, pollen tubes, young ears or hypocotyls. This is particularly suitable for the transformation of plants that are difficult to regenerate in tissue culture.

In some embodiments of the invention, the in vitro expressed protein and/or the in vitro transcribed RNA molecule (e.g., the expression construct is in vitro transcribed RNA molecule) are directly transformed into the plant. The protein and/or RNA molecule is capable of performing genome editing in plant cells and is subsequently degraded by the cell, avoiding integration of the exogenous nucleotide sequence in the plant genome.

Thus, in some embodiments, using the method of the present invention for plant genetic modification and breeding can obtain plants with the genome free of exogenous polynucleotide integration, namely transgene-free modified plants.

In some embodiments, the method further comprises the step of culturing the plant cell, tissue or whole plant into which the genome editing system has been introduced at an elevated temperature, for example, the elevated temperature is 37° C.

In some embodiments of the present invention, the modified genome region is associated with plant traits, such as the agronomic traits, so that modified results in a plant having altered (preferably improved) traits, such as agronomic traits, relative to a wild type plant.

In some embodiments, the method further comprises the step of screening a plant having the desired modification and/or desired traits, such as agronomic traits.

In some embodiments of the present invention, the method further comprises the step of obtaining progenies of the genetically modified plant. Preferably, the genetically modified plant or the progenies thereof have the desired modification and/or the desired traits, such as agronomic traits.

In another aspect, the invention also provides a genetically modified plant or progenies or a part thereof, wherein the plant is obtained by the method according to the present invention as described above. In some embodiments, the genetically modified plant or the progenies or a part thereof is transgene-free. Preferably, the genetically modified plant or progenies thereof have the desired genetic modification and/or the desired traits, such as agronomic traits.

In another aspect, the present invention provides a method of plant breeding comprising crossing a first genetically modified plant obtained by the above method of the present invention with a second plant not containing the modification, thereby the genetic modification is introduced into the second plant. Preferably, the first genetically modified plant has the desired traits, such as the agronomic traits.

EXAMPLES

Materials and Methods

1. Vector Construction

The nCas9 (H840A)-M-MLV construct, the nCas9 (H840A)-CaMV construct and the nCas9 (H840A)-retron construct were constructed by Suzhou Jinweizhi Co. Ltd. The M-MLV used in the examples has 5 amino acid mutations compared to the wild type M-MLV reverse transcriptase. The M-MLV, the RT-CaMV and the RT-retron are all subjected to codon optimization for monocots.

The pegRNA fragments (including the RT and PBS sequences) were constructed into the vectors driven by OsU3 promoter by using a Gibson method to obtain OsU3-pegRNA constructs suitable for use in rice. The pegRNA fragments (including the RT and PBS sequences) were constructed into vectors driven by TaU6 promoter by using the Gibson method to obtain TaU6-pegRNA constructs suitable for use in wheat. The pegRNA fragments (including the RT and PBS sequences) with ribozymes at both the 5' end and the 3' end were constructed into vectors driven by maize Ubiquitin-1 (Ubi-1) promoter by using the Gibson method to obtain Ubi-pegRNA-R constructs.

The nicking gRNAs were constructed into vectors driven by TaU3 promoter through T4 ligase to obtain TaU3-nick vectors.

TABLE 1

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| BFP-peg01 | CTCGTGACCACCTT CACCCAC**GG** (SEQ ID NO: 18) | TGCACGCCGTACGTGA AGGTGGTCAC (SEQ ID NO: 19) | +1-2 CC to GT | 14 | 12 | 10 |
| OsAAT-peg01 | CAAGGATCCCAGCC CCGTGA**AGG** (SEQ ID NO: 20) | AGATTGACCTGGACGG GGCTGGGAT (SEQ ID NO: 21) | +2-3 GA to CC | 12 | 13 | 10 |
| OsALS-T1-peg01 | GGGTATGGTGGTGC AATGGG**AGG** (SEQ ID NO: 22) | TAAAACCTATCCTCCAA TTGCACCACCA (SEQ ID NO: 23) | +1 G to T | 12 | 16 | 15 |
| OsALS-T2-peg01 | GTGCTGCCTATGATC CCAAG**TGG** (SEQ ID NO: 24) | TGAATGCGCCCCCAATT GGGATCATAG (SEQ ID NO: 25) | +3 G to T | 10 | 17 | 14 |
| OsALS-T2-peg02 | GTGCTGCCTATGATC CCAAG**TGG** (SEQ ID NO: 26) | TGAATGCGCCCCCACCT GGGATCATAG (SEQ ID NO: 27) | +2 A to G | 10 | 17 | 15 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| OsALS-T2-pegAT | GTGCTGCCTATGATC CCAAG**TGG** (SEQ ID NO: 28) | TGAATGCGCCCCCACAT GGGATCATAG (SEQ ID NO: 29) | +2 A to T | 10 | 17 | 15 |
| OsALS-T2-pegAC | GTGCTGCCTATGATC CCAAG**TGG** (SEQ ID NO: 30) | TGAATGCGCCCCCACG TGGGATCATAG (SEQ ID NO: 31) | +2 A to C | 10 | 17 | 15 |
| OsALS-T2-pegTA | GTGCTGCCTATGATC CCAAG**TGG** (SEQ ID NO: 32) | TGAATGCGCCCCCTCTT GGGATCATAG (SEQ ID NO: 33) | +4 T to A | 10 | 17 | 13 |
| OsALS-T2-pegTC | GTGCTGCCTATGATC CCAAG**TGG** (SEQ ID NO: 34) | TGAATGCGCCCCCGCTT GGGATCATAG (SEQ ID NO: 35) | +4 T to C | 10 | 17 | 13 |
| OsALS-T2-pegTG | GTGCTGCCTATGATC CCAAG**TGG** (SEQ ID NO: 36) | TGAATGCGCCCCCCCTT GGGATCATAG (SEQ ID NO: 37) | +4 T to G | 10 | 17 | 13 |
| OsALS-T2-pegGA | GTGCTGCCTATGATC CCAAG**TGG** (SEQ ID NO: 38) | TGAATGCGCCCCCATTT GGGATCATAG (SEQ ID NO: 39) | +3 G to A | 10 | 17 | 14 |
| OsALS-T2-pegAGCA | GTGCTGCCTATGATC CCAAG**TGG** (SEQ ID NO: 40) | TGAATGCGCCCCCATGT GGGATCATAG (SEQ ID NO: 41) | +2-3 AG to CA | 10 | 17 | 14 |
| OsALS-T2-pegPBS6 | GTGCTGCCTATGATC CCAAG**TGG** (SEQ ID NO: 42) | TGAATGCGCCCCCACCT GGGATC (SEQ ID NO: 43) | +2 A to G | 6 | 17 | 15 |
| OsALS-T2-pegPBS8 | GTGCTGCCTATGATC CCAAG**TGG** (SEQ ID NO: 44) | TGAATGCGCCCCCACCT GGGATCAT (SEQ ID NO: 45) | +2 A to G | 8 | 17 | 15 |
| OsALS-T2-pegPBS12 | GTGCTGCCTATGATC CCAAG**TGG** (SEQ ID NO: 46) | TGAATGCGCCCCCACCT GGGATCATAGGC (SEQ ID NO: 47) | +2 A to G | 12 | 17 | 15 |
| OsALS-T2-pegPBS14 | GTGCTGCCTATGATC CCAAG**TGG** (SEQ ID NO: 48) | TGAATGCGCCCCCACCT GGGATCATAGGCAG (SEQ ID NO: 49) | +2 A to G | 14 | 17 | 15 |
| OsALS-T2-pegPBS16 | GTGCTGCCTATGATC CCAAG**TGG** (SEQ ID NO: 50) | TGAATGCGCCCCCACCT GGGATCATAGGCAGCA (SEQ ID NO: 51) | +2 A to G | 16 | 17 | 15 |
| OsALS-T2-pegRT10 | GTGCTGCCTATGATC CCAAG**TGG** (SEQ ID NO: 52) | GCCCCCACCTGGGATCA TAG (SEQ ID NO: 53) | +2A to G | 10 | 10 | 8 |
| OsALS-T2-pegRT11 | GTGCTGCCTATGATC CCAAG**TGG** (SEQ ID NO: 54) | CGCCCCCACCTGGGAT CATAG (SEQ ID NO: 55) | +2 A to G | 10 | 11 | 9 |
| OsALS-T2-pegRT13 | GTGCTGCCTATGATC CCAAG**TGG** (SEQ ID NO: 56) | TGCGCCCCCACCTGGG ATCATAG (SEQ ID NO: 57) | +2 A to G | 10 | 13 | 11 |
| OsALS-T2-pegRT15 | GTGCTGCCTATGATC CCAAG**TGG** (SEQ ID NO: 58) | AATGCGCCCCCACCTG GGATCATAG (SEQ ID NO: 59) | +2 A to G | 10 | 15 | 13 |
| OsALS-T2-pegRT18 | GTGCTGCCTATGATC CCAAG**TGG** (SEQ ID NO: 60) | TTGAATGCGCCCCCACC TGGGATCATAG (SEQ ID NO: 61) | +2 A to G | 10 | 18 | 16 |
| OsALS-T2-pegRT19 | GTGCTGCCTATGATC CCAAG**TGG** (SEQ ID NO: 62) | CTTGAATGCGCCCCCAC CTGGGATCATAG (SEQ ID NO: 63) | +2 A to G | 10 | 19 | 17 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| OsALS-T2-pegRT21 | GTGCTGCCTATGATC CCAAG**TGG** (SEQ ID NO: 64) | TCCTTGAATGCGCCCCC ACCTGGGATCATAG (SEQ ID NO: 65) | +2 A to G | 10 | 21 | 19 |
| OsALS-T2-pegRT23 | GTGCTGCCTATGATC CCAAG**TGG** (SEQ ID NO: 66) | TGTCCTTGAATGCGCCC CCACCTGGGATCATAG (SEQ ID NO: 67) | +2 A to G | 10 | 23 | 21 |
| OsCDC48-T1-peg01 | GCTAGCTTTGACAT AATCTC**CGG** (SEQ ID NO: 68) | ATTAATGGCATTATGTC AAAG (SEQ ID NO: 69) | +1-6 CTCCGG del | 12 | 9 | 9 |
| OsCDC48-T1-peg02 | GCTAGCTTTGACAT AATCTC**CGG** (SEQ ID NO: 70) | ATTAATGGCCTTAAGAT TATGTCAAAG (SEQ ID NO: 71) | +3-5 AG to CA | 12 | 15 | 10 |
| OsCDC48-T1-peg03 | GCTAGCTTTGACAT AATCTC**CGG** (SEQ ID NO: 72) | ATTAATGGCCCGGATCC GATTATGTCAAAG (SEQ ID NO: 73) | +2 GGA ins | 12 | 18 | 11 |
| OsCDC48-T1-pegAT | GCTAGCTTTGACAT AATCTC**CGG** (SEQ ID NO: 74) | TTCTTCTTTCTGATTAA AGGCCCGGAGATTATGT CAAAG (SEQ ID NO: 75) | +10 A to T | 12 | 27 | 17 |
| OsCDC48-T1-pegAC | GCTAGCTTTGACAT AATCTC**CGG** (SEQ ID NO: 76) | TTCTTCTTTCTGATTAA GGGCCCGGAGATTATGT CAAAG (SEQ ID NO: 77) | +10 A to C | 12 | 27 | 17 |
| OsCDC48-T1-pegAG | GCTAGCTTTGACAT AATCTC**CGG** (SEQ ID NO: 78) | TTCTTCTTTCTGATTAA CGGCCCGGAGATTATGT CAAAG (SEQ ID NO: 79) | +10 A to G | 12 | 27 | 17 |
| OsCDC48-T1-pegCA | GCTAGCTTTGACAT AATCTC**CGG** (SEQ ID NO: 80) | ATTAATGGCCCGGATAT TATGTCAAAG (SEQ ID NO: 81) | +1 C to A | 12 | 15 | 14 |
| OsCDC48-T1-pegCT | GCTAGCTTTGACAT AATCTC**CGG** (SEQ ID NO: 82) | ATTAATGGCCCGGAAAT TATGTCAAAG (SEQ ID NO: 83) | +1 C to T | 12 | 15 | 14 |
| OsCDC48-T1-pegCG | GCTAGCTTTGACAT AATCTC**CGG** (SEQ ID NO: 84) | ATTAATGGCCCGGACAT TATGTCAAAG (SEQ ID NO: 85) | +1 C to G | 12 | 15 | 14 |
| OsCDC48-T1-pegGA | GCTAGCTTTGACAT AATCTC**CGG** (SEQ ID NO: 86) | ATTAATGGCCTGGAGAT TATGTCAAAG (SEQ ID NO: 87) | +5 G to A | 12 | 15 | 10 |
| OsCDC48-T1-pegGC | GCTAGCTTTGACAT AATCTC**CGG** (SEQ ID NO: 88) | ATTAATGGCCGGGAGAT TATGTCAAAG (SEQ ID NO: 89) | +5 G to C | 12 | 15 | 10 |
| OsCDC48-T1-pegGT | GCTAGCTTTGACAT AATCTC**CGG** (SEQ ID NO: 90) | ATTAATGGCCAGGAGAT TATGTCAAAG (SEQ ID NO: 91) | +5 G to T | 12 | 15 | 10 |
| OsCDC48-T1-pegTA | GCTAGCTTTGACAT AATCTC**CGG** (SEQ ID NO: 92) | ATTAATGGCCCGGTGAT TATGTCAAAG (SEQ ID NO: 93) | +2 T to A | 12 | 15 | 13 |
| OsCDC48-T1-pegTC | GCTAGCTTTGACAT AATCTC**CGG** (SEQ ID NO: 94) | ATTAATGGCCCGGGGAT TATGTCAAAG (SEQ ID NO: 95) | +2 T to C | 12 | 15 | 13 |
| OsCDC48-T1-pegTG | GCTAGCTTTGACAT AATCTC**CGG** (SEQ ID NO: 96) | ATTAATGGCCCGGCGAT TATGTCAAAG (SEQ ID NO: 97) | +2 T to G | 12 | 15 | 13 |
| OsCDC48-T1-pegPBS8 | GCTAGCTTTGACAT AATCTC**CGG** (SEQ ID NO: 98) | ATTAATGGCATTATGTC (SEQ ID NO: 99) | +1-6 CTCCGG del | 8 | 9 | 9 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| OsCDC48-T1-pegPBS10 | GCTAGCTTTGACAT AATCTC**CGG** (SEQ ID NO: 100) | ATTAATGGCATTATGTC AA (SEQ ID NO: 101) | +1-6 CTCCGG del | 10 | 9 | 9 |
| OsCDC48-T1-pegPBS14 | GCTAGCTTTGACAT AATCTC**CGG** (SEQ ID NO: 102) | ATTAATGGCATTATGTC AAAGCT (SEQ ID NO: 103) | +1-6 CTCCGG del | 14 | 9 | 9 |
| OsCDC48-T1-pegPBS16 | GCTAGCTTTGACAT AATCTC**CGG** (SEQ ID NO: 104) | ATTAATGGCATTATGTC AAAGCTAG (SEQ ID NO: 105) | +1-6 CTCCGG del | 16 | 9 | 9 |
| OsCDC48-T1-pegRT7 | GCTAGCTTTGACAT AATCTC**CGG** (SEQ ID NO: 106) | TAATGGCATTATGTCAA AG (SEQ ID NO: 107) | +1-6 CTCCGG del | 8 | 7 | 7 |
| OsCDC48-T1-pegRT11 | GCTAGCTTTGACAT AATCTC**CGG** (SEQ ID NO: 108) | TGATTAATGGCATTATG TCAAAG (SEQ ID NO: 109) | +1-6 CTCCGG del | 8 | 11 | 11 |
| OsCDC48-T1-pegRT13 | GCTAGCTTTGACAT AATCTC**CGG** (SEQ ID NO: 110) | TCTGATTAATGGCATTAT GTCAAAG (SEQ ID NO: 111) | +1-6 CTCCGG del | 8 | 13 | 13 |
| OsCDC48-T1-pegRT15 | GCTAGCTTTGACAT AATCTC**CGG** (SEQ ID NO: 112) | TTTCTGATTAATGGCATT ATGTCAAAG (SEQ ID NO: 113) | +1-6 CTCCGG del | 8 | 15 | 15 |
| OsCDC48-T1-pegins3 | GCTAGCTTTGACAT AATCTC**CGG** (SEQ ID NO: 114) | ATTAATGGCCCGGAGA CCATTATGTCAAAG (SEQ ID NO: 115) | +1 GGT ins | 12 | 18 | 16 |
| OsCDC48-T1-pegins6 | GCTAGCTTTGACAT AATCTC**CGG** (SEQ ID NO: 116) | ATTAATGGCCCGGAGA CCAACATTATGTCAAAG (SEQ ID NO: 117) | +1 GTTGGT ins | 12 | 21 | 16 |
| OsCDC48-T1-pegins15 | GCTAGCTTTGACAT AATCTC**CGG** (SEQ ID NO: 118) | ATTAATGGCCCGGAGA CCAACCTGTCCGACATT ATGTCAAAG (SEQ ID NO: 119) | +1 15 nt ins | 12 | 30 | 16 |
| OsCDC48-T1-pegins30 | GCTAGCTTTGACAT AATCTC**CGG** (SEQ ID NO: 120) | ATTAATGGCCCGGAGA CCAACCTGTCCGACATC ATCGAGAAGGAGATTAT GTCAAAG (SEQ ID NO: 121) | +1 30 nt ins | 12 | 45 | 16 |
| OsCDC48-T1-pegins60 | GCTAGCTTTGACAT AATCTC**CGG** (SEQ ID NO: 122) | ATTAATGGCCCGGAGA CCAACCTGTCCGACATC ATCGAGAAGGAGACGG GCAAGCAACTCGTGAT CCAGGAGAGCATTATGT CAAAG (SEQ ID NO: 123) | +1 60 nt ins | 12 | 75 | 16 |
| OsCDC48-T1-pegdel12 | GCTAGCTTTGACAT AATCTC**CGG** (SEQ ID NO: 124) | TTTCTGATTATTATGTCA AAG (SEQ ID NO: 125) | +1 12-nt del | 12 | 9 | 9 |
| OsCDC48-T1-pegdel20 | GCTAGCTTTGACAT AATCTC**CGG** (SEQ ID NO: 126) | GCTTTCTTCTATTATGTC AAAG (SEQ ID NO: 127) | +1 20-nt del | 12 | 9 | 9 |
| OsCDC48-T1-pegdel40 | GCTAGCTTTGACAT AATCTC**CGG** (SEQ ID NO: 128) | TGTTGCTAAATTATGTC AAAG (SEQ ID NO: 129) | +1 40-nt del | 12 | 9 | 9 |
| OsCDC48-T1-pegdel70 | GCTAGCTTTGACAT AATCTC**CGG** (SEQ ID NO: 130) | TGGCTCTGGATTATGTC AAAG (SEQ ID NO: 131) | +1 70-nt del | 12 | 9 | 9 |
| OsCDC48-T2-peg01 | GACCAGCCAGCGTC TGGCGC**CGG** (SEQ ID NO: 132) | GGCGCCGGCTTTGCCA GACGCTGGC (SEQ ID NO: 133) | +2 AAA ins | 12 | 13 | 9 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| OsCDC48-T2-peg02 | GACCAGCCAGCGTC TGGCGC**CGG** (SEQ ID NO: 134) | TCAGCGGCGGCGCTGG CGCCAGACGCTGGC (SEQ ID NO: 135) | +5 G to A | 12 | 18 | 13 |
| OsCDC48-T2-pegGT | GACCAGCCAGCGTC TGGCGC**CGG** (SEQ ID NO: 136) | TCAGCGGCGGCGCAGG CGCCAGACGCTGGC (SEQ ID NO: 137) | +5 G to T | 12 | 18 | 13 |
| OsCDC48-T2-pegGC | GACCAGCCAGCGTC TGGCGC**CGG** (SEQ ID NO: 138) | TCAGCGGCGGCGCGGG CGCCAGACGCTGGC (SEQ ID NO: 139) | +5 G to C | 12 | 18 | 13 |
| OsCDC48-T2-pegCA | GACCAGCCAGCGTC TGGCGC**CGG** (SEQ ID NO: 140) | TCAGCGGCGGCGCCTG CGCCAGACGCTGGC (SEQ ID NO: 141) | +4 C to A | 12 | 18 | 14 |
| OsCDC48-T2-pegCT | GACCAGCCAGCGTC TGGCGC**CGG** (SEQ ID NO: 142) | TCAGCGGCGGCGCCAG CGCCAGACGCTGGC (SEQ ID NO: 143) | +4 C to T | 12 | 18 | 14 |
| OsCDC48-T2-pegDel | GACCAGCCAGCGTC TGGCGC**CGG** (SEQ ID NO: 144) | TCAGCGGCGGCGGCGC CAGACGCTGGC (SEQ ID NO: 145) | +4-6 CGG del | 12 | 15 | 10 |
| OsCDC48-T2-pegPBS8 | GACCAGCCAGCGTC TGGCGC**CGG** (SEQ ID NO: 146) | GGCGCCGGCTTTGCCA GACGC (SEQ ID NO: 147) | +2 AAA ins | 8 | 13 | 9 |
| OsCDC48-T2-pegPBS10 | GACCAGCCAGCGTC TGGCGC**CGG** (SEQ ID NO: 148) | GGCGCCGGCTTTGCCA GACGCTG (SEQ ID NO: 149) | +2 AAA ins | 10 | 13 | 9 |
| OsCDC48-T2-pegPBS14 | GACCAGCCAGCGTC TGGCGC**CGG** (SEQ ID NO: 150) | GGCGCCGGCTTTGCCA GACGCTGGCTG (SEQ ID NO: 151) | +2 AAA ins | 14 | 13 | 9 |
| OsCDC48-T2-pegPBS16 | GACCAGCCAGCGTC TGGCGC**CGG** (SEQ ID NO: 152) | GGCGCCGGCTTTGCCA GACGCTGGCTGGT (SEQ ID NO: 153) | +2 AAA ins | 16 | 13 | 9 |
| OsCDC48-T2-pegRT10 | GACCAGCCAGCGTC TGGCGC**CGG** (SEQ ID NO: 154) | GCCGGCTTTGCCAGAC GCTGGC (SEQ ID NO: 155) | +2 AAA ins | 12 | 10 | 6 |
| OsCDC48-T2-pegRT11 | GACCAGCCAGCGTC TGGCGC**CGG** (SEQ ID NO: 156) | CGCCGGCTTTGCCAGA CGCTGGC (SEQ ID NO: 157) | +2 AAA ins | 12 | 11 | 7 |
| OsCDC48-T2-pegRT15 | GACCAGCCAGCGTC TGGCGC**CGG** (SEQ ID NO: 158) | GCGGCGCCGGCTTTGC CAGACGCTGGC (SEQ ID NO: 159) | +2 AAA ins | 12 | 15 | 11 |
| OsCDC48-T2-pegRT16 | GACCAGCCAGCGTC TGGCGC**CGG** (SEQ ID NO: 160) | GGCGGCGCCGGCTTTG CCAGACGCTGGC (SEQ ID NO: 161) | +2 AAA ins | 12 | 16 | 12 |
| OsCDC48-T2-pegRT17 | GACCAGCCAGCGTC TGGCGC**CGG** (SEQ ID NO: 162) | CGGCGGCGCCGGCTTT GCCAGACGCTGGC (SEQ ID NO: 163) | +2 AAA ins | 12 | 17 | 13 |
| OsCDC48-T2-pegRT19 | GACCAGCCAGCGTC TGGCGC**CGG** (SEQ ID NO: 164) | AGCGGCGGCGCCGGCT TTGCCAGACGCTGGC (SEQ ID NO: 165) | +2 AAA ins | 12 | 19 | 15 |
| OsCDC48-T2-pegRT21 | GACCAGCCAGCGTC TGGCGC**CGG** (SEQ ID NO: 166) | TCAGCGGCGGCGCCGG CTTTGCCAGACGCTGG C (SEQ ID NO: 167) | +2 AAA ins | 12 | 21 | 17 |
| OsCDC48-T3-peg01 | TAGCACCCATGACA ATGACA**TGG** (SEQ ID NO: 168) | AGCTCGTTCCCGGGTCA TTGTCATGGG (SEQ ID NO: 169) | +2-4 ATG del | 12 | 15 | 11 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| OsDEP1-peg01 | GTGGGTTTGTTTCTA GCTCA**AGG** (SEQ ID NO: 170) | ATTTCCTCCTTAAGCTA GAAACAAAC (SEQ ID NO: 171) | +2 C to T | 13 | 13 | 11 |
| OsDEP1-peg02 | GTGGGTTTGTTTCTA GCTCA**AGG** (SEQ ID NO: 172) | ATTTCCTCCTCGAGCTA GAAACAAAC (SEQ ID NO: 173) | +3 A to G | 13 | 13 | 10 |
| OsEPSPS-T1-peg01 | TACTAAATATACAAT CCCTT**GGG** (SEQ ID NO: 174) | ATAAACCCATGGGATTG TATATTT (SEQ ID NO: 175) | +2 T to A | 13 | 11 | 9 |
| OsEPSPS-T1-peg02 | TACTAAATATACAAT CCCTT**GGG** (SEQ ID NO: 176) | TGGAAACAAATAAACA CAAGGGATTGTATATTT (SEQ ID NO: 177) | +5 G to T | 13 | 20 | 16 |
| OsEPSPS-T2-peg01 | GAAAATATGTATGG AATTCA**TGG** (SEQ ID NO: 178) | ATAAAACATACCCCATT AATTCCATACATAT (SEQ ID NO: 179) | +2 C to A | 13 | 17 | 15 |
| OsGAPDH-peg01 | GAGTATGTCGTGGA GTCCAC**CGG** (SEQ ID NO: 180) | AGTGAAGACACCGTTG GACTCCACGACA (SEQ ID NO: 181) | +3 C to A | 12 | 16 | 13 |
| OsGAPDH-pegCT | GAGTATGTCGTGGA GTCCAC**CGG** (SEQ ID NO: 182) | AGTGAAGACACCGATG GACTCCACGACA (SEQ ID NO: 183) | +3 C to T | 12 | 16 | 13 |
| OsGAPDH-pegCG | GAGTATGTCGTGGA GTCCAC**CGG** (SEQ ID NO: 184) | AGTGAAGACACCGCTG GACTCCACGACA (SEQ ID NO: 185) | +3 C to G | 12 | 16 | 13 |
| OsGAPDH-pegAT | GAGTATGTCGTGGA GTCCAC**CGG** (SEQ ID NO: 186) | AGTGAAGACACCGGAG GACTCCACGACA (SEQ ID NO: 187) | +2 A to T | 12 | 16 | 14 |
| OsGAPDH-pegAC | GAGTATGTCGTGGA GTCCAC**CGG** (SEQ ID NO: 188) | AGTGAAGACACCGGGG GACTCCACGACA (SEQ ID NO: 189) | +2 A to C | 12 | 16 | 14 |
| OsGAPDH-pegAG | GAGTATGTCGTGGA GTCCAC**CGG** (SEQ ID NO: 190) | AGTGAAGACACCGGCG GACTCCACGACA (SEQ ID NO: 191) | +2 A to G | 12 | 16 | 14 |
| OsGAPDH-pegGA | GAGTATGTCGTGGA GTCCAC**CGG** (SEQ ID NO: 192) | AGTGAAGACACTGGTG GACTCCACGACA (SEQ ID NO: 193) | +5 G to A | 12 | 16 | 11 |
| OsGAPDH-pegGT | GAGTATGTCGTGGA GTCCAC**CGG** (SEQ ID NO: 194) | AGTGAAGACACAGGTG GACTCCACGACA (SEQ ID NO: 195) | +5 G to T | 12 | 16 | 11 |
| OsGAPDH-pegGC | GAGTATGTCGTGGA GTCCAC**CGG** (SEQ ID NO: 196) | AGTGAAGACACAGGTG GACTCCACGACA (SEQ ID NO: 197) | +5 G to C | 12 | 16 | 11 |
| OsGAPDH-pegTA | GAGTATGTCGTGGA GTCCAC**CGG** (SEQ ID NO: 198) | AGTGAAGACTCCGGTG GACTCCACGACA (SEQ ID NO: 199) | +7 T to A | 12 | 16 | 9 |
| OsGAPDH-pegTC | GAGTATGTCGTGGA GTCCAC**CGG** (SEQ ID NO: 200) | AGTGAAGACGCCGGTG GACTCCACGACA (SEQ ID NO: 201) | +7 T to C | 12 | 16 | 9 |
| OsGAPDH-pegTG | GAGTATGTCGTGGA GTCCAC**CGG** (SEQ ID NO: 202) | AGTGAAGACCCCGGTG GACTCCACGACA (SEQ ID NO: 203) | +7 T to G | 12 | 16 | 9 |
| OsLDMAR-peg01 | GTGCATCCTGGGAA AGCTTG**TGG** (SEQ ID NO: 204) | AAACTTGCTACCACTAG CTTTCCCAGGA (SEQ ID NO: 205) | +2 T to A | 12 | 15 | 14 |

TABLE 1-continued

List of the pegRNA targeting sites and the RT and PBS sequences

| pegRNA | Target site sequence | RT template and PBS sequence | Editing type | PBS length | RT length | Homologous arm length |
|---|---|---|---|---|---|---|
| TaGW2-peg01 | CACAAGAAAATCCA CCAGGA**TGG** (SEQ ID NO: 206) | ATGCCCCATCGTGGTGG ATTTT (SEQ ID NO: 207) | +1 G to C | 11 | 11 | 10 |
| TaUbi10-T1-peg01 | GCGTATGTATGAAA CTGTAC**AGG** (SEQ ID NO: 208) | AGAAAAGGCTCCAGTA CAGTTTCATACAT (SEQ ID NO: 209) | +4 A to T | 13 | 16 | 12 |
| TaUbi10-T2-peg01 | GCTGGTGCAACTGG TGGCCC**AGG** (SEQ ID NO: 210) | AGCCCTCCTGGCCCAC CAGTTGCA (SEQ ID NO: 211) | +1 C to G | 12 | 12 | 11 |
| TaLOX2-peg01 | GTGCCGCGCGACGA GCTCTT**CGG** (SEQ ID NO: 212) | TGAGGTGGCCGAACAG CTCGTCGCGC (SEQ ID NO: 213) | +1 C to G | 12 | 14 | 13 |
| TaMLO-peg01 | GGAGATTGGGTCCT GCGTGA**CGG** (SEQ ID NO: 214) | TGCTCGCCGTCCCGCA GGACCCAA (SEQ ID NO: 215) | +1 T to G | 12 | 12 | 11 |
| TaDME- peg01 | TTTGATGGTTTCAG GACCTT**TGG** (SEQ ID NO: 216) | AGCACAGGCCAAATGT CCTGAAACCAT (SEQ ID NO: 217) | +1 C to A | 13 | 14 | 13 |
| TaGASR7-peg01 | GCCGGGCACCTACG GCAACA**AGG** (SEQ ID NO: 218) | AGGGGCAGGCGCGCTT GTTGCCGTAGGTGC (SEQ ID NO: 219) | +6 G to C | 12 | 18 | 12 |

The PAM sequence is shown in bold.

2. Protoplast Isolation and Transformation

The protoplasts used in the present invention were derived from the rice variety Zhonghua 11 and the wheat variety Kenong 199.

2.1 Cultivation of Rice Seedlings

Seeds were first rinsed with 75% ethanol for 1 min, then treated with 4% sodium hypochlorite for 30 min, and washed with sterile water for more than 5 times. The treated seeds were cultured on a M6 culture medium for 3-4 weeks at 26° C., and protected from light.

2.2 Isolation of Rice Protoplasts (1) Rice stalks were cut off and the middle parts thereof were cut into 0.5-1 mm filaments with a blade. The filaments were treated with a 0.6 M mannitol solution for 10 min in the dark, filtered with a filter, put into 50 mL an enzymolysis solution (filtered with a 0.45 μm membrane), vacuumized (pressure intensity of about 15 Kpa) for 30 min, taken out and placed on a shaker (10 rpm) for enzymolysis at room temperature for 5 h.

(2) The enzymolysis product was diluted by adding 30-50 mL W5 and filtered with a 75 μm nylon filter membrane into a round-bottomed centrifuge tube (50 mL).

(3) Centrifugation was conducted at 23° C. for 3 min at 250 g (rcf) prior to discarding the supernatant.

(4) The cells were slightly suspended with 20 mL W5, and step (3) was repeated.

(5) An appropriate amount of MMG was added to suspend the cells for transformation.

2.3 Transformation of Rice Protoplasts (1) 10 μg vector to be transformed was added to each 2 mL centrifuge tube and mixed well. 200 μL protoplasts were taken with a tipped pipette and mixed well by flicking. 220 μL PEG4000 solution was added and mixed well by flicking, followed by inducing transformation for 20-30 min at room temperature in the absence of light.

(2) 880 μL W5 was added and mixed well by slight inverting, and centrifugation was conducted at 250 g (rcf) for 3 min prior to discarding the supernatant.

(3) 1 mL WI solution was added and mixed well by gently inverting before being gently transferred to a flow tube and cultured in the dark at 26° C. for 48 h. Protoplasts to be treated at 37° C. should be transferred to the flow tube for culturing in the dark at 26° C. for 12 h, then transferred to a dark place at 37° C. for 8 h, and finally transferred to a place at 26° C. for culturing for 48 h.

2.4 Cultivation of Wheat Seedlings

Potted wheat seeds were planted in a culture room for culturing (about 10 days) at 25±2° C. with a light intensity of 1000 Lx and illumination time of 14-16 h/d for about 1-2 weeks.

2.5 Isolation of Wheat Protoplasts (1) The young leaves of wheat were obtained and the middle parts thereof were cut into 0.5-1 mm filaments with a blade. The filaments were treated with a 0.6 M mannitol solution for 10 min in the dark, filtered with a filter screen, put into 50 mL enzymolysis solution (filtered with a 0.45 μm filter membrane), vacuumized (pressure intensity of about 15 Kpa) for 30 min, taken out and placed on a shaker (10 rpm) for enzymolysis at room temperature for 5 h.

(2) The enzymolysis product was diluted by adding 30-50 mL W5 and filtered with 75 μm nylon filter membrane into a round-bottomed centrifuge tube (50 mL).

(3) Centrifugation was conducted at 23° C. for 3 min at 100 g (rcf) prior to discarding the supernatant. (4) The cells were slightly suspended with 10 mL W5 and placed on ice for 30 min. The protoplasts were gradually settled, and the supernatant was discarded. (5) The resulting product was suspended with an appropriate amount of MMG and placed on ice until transformation.

2.6 Transformation of Wheat Protoplasts (1) 10 μg plasmids to be transformed were added into each 2 mL centrifuge tube, and mixed well.

(2) 200 μL protoplasts were sucked with a tipped pipette and mixed well by flicking. 250 μL PEG4000 solution was added immediately and mixed well by flicking, followed by inducing transformation for 20-30 min at room temperature in the absence of light.

(3) 800 μL W5 (room temperature) was added and mixed well by slight inverting, and centrifugation was conducted at 100 g (rcf) for 3 min prior to discarding the supernatant.

(4) 1 mL W5 was added, mixed well by slight inverting and gently transferred to a 6-well plate wrapped with foil in which 1 mL W5 has been added. The cells were incubated in the dark at 26° C. for 48 h.

3. Observation of Cell Fluorescence by Flow Cytometer

The FACSAria III (BD Biosciences) instrument for the flow cytometry analysis of protoplasts has the following specific operation steps:

(1) After the instrument was turned on, the BD FACSDiva Software was started for the operation such as instrument calibration.

(2) "New Protocol" was clicked to create a suitable experimental protocol.

(3) "Density plot" was selected to draw a FSC/SSC scatter diagram and a GFP/PE-Texas Red scatter diagram.

(4) The FSC/SSC voltage was adjusted to make the cell population appear in the center of the scatter diagram, the FL1 voltage was adjusted to make the wild-type control protoplast population appear in the center of the scatter diagram, and the GFP-positive protoplast population will appear in the location where the GFP fluorescence channel signal is higher (there is no such population in the wild-type control sample). If necessary, compensated regulation was made, so that the GFP-negative and GFP-positive protoplast populations are more distinct.

(5) A gate was set to circle the GFP-positive population. A protoplast-negative control needs to be prepared to determine the boundary of the gate.

(6) The cell population to be sorted was clicked by the right button, the "left sort" was selected, and the analysis condition and the analysis mode were set according to the experimental needs and the percentage of target cells.

(7) The prepared protoplast samples cultured in the flow tube were sampled sequentially, and relevant data was recorded for analysis.

(8) Both the software and the instrument were shut down.

4. Protoplast DNA Extraction and Amplicon Sequencing Analysis 3.1 Protoplast DNA Extraction The protoplasts were collected in a 2 mL centrifuge tube, and protoplast DNA (~30 μL) with a concentration (30-60 ng/μL) measured by a NanoDrop ultra-micro spectrophotometer was extracted by a CTAB method and stored at −20° C.

3.2 Amplicon Sequencing Analysis (1) PCR amplification was conducted on a protoplast DNA template using genomic primers. A 20 μL amplification system comprised 4 μL 5× Fastpfu buffer, 1.6 μL dNTPs (2.5 mM), 0.4 μL Forward primer (10 μM), 0.4 μL Reverse primer (10 μM), 0.4 μL FastPfu polymerase (2.5 U/μL), and 2 μL DNA template (~60 ng). The amplification condition was as followings: pre-denaturation at 95° C. for 5 min; denaturation at 95° C. for 30 s, annealing at 50-64° C. for 30 s, extension at 72° C. for 30 s, for 35 cycles; fully extending at 72° C. for 5 min, and storing at 12° C.

(2) The above amplification product was diluted by 10 times, 1 μL amplification product was taken as a second PCR amplification template, and the amplification primers were sequencing primers containing Barcode. A 50 μL amplification system comprised 10 μL 5× Fastpfu buffer, 4 μL dNTPs (2.5 mM), 1 μL Forward primer (10 μM), 1 μL Reverse primer (10 μM), 1 μL FastPfu polymerase (2.5 U/μL), and 1 μL DNA template. The amplification condition was the same as that mentioned above, and the number of amplification cycles was 35 cycles.

(3) The PCR product was separated by 2% agarose gel electrophoresis, and gel extraction was conducted on a target fragment using the AxyPrep DNA Gel Extraction kit, and the resulting product was quantitatively analyzed using a NanoDrop ultra-micro spectrophotometer. The 100 ng recovered product was taken, mixed and sent to the Sangon Bioengineering Co., Ltd. for amplicon sequencing library construction and amplicon sequencing analysis.

(4) After sequencing was completed, the original data were split according to the sequencing primers, and WT was used as a control to compare and analyze the editing type and editing efficiency of the products at different genetic target loci in three repeated trials.

Figure 2:
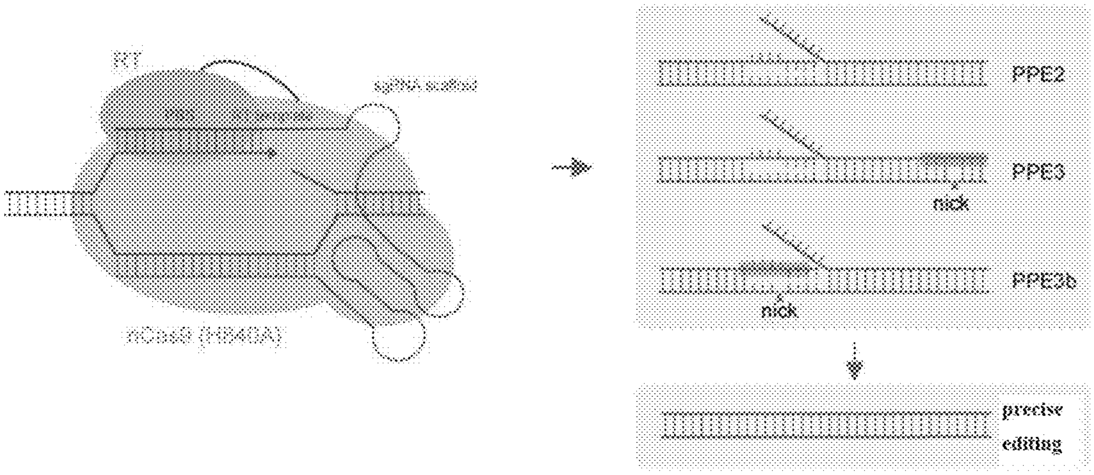
FIG. 2 shows a working schematic diagram of three different kinds of PPE (plant prime editor) systems. The system that does not provide an additional nicking sgRNA is named (PPE2); the system that provides an additional nicking sgRNA that facilitates cleavage of opposite strand of pegRNA is named (PPE3); and when the PAM sequence of the nicking sgRNA that cleaves the opposite strand is located within the spacer sequence of the pegRNA, the system is named (PPE3b).
Figure 3:
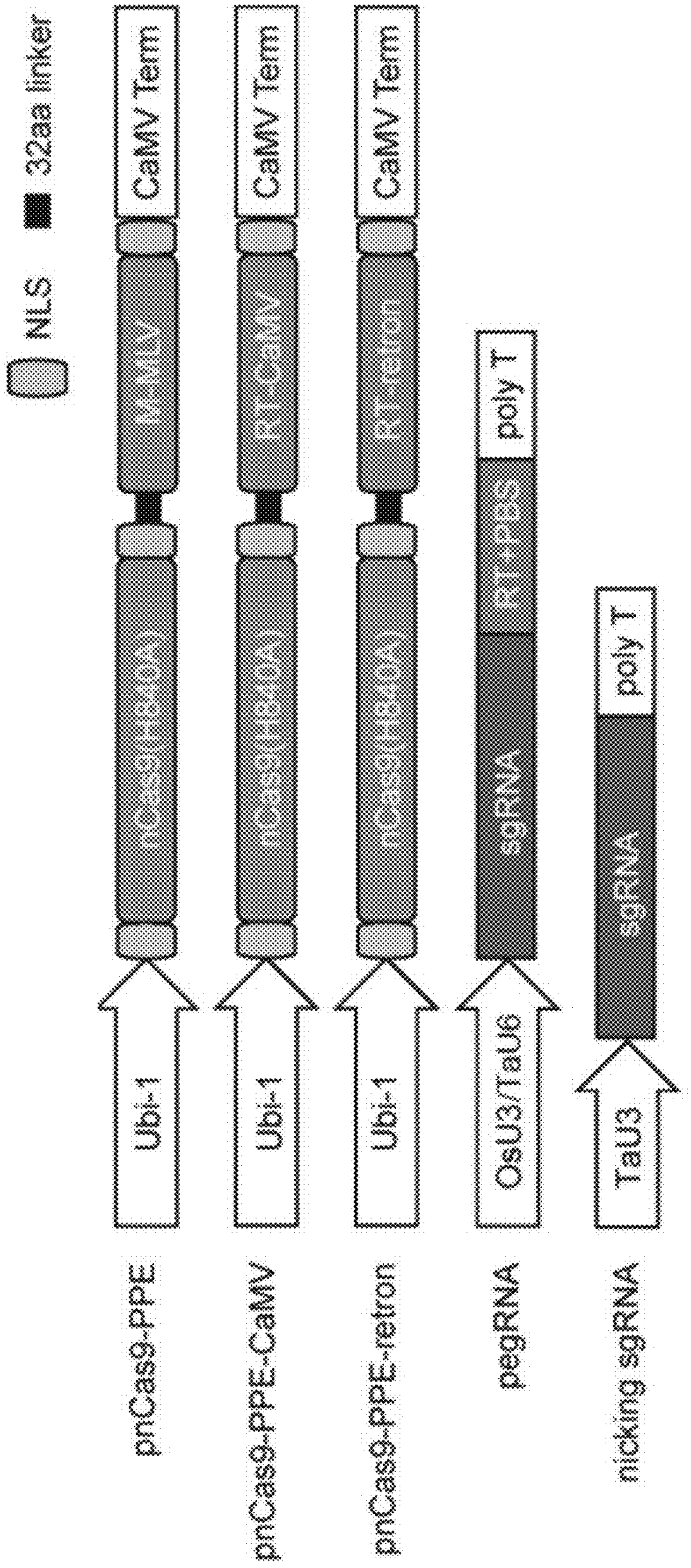
FIG. 3 shows a schematic diagram of the PPE constructs and pegRNA constructs.
Figure 4:
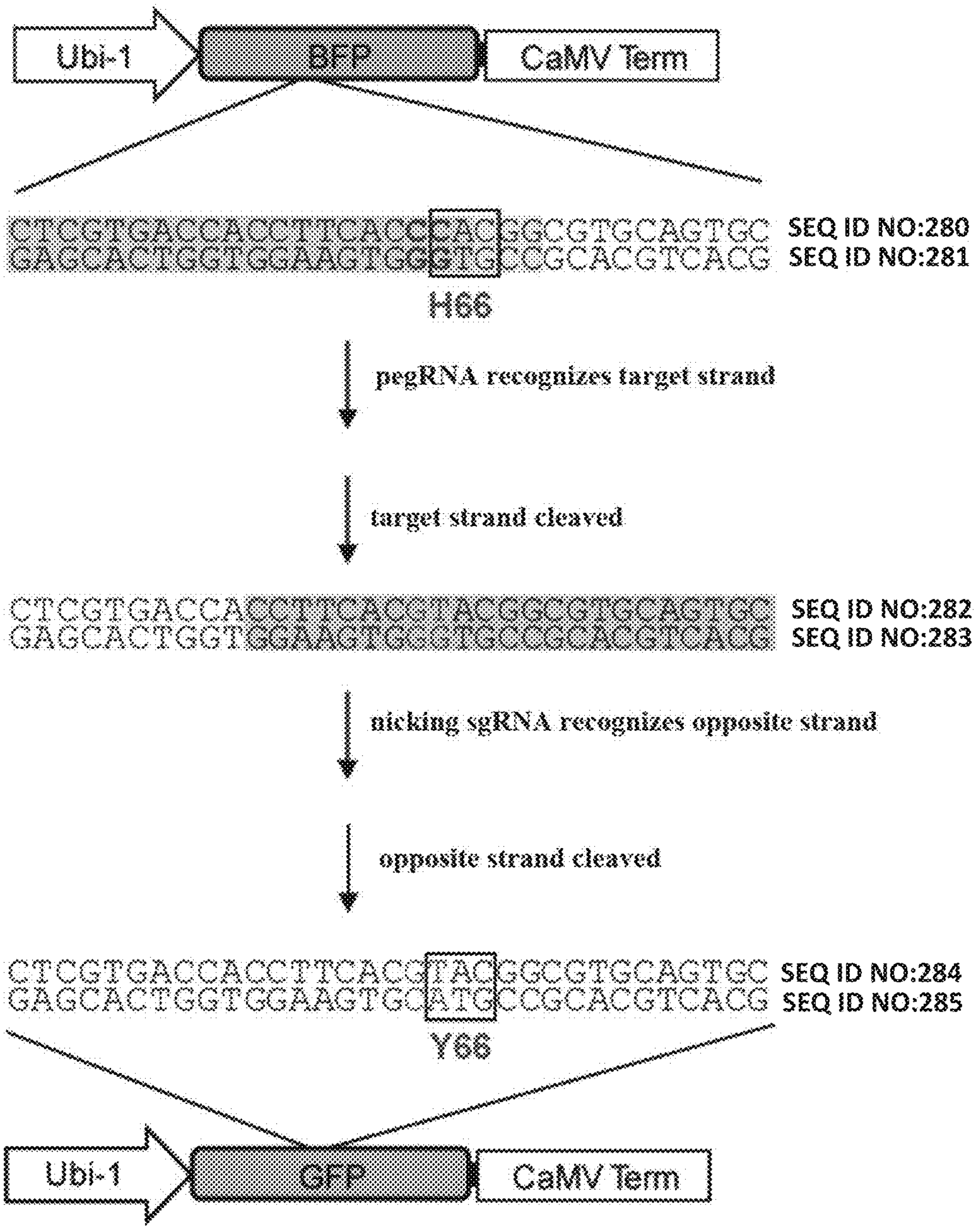
FIG. 4 shows a working mechanism of a BFP-to-GFP reporting system for detecting precise editing in plant protoplasts.
Figure 5:
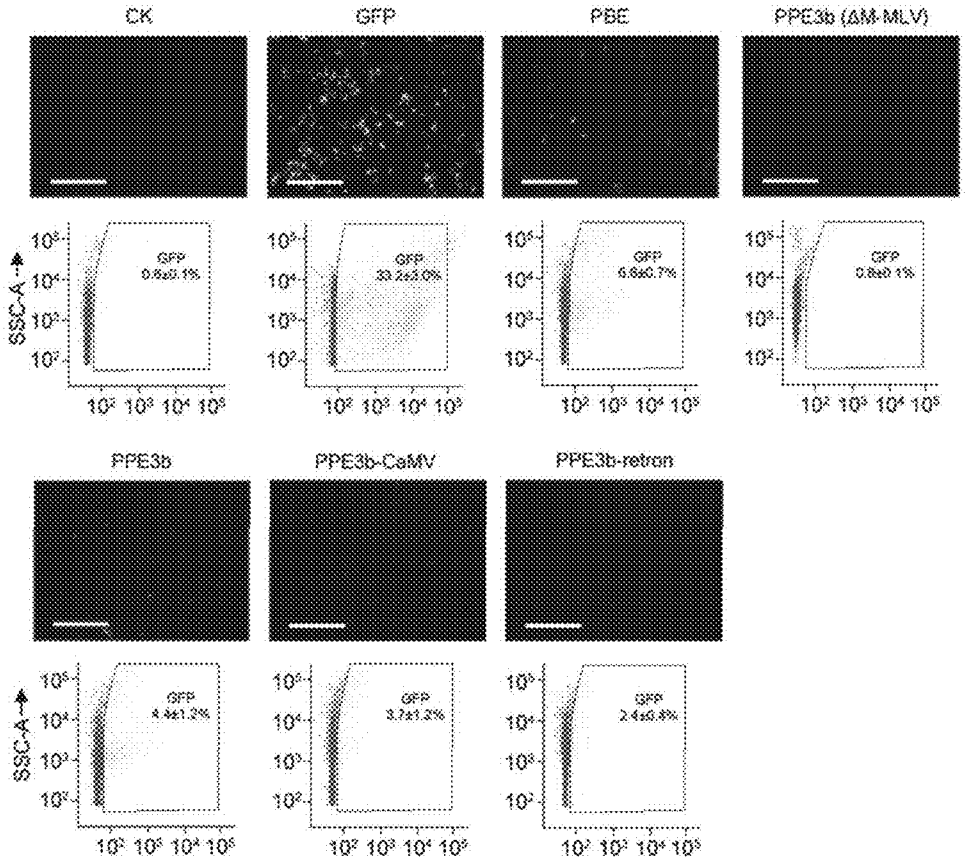
FIG. 5 shows a result diagram of fluorescence intensity measured by a flow cytometer for the PPE systems. "CK" is a protoplast control without plasmid transformation, "PBE" is a BE3 single base editing system, and "PPE3b (A M-MLV)" represents a control group lacking an M-MLV reverse transcriptase.
Figure 6:
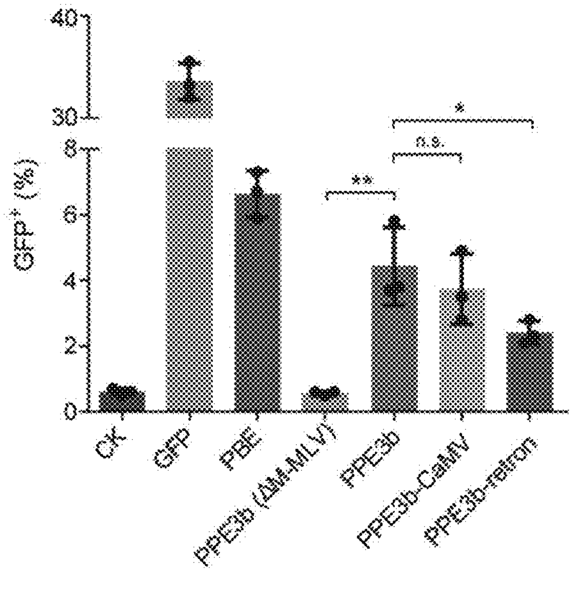
FIG. 6 shows efficiency the PPE systems measured by Flow Cytometry. The "CK" is the protoplast control without plasmid transformation, the "PBE" is the BE3 single base editing system, and the "PPE3b (A M-MLV)" represents the control group lacking the M-MLV reverse transcriptase.

Example 1 BFP-to-GFP Reporter System in Rice Protoplasts Precisely Modified by Cas9 (H840A) Nickase-Reverse Transcriptase Fusion System In order to test whether Cas9 (H840A) nickase-reverse transcriptase fusion (PPEs, plant prime editors) can be used to precisely modify a target sequence (FIGS. 1-2) or not, an nCas9(H840A)-M-MLV construct (PPE-M-MLV), an nCas9(H840A)-CaMV construct (PPE-CaMV), an nCas9 (H840A)-retron (PPE-retron) construct, an OsU3/TaU6-promoter-driven pegRNA construct with target guide RNA and RT and PBS sequences, and a TaU3-promoter-driven nicking gRNA construct that nicks a non-target strand (FIG. 3) were constructed. The performance of PPEs in the protoplasts was observed by the BFP-to-GFP reporter system (FIG. 4). When the "CC" in the BFP gene sequence was changed into "GT", the 66th amino acid can be changed from histidine (H, Histidine) to tyrosine (Y, Tyrosine), so that the gene encodes GFP fluorescent protein and the cells emitted green fluorescence. The efficiency of PPEs can then be analyzed by a flow cytometry. The results show that PPE lacking a reverse transcriptase (i.e., PPE3b (ΔM-MLV)) failed to make the cells emit green fluorescence, while green fluorescence can be clearly observed in the cells after co-transforming the PPE-M-MLV, the pegRNA, the nicking gRNA and the BFP-to-GFP reporter system (i.e., PPE3b) into the protoplasts, and the average efficiency is 4.4% (FIGS. 5-6). Replacing the M-MLV reverse transcriptase in this system with a reverse transcriptase (i.e., PPE3b-CaMV) derived from CaMV viruses or a reverse transcriptase (i.e., PPE3b-retron) derived from a bacterial retron system can also make the cells emit green fluorescence, and the efficiency was 3.7% and 2.4%, respectively (FIGS. 5-6). Therefore, the above results demonstrate the ability of PPEs in plants to allow desired specified modifications of the target sequence of the reporter system, which preliminarily demonstrates that PPEs can work in plants. PPE may comprise reverse transcriptase of other forms and sources.

Figure 7:
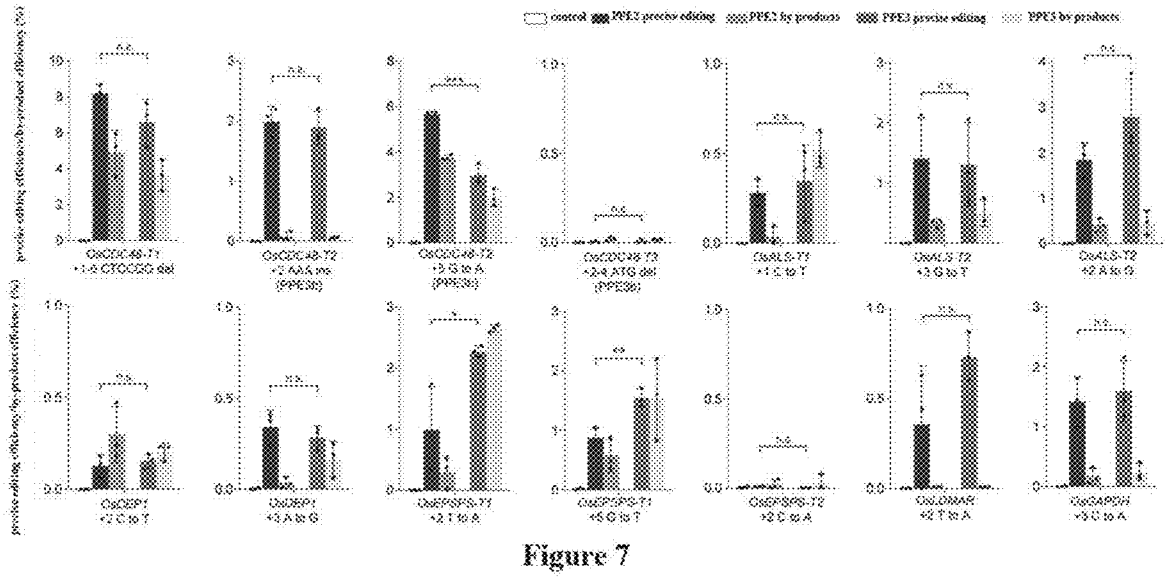
FIG. 7 shows editing by the PPE systems at rice endogenous targets.
Figure 8:
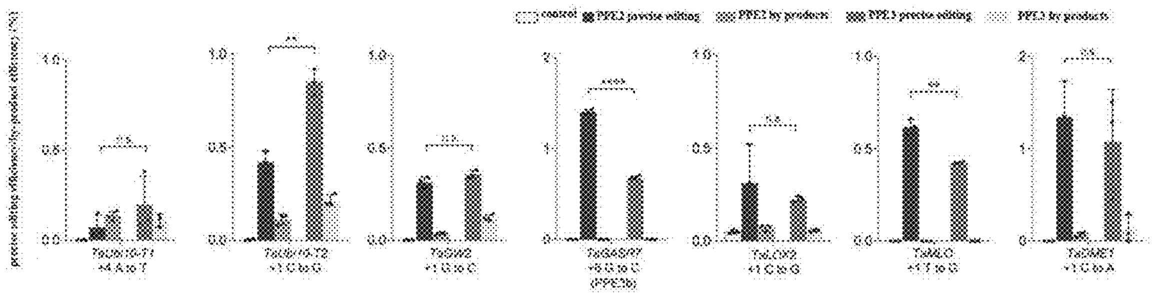
FIG. 8 shows editing by the PPE systems at wheat endogenous targets.
Figure 9:
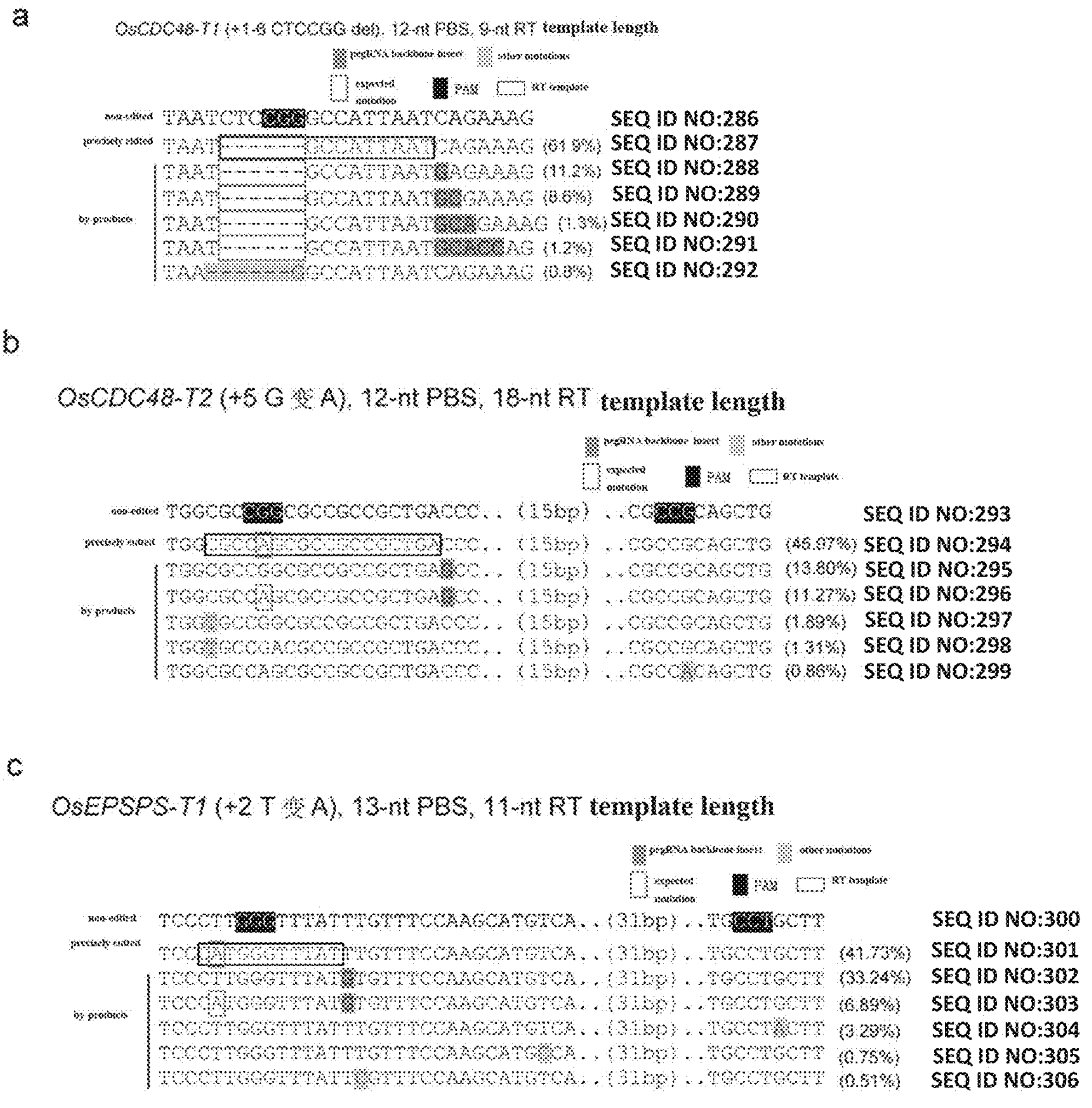
FIG. 9 shows byproducts produced by the PPE systems and their ratios.

Example 2 Genome Sequences in Rice and Wheat Protoplasts Precisely Modified by Cas9(H840A) Nickase-Reverse Transcriptase Fusion System In order to test whether the PPE system can work on endogenous loci in rice or not, 21 pegRNAs were designed and constructed for 10 endogenous loci in rice (OsCDC48-T1, OsCDC48-T2, OsCDC48-T3, OsALS-T1, OsALS-T2, OsDEP1, OsEPSPS-T1, OsEPSPS-T2, OsLDAMR and OsGAPDH) and 7 endogenous loci in wheat (TaUbi10-T1, TaUbi10-T2, TaGW2, TaGASR7, TaLOX2, TaMLO and TaDME) to test whether PPE2 and PPE3 (or PPE3b) can work on these endogenous loci or not. The results indicate that both the PPE2 and PPE3 (or PPE3b) systems can achieve specific single-base changes including C-to-T, G-to-T, A-to-G, G-to-A, T-to-A and C-to-A on the endogenous loci in rice, as well as addition or deletion of specific bases, and the system has the highest efficiency of 8.2% in rice (FIG. 7). The PPE2 and PPE3 (or PPE3b) systems can also achieve single-base changes including A to T, C to G, G to C, T to G and C to A on the endogenous loci in wheat, and the highest efficiency is 1.4% (FIG. 8). The overall efficiency of PPE2 and PPE3 (or PPE3b) did not differ significantly on the loci tested. In addition, a proportion of by-products were also observed in the PPE system, mainly including insertion or substitution of the pegRNA skeleton (FIG. 9). The above results indicate that the PPE systems including PPE2, PPE3 and PPE3b can achieve targeted modification including precise single-base mutation, precise insertion and precise deletion on the endogenous loci in plants.

Figure 10:
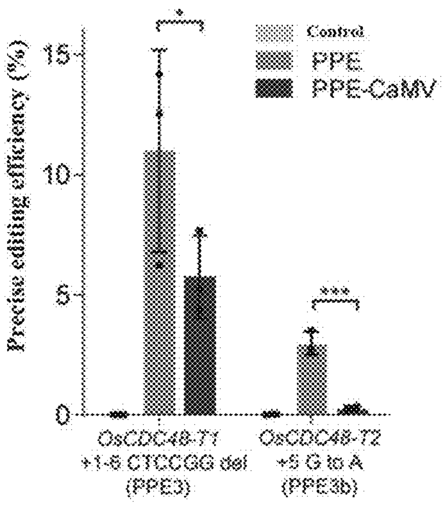
FIG. 10 shows editing by a PPE-CaMV system in plant endogenous targets.

Example 3 Improvement of Cas9 (H840A) Nickase-Reverse Transcriptase Fusion System In order to further improve the PPE editing system, the performance of the PPE-CaMV system on the endogenous loci in rice was tested. The results showed that PPE-CaMV can also achieve precise targeted modification of endogenous sequences in rice, with the highest efficiency of 5.8% (FIG. 10), and indicated that PPE systems derived from other species or other forms of reverse transcriptases also can modify endogenous genes in plants in a targeted manner.

Figure 11:
FIG. 11 shows a schematic diagram of the pegRNAs initiated by type II promoters and processed by ribozymes.
Figure 12:
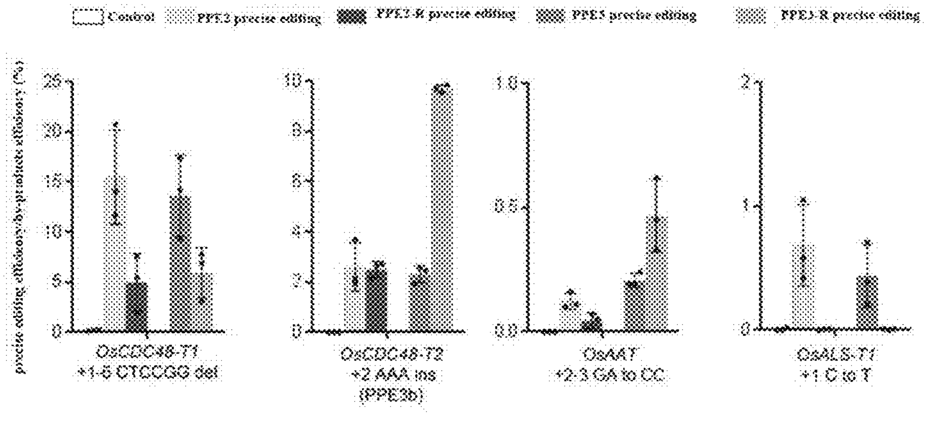
FIG. 12 shows editing by a PPE-R system in plant endogenous genes.

In addition, the performance of a ribozyme-processed pegRNA in the PPE system was also tested. An Ubi-1-driven ribozyme-processed pegRNA construct with target guide RNA and RT and PBS sequences was constructed to replace an OsU3-driven pegRNA construct in the original system, and this system was named as PPE-R (R represents Ribozyme) (FIG. 11). The results of endogenous targets showed that the strategy of using ribozyme processing can also achieve precise change of the endogenous sequences. PPE-R was improved compared with PPE on some loci, and the highest efficiency can be 9.7% (FIG. 12). This result suggests that both the ribozyme-processed pegRNA and using type II promoters to drive the transcription of pegRNA are suitable for use in the PPE system.

Figure 13:
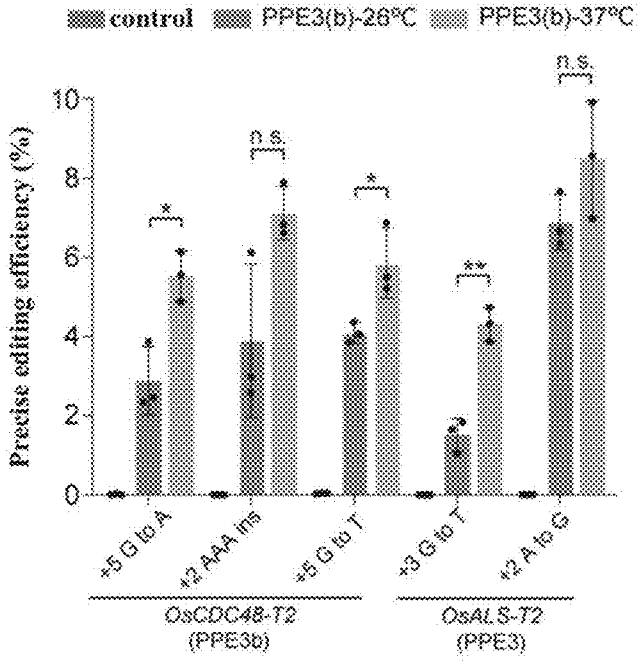
FIG. 13 shows temperature treatments for improving editing efficiency of the PPE systems.

In order to improve the editing efficiency of the PPE system, the protoplasts were cultured at 37° C. to test whether it can improve the editing efficiency or not. 2 endogenous loci (OsCDC48-T2 and OsALS-T2) in rice were selected for testing. The transformed protoplasts were cultured at 26° C. overnight, incubated at 37° C. for 8 h and cultured at 26° C. again, and then compared with the treatment group in the aspect of efficiency. The results showed that treatment at 37° C. can significantly improve the editing efficiency of the PPE systems (including PPE2, PPE3 and PPE3b), the average efficiency was increased by 1.6 times (from 3.9% to 6.3%), and the highest editing efficiency was increased by 2.9 times (FIG. 13).

Figure 14:
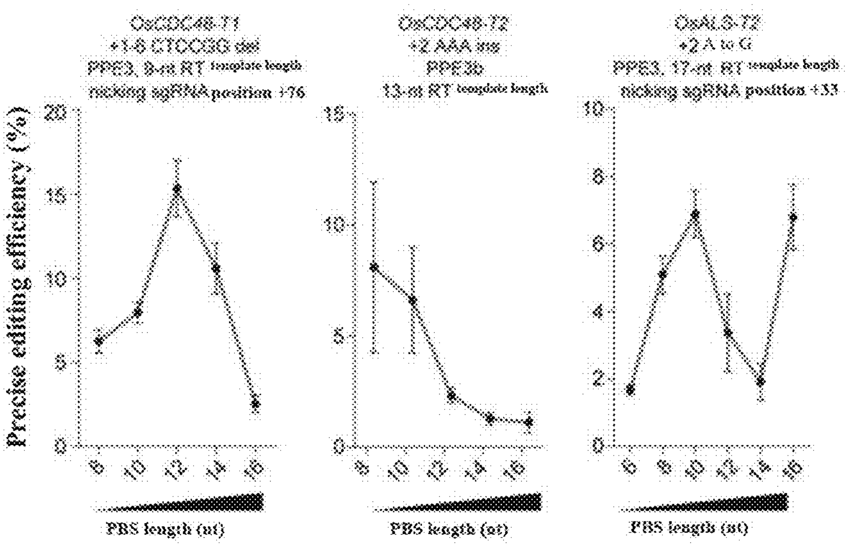
FIG. 14 shows influences of different PBS lengths on the PPE systems.
Figure 15:
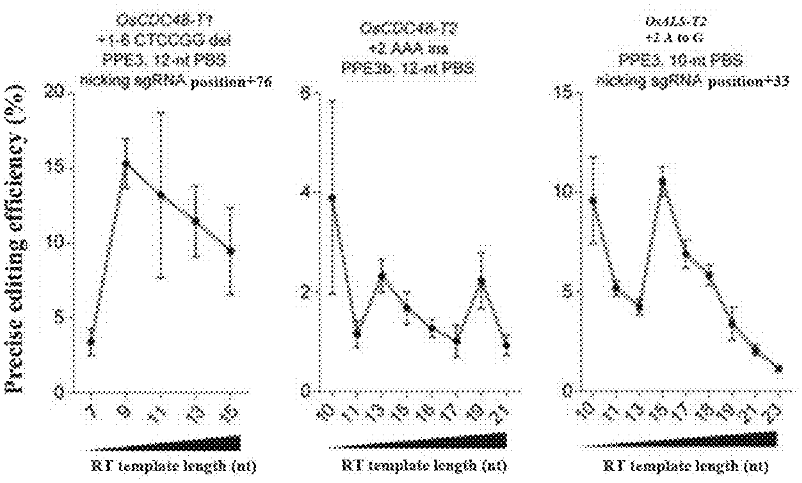
FIG. 15 shows influences of different RT template lengths on the PPE systems.
Figure 16:
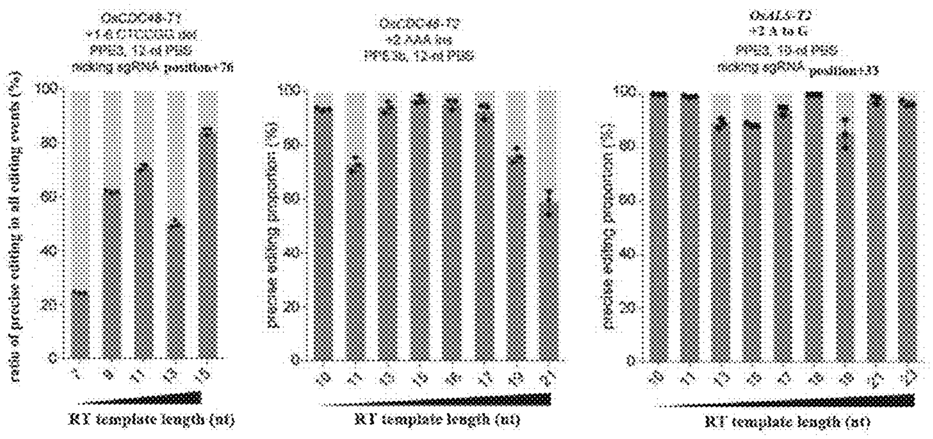
FIG. 16 shows influences of the different RT template lengths on the precise editing ratio of the PPE systems.
Figure 17:
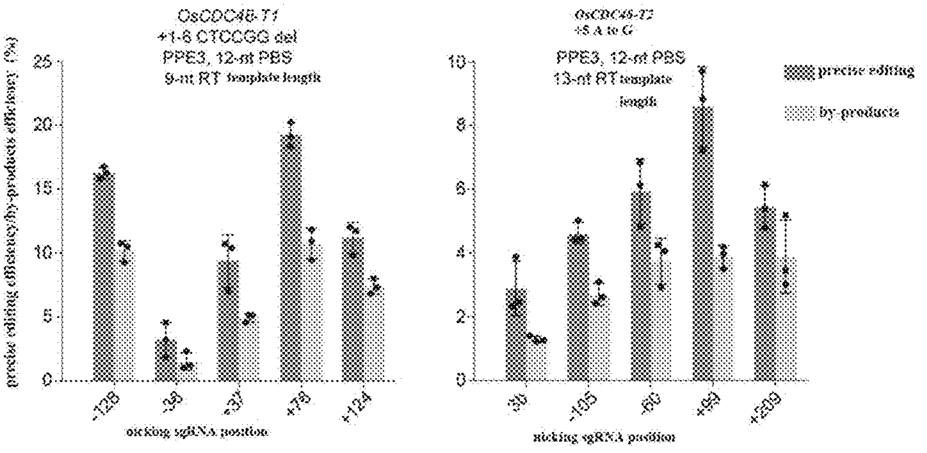
FIG. 17 shows influences of different nicking sgRNA locations on the PPE systems.

Example 4 Influences of Different Lengths of PBS and RT Template and Different Nicking gRNA Positions on the PPE System The influences of different lengths of PBS and RT templates and different nicking gRNA positions on the PPE system were tested. The results using OsCDC48-T1 as a test locus showed that different lengths of PBS (6-16 nt) and RT templates (7-23 nt) tested can lead to a targeted sequence modification on the specific loci (FIGS. 14-15), and the efficiency is 3.4% to 15.3% on the OsCDC48-T1 locus, 0.9% to 8.1% on the OsCDC48-T2 locus, and 1.1% to 10.5% on the OsALS-T2 locus. The results showed that different lengths of RT templates and PBS have a significant effect on the editing efficiency, and it was found that RT templates of different lengths have a relatively significant effect on the proportion and type of by-products produced in the PPE system (FIG. 16). In addition, different nicking gRNAs also affected the efficiency of the PPE system, and the efficiency is 3.2% to 19.2% on the OsCDC48-T1 locus and 2.9% to 8.6% on the OsCDC48-T2 locus (FIG. 17).

Figure 18:
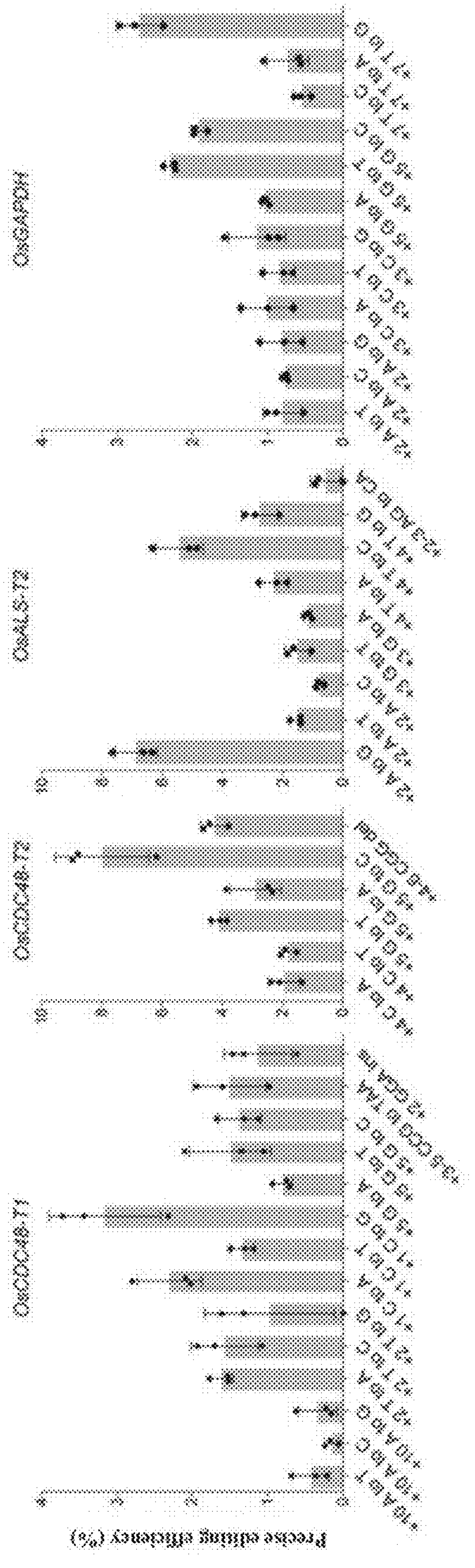
FIG. 18 shows different types of mutations achieved by the PPE systems in the plant endogenous genes.
Figure 19:
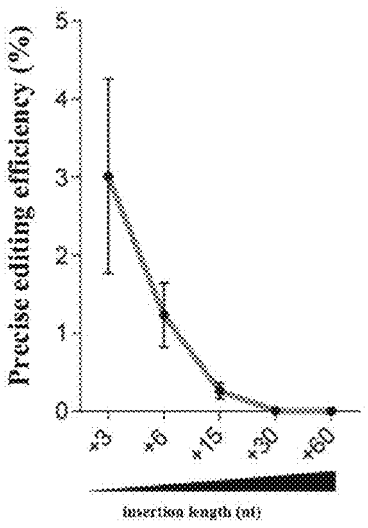
FIG. 19 shows insertions of fragments of different lengths by the PPE systems in the plant endogenous genes.
Figure 20:
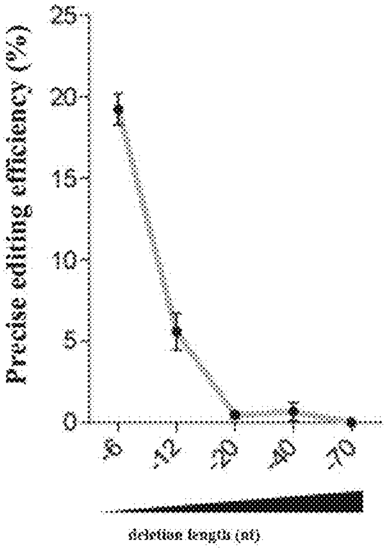
FIG. 20 shows deletions of fragments of different lengths by the PPE systems in the plant endogenous genes.

Example 5 Various Types of Precise Modifications of Endogenous Loci Achieved by PPE System In order to test whether the PPE systems can achieve various types of precise modifications or not, 12 types of single-base changes (N to N, wherein N represents four base types A, T, C or G), multiple bases change, and insertion and deletion of bases of different lengths were designed using 4 loci (OsCDC48-T1, OsCDC48-T2, OsALS-T2 and OsGAPDH) in rice as examples. The results showed that the PPE system can achieve all types of single-base changes with the highest efficiency of 8.0%. The system can also achieve simultaneous change of multiple bases, with the highest efficiency of 1.5% (FIG. 18). The efficiency of base insertion and deletion is decreased with the increase of the length needed to be modified, and the highest targeted insertion efficiency can be 3.0%, and the longest insertion length can be 15 nt (FIG. 19). The highest targeted deletion efficiency can be 19.2%, and the longest deletion length can be 40 nt (FIG. 20). Therefore, the system can efficiently achieve addition and deletion of small segments. Therefore, the PPE system can enable various types of targeted modification of endogenous loci.

Example 6 Targeted Edited Plants Obtained by PPE System

Figure 21:
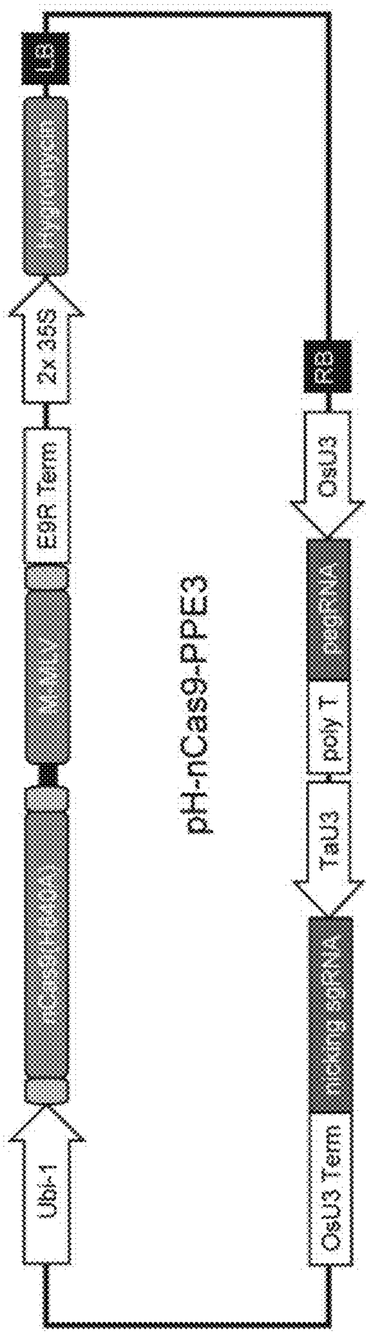
FIG. 21 shows a schematic diagram of the PPE constructs for rice *agrobacterium* infection.
Figure 22:
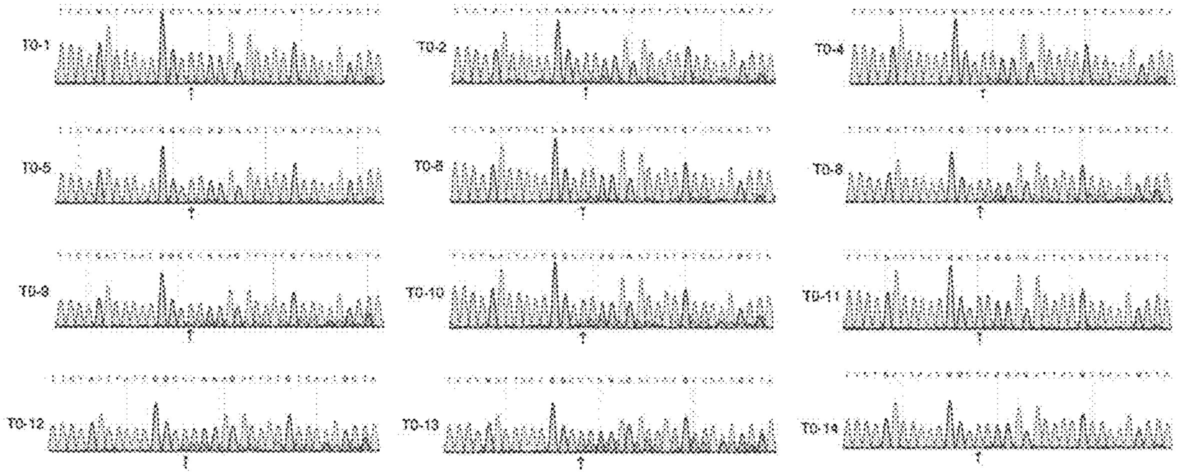
FIG. 22 shows obtaining of rice mutants and sequencing results thereof by using the PPE systems, and the arrow indicates the location of a target mutation.
Figure 22:
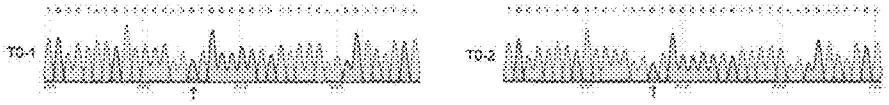
Figure 22:
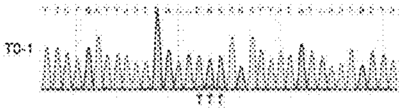
Figure 23:
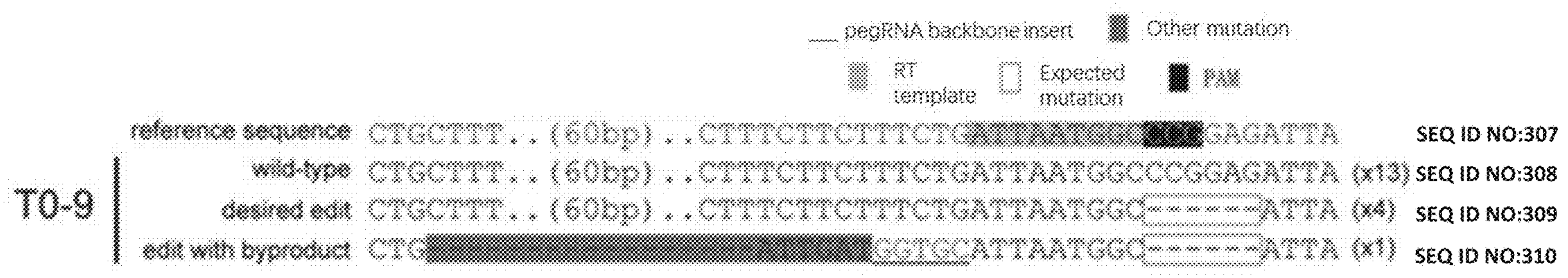
FIG. 23 shows monoclonal sequencing results of T0-9 mutant plants.

In order to obtain targeted edited plants, OsCDC48-T1 and OsALS-T2 loci were selected for testing, a binary vector PPE3 was constructed (FIG. 21), and the rice was infected by *agrobacterium*-mediated transformation. Finally, 12 rice seedlings with the expected precise deletion on the OsCDC48-T1 locus with an editing efficiency of 21.8% (12/55), 2 rice seedlings with the expected single-base mutation of G to T on the OsALS-T2 locus with an editing efficiency of 14.3% (2/14), and 1 rice seedling with the expected precise simultaneous mutation of 3 pairs of bases on the OsCDC48-T1 locus with an editing efficiency of 2.6% (1/38) (FIG. 22) (Table 2) were detected. It was also found that a very small amount of unintended by-products were produced in plants (FIG. 23). The above results indicated that the PPE system can obtain mutant plants with targeted modifications therein.

TABLE 2

| Targeted edited rice obtained by PPE system | | | | | | | |
|---|---|---|---|---|---|---|---|
| Target locus | Target type | PBS length | RT length | Nicking gRNA position | Expected number of edited plants | Number of transgenic plants | Editing efficiency (%) of the PPE system |
| OsCDC48-T1 | +1-6 CTCCGG del | 12 | 9 | +37 | 12 | 55 | 21.8 |
| OsALS-T2 | +3 G to T | 10 | 17 | +33 | 2 | 14 | 14.3 |
| OsCDC48-T1 | +3-5 AG to CA | 12 | 15 | +76 | 1 | 38 | 2.6 |

Example 7 Influence of Tm of PBS on the Efficiency of PPE System

Figure 24:
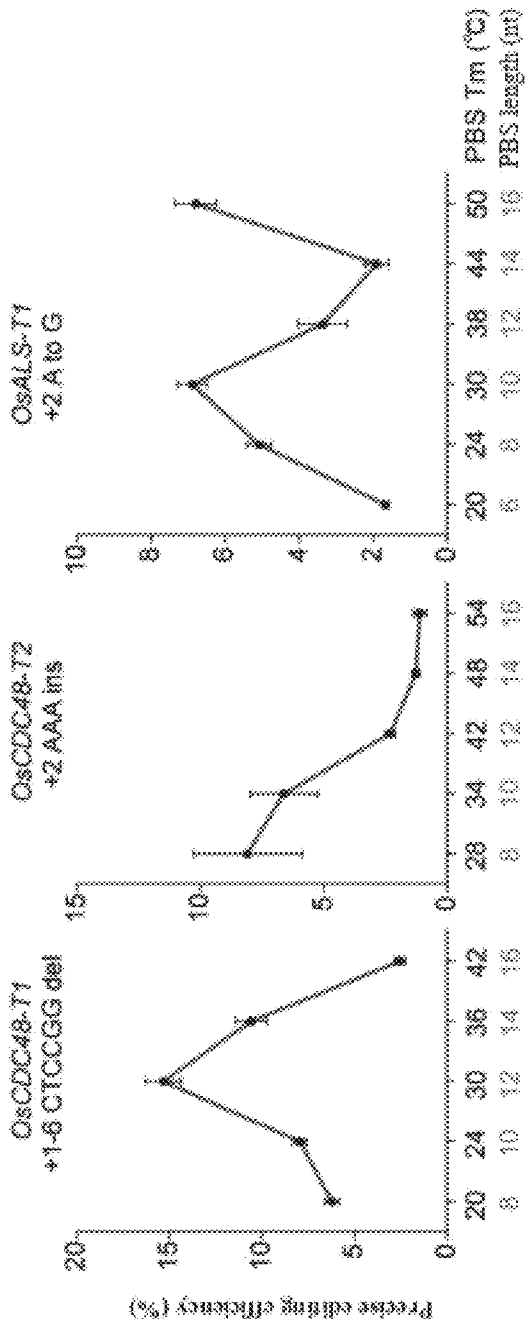
FIG. 24 shows comparison of influences of different Tm-guided PBS lengths on editing efficiency by using published data for three target sites and newly obtained data for ten new target sites in rice protoplasts.
Figure 24:
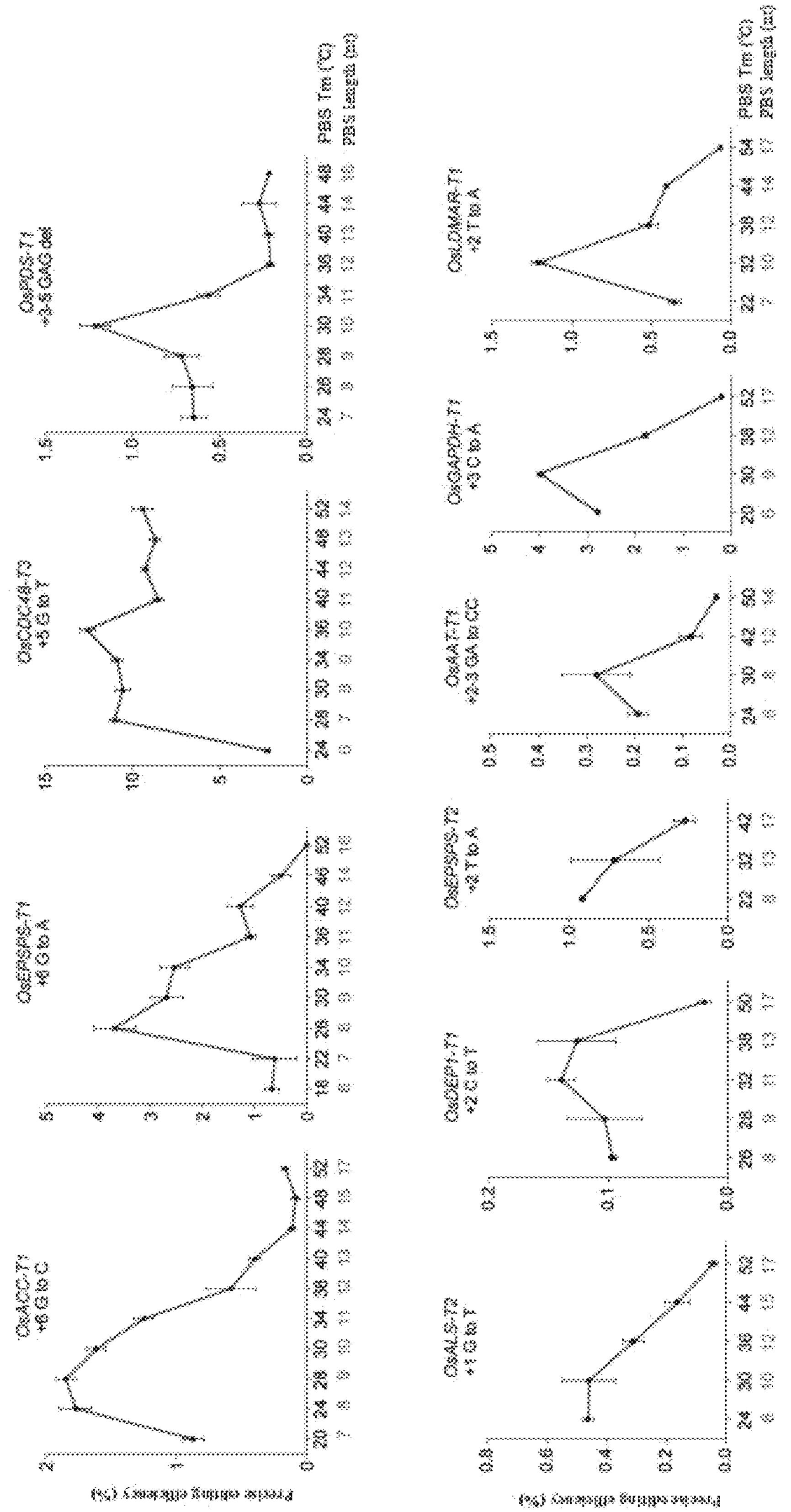

The influence of the PBS length which controls the Tm on prime editing in plants was first assessed based on published data (FIG. 24). The results show that the editing efficiency is very high when PBS Tm was close to 30° C. (30° C. for OsCDC48-T1, 28° C. for OsCDC48-T2 and 30° C. for OsALS-T1).

Then, the editing efficiency of PPE using PBS (corresponding to the PBS length of 6 nt to 17 nt) with a Tm of 18° C. to 52° C. was evaluated on the four target loci (OsACC-T1, OsCDC48-T3, OsEPSPS-T1 and OsPDS-T1) in rice protoplasts. The results are shown in FIG. 24. When PBS Tm was close to 30° C. (24-30° C. in OsACC-T1, 26-34° C. in OsEPSPS-T1, 28-36° C. in OsCDC48-T3, and 30° C. in OsPDS-T1), pegRNA had higher activity. The editing efficiency at these PBS Tm was 1.5 to 4.3 times higher than that at other PBS Tm. Additional six target loci were also tested (see FIG. 24), including OsALS-T2, OsDEP1-T1, OsEPSPS-T2, OsAAT-T1, OsGAPDH-T1 and OsLDMAR-T1, and it was found that five (except for OsEPSPS-T2) of the six target loci have similar conditions.

Figure 25:
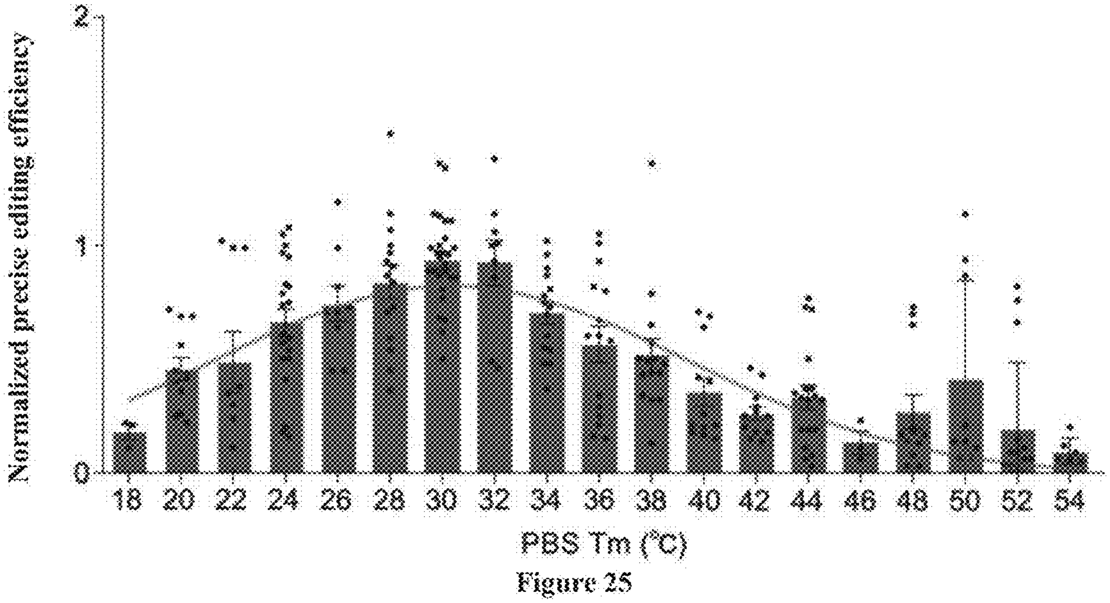
FIG. 25 shows normalization of priming editing frequencies with different PBS melting temperatures. The highest editing frequency obtained at each target is normalized to 1, and the frequencies obtained at other PBS Tins are adjusted accordingly.

Then, the overall editing efficiency of PPE on the 13 target loci at different PBS Tm was normalized and compared. The results show that the editing efficiency follows a normal distribution (P>0.1) (FIG. 25), typically reaches a maximum value when PBS Tm was 30° C., followed by 32° C. and 28° C., and the efficiency was decreased with increase or decrease of PBS Tm.

From this, it was concluded that the melting temperature of the PBS sequence is closely related to the editing efficiency of the PPE (FIG. 25) and is likely a major factor influencing the pegRNA design for plants. It is recommended to use PBS Tm of 30° C. to guide the design of pegRNA in PPE.

Figure 26:
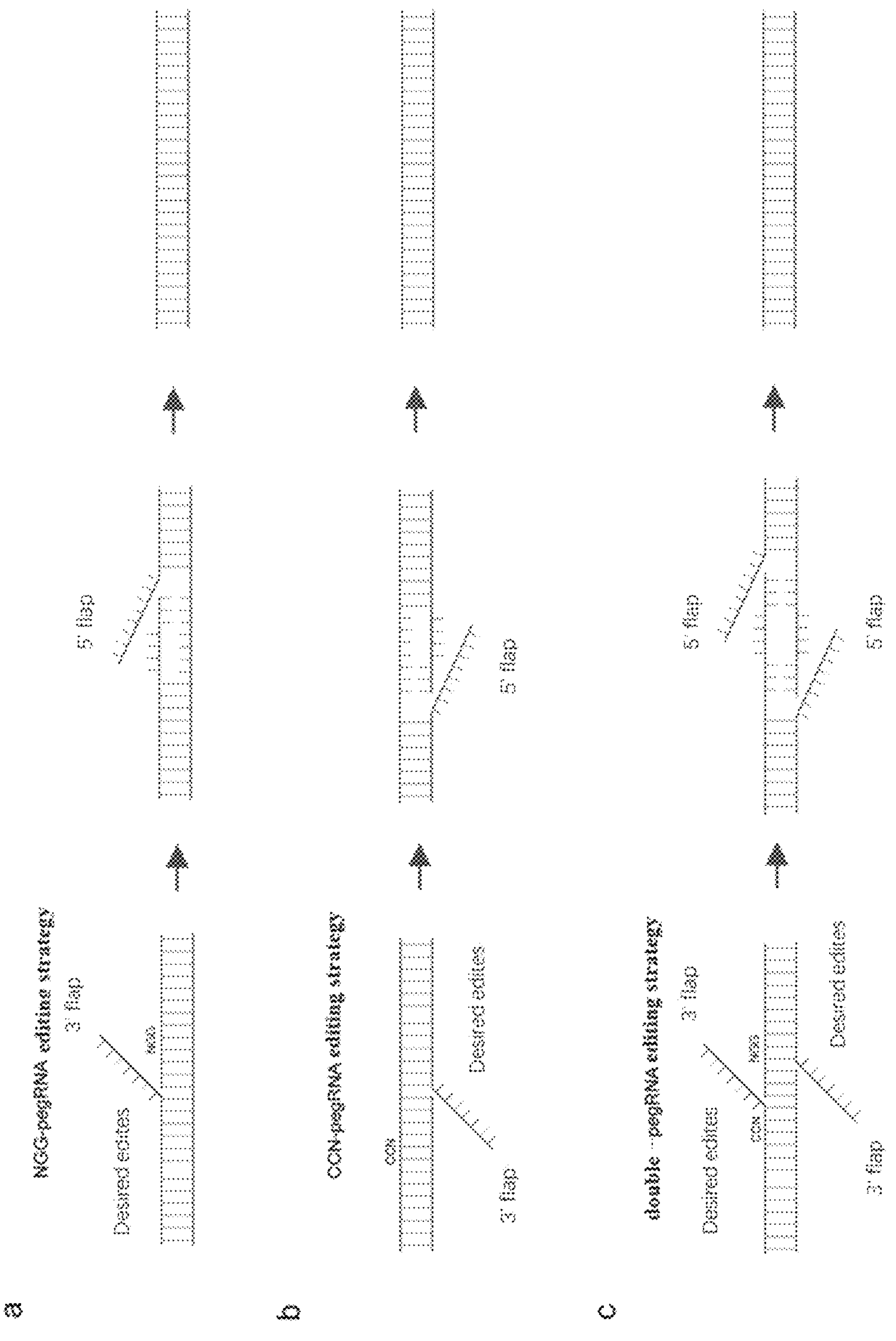
FIG. 26 shows a schematic diagram of priming editing by using single-pegRNA and double-pegRNA strategies. (a) Only an NGG-pegRNA is used for editing (a forward DNA strand is edited). (b) Only a CCN-pegRNA is used for editing (a reverse DNA strand is edited). (c) The double-pegRNA strategy is used for editing. Double-pegRNAs create two edits in the two DNA strands simultaneously.

Example 8 Dual pegRNA Strategy to Significantly Improve the Efficiency of PPE System In order to obtain optimal editing, the inventors developed a dual-pegRNA strategy which uses different pegRNAs against forward and reverse DNA strands (referred to as NGG-pegRNA and CCN-pegRNA, respectively) and simultaneously encoding a same edit (FIG. 26). 15 target loci were selected from ten rice genes, and a pair of pegRNAs were designed for each target (Table 3). Then, the editing activities of NGG-pegRNA, CCN-pegRNA and dual-pegRNA were compared at the same location.

TABLE 3

| Target sequence, RT template and PBS sequence of double-pegRNA | | | | | | | | |
|---|---|---|---|---|---|---|---|---|
| Genes | pegRNA | Target sequence | RT template and PBS sequence | Desired editing | Edited DNA strands | PBS length (nt) | RT length (nt) | Homo-logous arm length (nt) |
| OsCDC48 | NGG-pegRNA | GACCAGCCAGCGT<br>CTGGCGC**CGG**<br>(SEQ ID NO: 220) | TCAGCGGCGGCGCCTG<br>CG*CCAGACGCTGGC*<br>(SEQ ID NO: 221) | +4 C to A | Forward | 12 | 18 | 14 |
| OsCDC48 | CCN-pegRNA | **CCG**GCGCCAGACG<br>CTGGCTGGTC<br>(SEQ ID NO: 222) | CAGCGTCTGGCGCAGG<br>CG*CCGCCGCTGACC*<br>(SEQ ID NO: 223) | +5 G to T | Reverse | 12 | 18 | 13 |
| OsCDC48 | NGG-pegRNA | GACCAGCCAGCGT<br>CTGGCGC**CGG**<br>(SEQ ID NO: 224) | TCAGCGGCGGCGCTGG<br>CG*CCAGACGCTGGC*<br>(SEQ ID NO: 225) | +5 G to A | Forward | 12 | 18 | 13 |
| OsCDC48 | CCN-pegRNA | **CCG**GCGCCAGACG<br>CTGGCTGGTC<br>(SEQ ID NO: 226) | CAGCGTCTGGCGCCAG<br>CG*CCGCCGCTGACC*<br>(SEQ ID NO: 227) | +4 C to T | Reverse | 12 | 18 | 13 |
| OsALS | NGG-pegRNA | GTGCTGCCTATGAT<br>CCCAAG**TGG**<br>(SEQ ID NO: 228) | TGAATGCGCCCCCAATT<br>*GGGATCATAG*<br>(SEQ ID NO: 229) | +3 G to T | Forward | 10 | 17 | 14 |
| OsALS | CCN-pegRNA | **CCA**AGTGGGGGCG<br>CATTCAAGGA<br>(SEQ ID NO: 230) | TGCCTATGATCCCAATT<br>*GGGGGCGCAT*<br>(SEQ ID NO: 231) | +2 C to A | Reverse | 10 | 17 | 15 |

TABLE 3-continued

Target sequence, RT template and PBS sequence of double-pegRNA

| Genes | pegRNA | Target sequence | RT template and PBS sequence | Desired editing | Edited DNA strands | PBS length (nt) | RT length (nt) | Homo-logous arm length (nt) |
|---|---|---|---|---|---|---|---|---|
| OsALS | NGG-pegRNA | GTGCTGCCTATGAT CCCAAG**TGG** (SEQ ID NO: 232) | TGAATGCGCCCCCACC T*GGGATCATAG* (SEQ ID NO: 233) | +2 A to G | Forward | 10 | 17 | 15 |
| OsALS | CCN-pegRNA | **CCA**AGTGGGGGCG CATTCAAGGA (SEQ ID NO: 234) | TGCCTATGATCCCAGGT *GGGGGCGCAT* (SEQ ID NO: 235) | +3 T to C | Reverse | 10 | 17 | 14 |
| OsEPSPS | NGG-pegRNA | TACTAAATATACAA TCCCTT**GGG** (SEQ ID NO: 236) | ATAAACCCATG*GGATTG TATATTT* (SEQ ID NO: 237) | +2 T to A | Forward | 13 | 11 | 9 |
| OsEPSPS | CCN-pegRNA | **CCC**TTGGGTTTATT TGTTTCCAA (SEQ ID NO: 238) | ACAATCCCATG*GGTTTA TTTGTTT* (SEQ ID NO: 239) | +3 A to T | Reverse | 13 | 11 | 8 |
| OsEPSPS | NGG-pegRNA | ACTGTGACAGTTC AAGGTTG**TGG** (SEQ ID NO: 240) | TGCAAACTGGTAGTAC CACAA*CCTTGAACTG* (SEQ ID NO: 241) | +10 G to I | Forward | 10 | 21 | 11 |
| OsEPSPS | CCN-pegRNA | **CCA**GTTTGCAGGT ATAACTGTAG (SEQ ID NO: 242) | AAGGTTGTGGTACTAC CAGTTT*GCAGGTATAA* (SEQ ID NO: 243) | +8 C to A | Reverse | 11 | 21 | 13 |
| OsIPA1 | NGG-pegRNA | CTCTTCTGTCAACC CAGCCA**TGG** (SEQ ID NO: 244) | AGTATCCCATGC*CTGGG TTGAC* (SEQ ID NO: 245) | +1 C to G | Forward | 10 | 12 | 11 |
| OsIPA1 | CCN-pegRNA | **CCC**AGCCATGGGA TACTACTACC (SEQ ID NO: 246) | TGTCAACCCAGG*CATG GGATAC* (SEQ ID NO: 247) | +1 G to C | Reverse | 10 | 12 | 11 |
| OsIPA1 | NGG-pegRNA | TCTTCTGTCAACCC AGCCAT**TGG** (SEQ ID NO: 248) | GTAGTATCGCATG*GCTG GGTTGACAGAA* (SEQ ID NO: 249) | +5 G to C | Forward | 15 | 13 | 8 |
| OsIPA1 | CCN-pegRNA | **CCA**TGGGATACTA CTACCCACAG (SEQ ID NO: 250) | AACCCAGCCATGC*GAT ACTACTACCCAC* (SEQ ID NO: 251) | +2 C to G | Reverse | 15 | 13 | 11 |
| OsROC5 | NGG-pegRNA | TCTCACCTCTAGTA CCAATT**AGG** (SEQ ID NO: 252) | TGTAACCTCCCTA*TGGT ACTAGAGGTG* (SEQ ID NO: 253) | +1-2 AT del | Forward | 14 | 13 | 13 |
| OsROC5 | CCN-pegRNA | **CCA**ATTAGGGAGG TTACATTTCT (SEQ ID NO: 254) | CCTCTAGTACCAT*AGGG AGGTTACATT* (SEQ ID NO: 255) | +2-3 TA del | Reverse | 14 | 13 | 13 |
| OsDEP1 | NGG-pegRNA | GAGACAAGCTTGG CCCTCTT**TGG** (SEQ ID NO: 256) | CGCCACGCCCAAG*AGG GCCAAGCTT* (SEQ ID NO: 257) | +2 T del | Forward | 12 | 13 | 10 |
| OsDEP1 | CCN-pegRNA | **CCT**CTTTGGGCGT GGCGCCATGG (SEQ ID NO: 258) | AGCTTGGCCCTCT*TGG GCGTGGCGC* (SEQ ID NO: 259) | +2 A del | Reverse | 12 | 13 | 10 |
| OsDEP1 | NGG-pegRNA | AGCTTGGCCCTCTT TGGGCG**TGG** (SEQ ID NO: 260) | ACAGCCATGGCTCCAC GC*CCAAAGAGGG* (SEQ ID NO: 261) | +7 C to A | Forward | 10 | 18 | 11 |
| OsDEP1 | CCN-pegRNA | **CCA**TGGCTGTACT ACCTTTGTCG (SEQ ID NO: 262) | TTGGGCGTGGAGCCAT GG*CTGTACTACC* (SEQ ID NO: 263) | +8 G to T | Reverse | 10 | 18 | 10 |
| OsNRT1.1B | NGG-pegRNA | ACTAGATATCTAAA CCATTA**AGG** (SEQ ID NO: 264) | ATTTGACCTACCTTTAA *TGGTTTAGATATC* (SEQ ID NO: 265) | +2 A ins | Forward | 13 | 17 | 14 |
| OsNRT1.1B | CCN-pegRNA | **CCA**TTAAGGTAGG TCAAATCAAG (SEQ ID NO: 266) | GATATCTAAACCATTAA *AGGTAGGTCAAAT* (SEQ ID NO: 267) | +2 T ins | Reverse | 13 | 17 | 14 |

TABLE 3-continued

Target sequence, RT template and PBS sequence of double-pegRNA

| Genes | pegRNA | Target sequence | RT template and PBS sequence | Desired editing | Edited DNA strands | PBS length (nt) | RT length (nt) | Homo-logous arm length (nt) |
|---|---|---|---|---|---|---|---|---|
| OsNRT1.1B | NGG-pegRNA | CCTGTAGGTGTGTA TATACT**TGG** (SEQ ID NO: 268) | TAGTGCTGGTTCAAGTA *TATACACACC* (SEQ ID NO: 269) | +6 G to A | Forward | 11 | 16 | 10 |
| OsNRT1.1B | CCN-pegRNA | **CCA**GCACTACTAG ATATCTAAAC (SEQ ID NO: 270) | TATACTTGAACCAGCAC *TACTAGATAT* (SEQ ID NO: 271) | +8 C to T | Reverse | 11 | 16 | 8 |
| OsODEV | NGG-pegRNA | CACACACACACTA GTACCTC**TGG** (SEQ ID NO: 272) | AATAGTCCCCTAG*GTAC TAGTGTGT* (SEQ ID NO: 273) | +3-4 CT to AG | Forward | 12 | 13 | 9 |
| OsODEV | CCN-pegRNA | **CCT**CTGGGACTATT GTGTGTGTC (SEQ ID NO: 274) | ACTAGTACCTAGG*GGA CTATTGTGT* (SEQ ID NO: 275) | +2-3 GA to TC | Reverse | 12 | 13 | 9 |
| OsGAPDH | NGG-pegRNA | GAGTATGTCGTGG AGTCCAC**CGG** (SEQ ID NO: 276) | AGTGAAGACACCGCTG *GACTCCACGACA* (SEQ ID NO: 277) | +3 C to G | Forward | 12 | 16 | 13 |
| OsGAPDH | CCN-pegRNA | **CCA**CCGGTGTCTT CACTGACAAG (SEQ ID NO: 278) | GTCGTGGAGTCCAGCG *GTGTCTTCACTG* (SEQ ID NO: 279) | +3 G to C | Reverse | 12 | 16 | 13 |

PAM for each target locus is shown in bold, and PBS is italicized.

Figure 27:
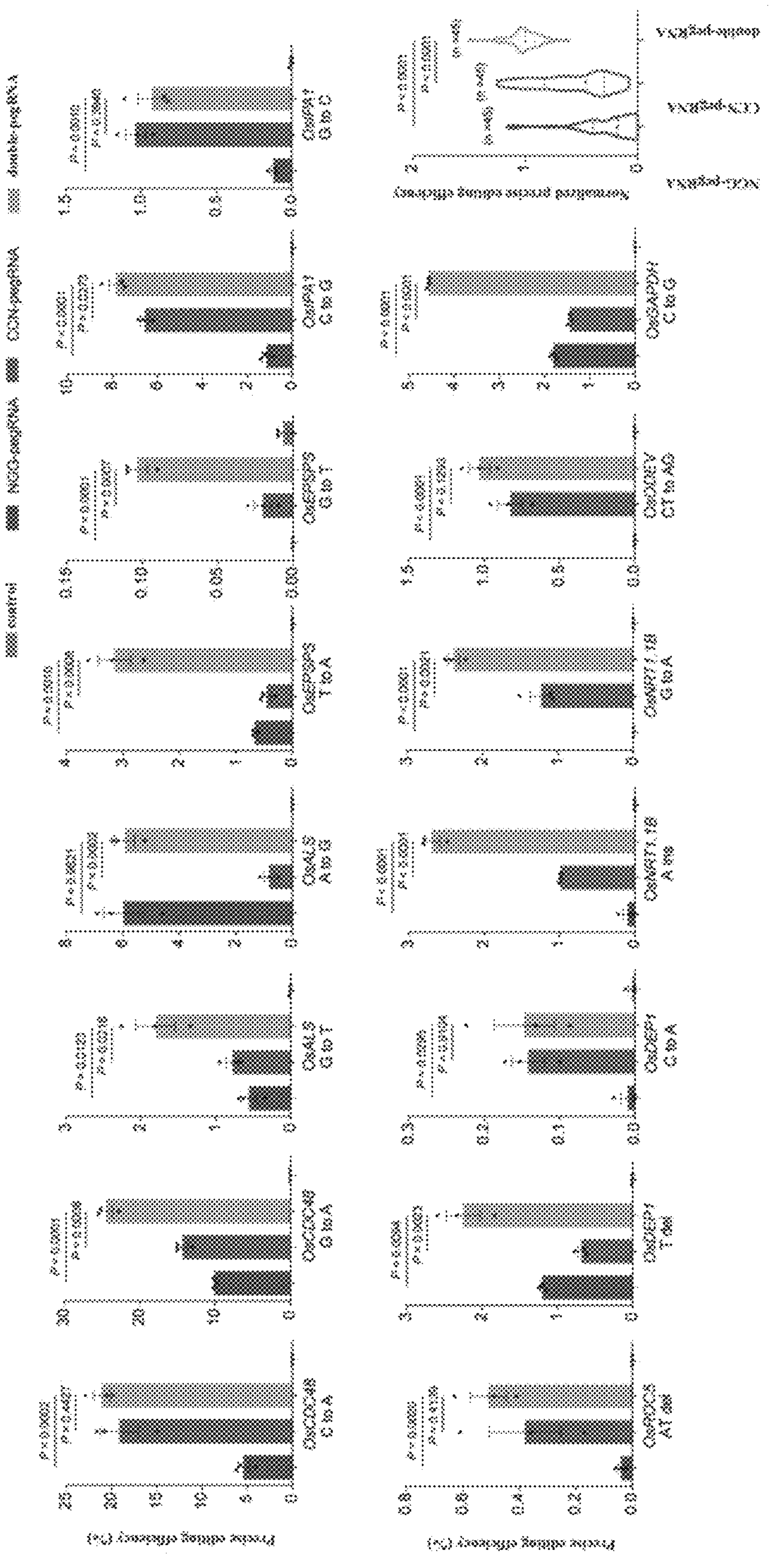
FIG. 27 shows comparison of editing efficiency induced by NGG-pegRNA, CCN-pegRNA and double-pegRNAs at 15 target sites.

As expected, the dual-pegRNA strategy has the highest activity on most of the target loci (13 of 15). Point mutations of C-to-A, G-to-A, G-to-T, A-to-G, T-to-A, C-to-G and CT-AG, 1 bp (T) or 2 bp (AT) deletion and 1 bp (A) insertion were generated, and the highest editing efficiency was 24.5% (FIG. 27).

Figure 28:
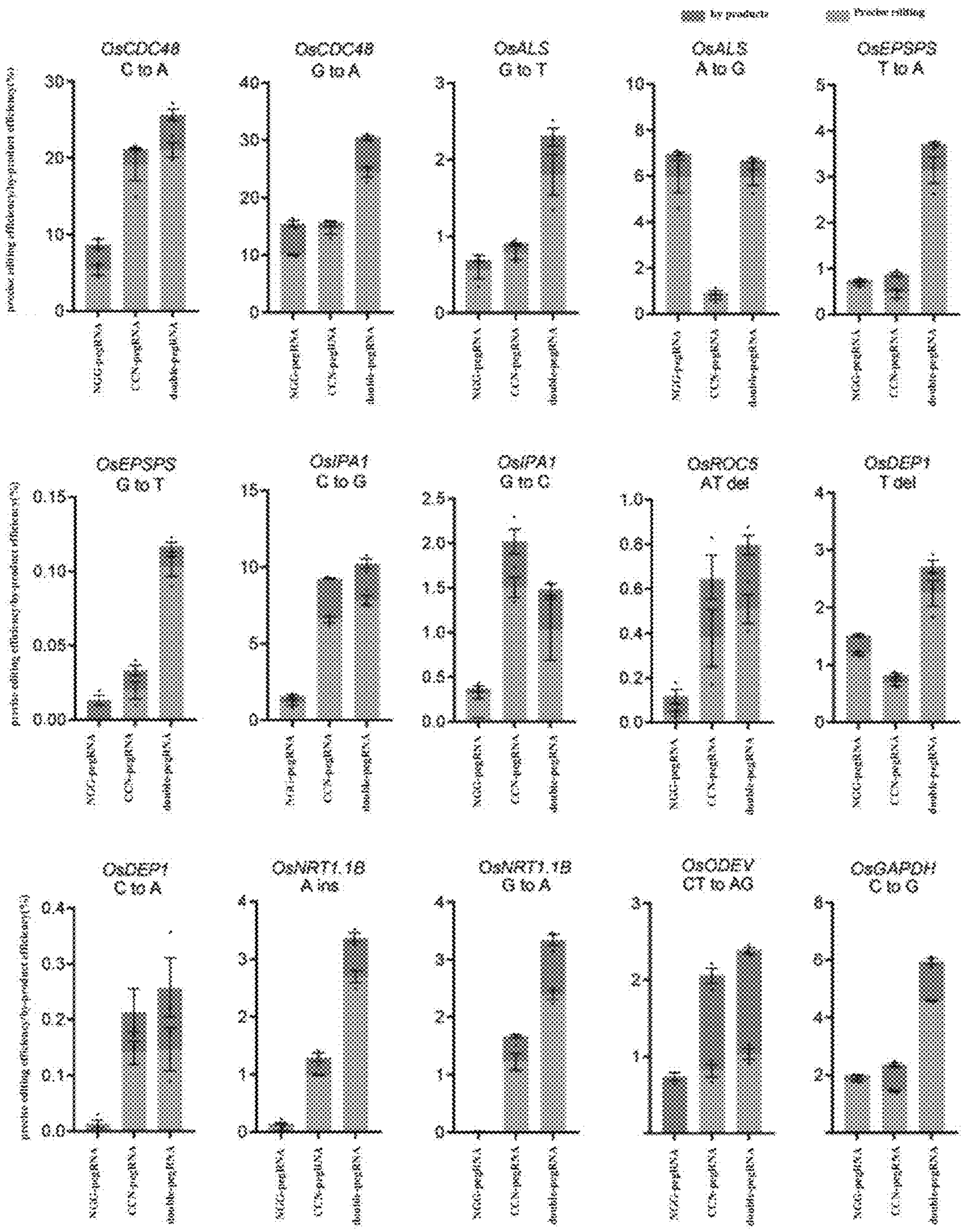
FIG. 28 shows product purity of editing at 15 endogenous sites of the rice protoplasts using NGG-pegRNA, CCN-pegRNA and double-pegRNAs.

The editing efficiency of double-pegRNA on all the test loci was about 4.2-times higher than that of single NGG-pegRNA (up to 27.9 times for OsNRT1.1B (insert A)), and 1.8-times higher than the average editing efficiency of single CCN-pegRNA (up to 7.2 times for OsALS (A-to-G)). Also, the proportion of by-products using double-pegRNA was not higher than that of single-pegRNA (FIG. 28).

Figure 29:
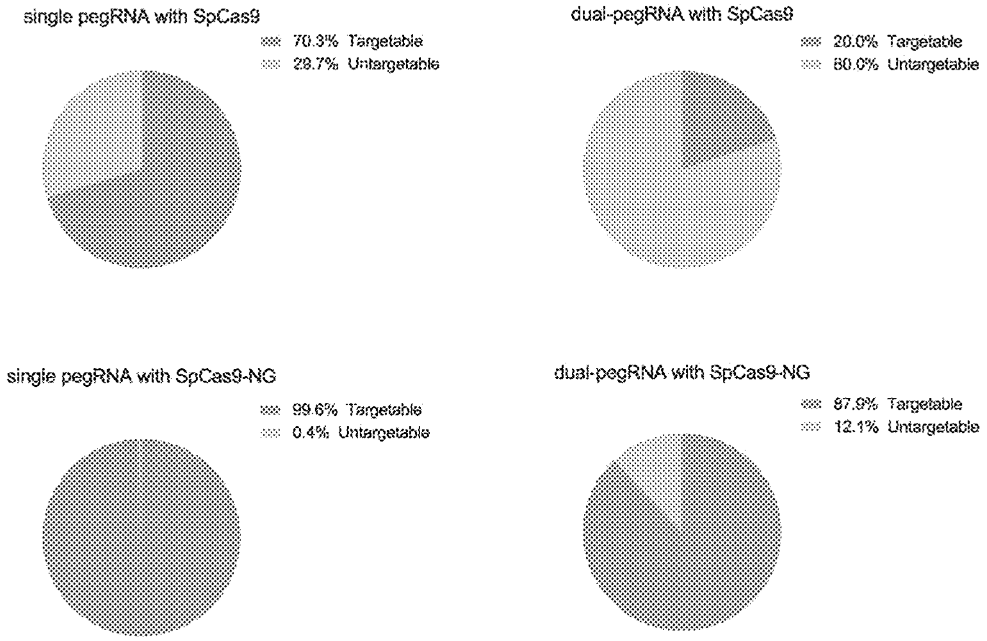
FIG. 29 shows the percentage of rice genomic bases that theoretically can be targeted by priming editing with single pegRNAs and double-pegRNAs.

Computational analysis based on the rice reference genome (Os-Nipponbare reference IRGSP-1.0) show that the dual-pegRNA can theoretically target 20.0% of the genome bases when a prime editing window was from +1 to +15. However, when combined with a SpCas9-NG variant having NG PAM, the dual-pegRNA strategy can target 87.9% of the rice bases (FIG. 29).

Sequence Description

SEQ ID NO: 1 Wild-type SpCas9 amino acid sequence
SEQ ID NO: 2 nCas9(H840A) amino acid sequence
SEQ ID NO: 3 Wild-type M-MLV amino acid sequence
SEQ ID NO: 4 M-MLV amino acid sequence of the present invention
SEQ ID NO: 5 The amino acid sequence of CaMV reverse transcriptase
SEQ ID NO: 6 The amino acid sequence of retron reverse transcriptase
SEQ ID NO: 7 32aa linker amino acid sequence
SEQ ID NO: 8 gRNA scaffold sequence
SEQ ID NO:9 The gene sequence of the fusion protein nCas9(H840A)-M-MLV of the present invention
SEQ ID NO: 10 The gene sequence of the fusion protein nCas9(H840A)-CaMV of the present invention
SEQ ID NO: 11 The gene sequence of the fusion protein nCas9(H840A)-retron of the present invention
SEQ ID NO: 12 The amino acid sequence of the fusion protein nCas9(H840A)-M-MLV of the present invention
SEQ ID NO: 13 The amino acid sequence of the fusion protein nCas9(H840A)-CaMV of the present invention
SEQ ID NO: 14 The amino acid sequence of the fusion protein nCas9(H840A)-retron of the present invention

What we claim is:

1. A method of producing a genetically modified plant, comprising:

providing a plant genome editing system for targeted modification of a plant genome comprising:

i) a fusion protein and/or an expression construct comprising a nucleotide sequence encoding the fusion protein, wherein the fusion protein comprises a CRISPR nickase and a reverse transcriptase; and ii) at least a pair of pegRNAs and/or an expression construct comprising a nucleotide sequence encoding the at least a pair of pegRNAs, wherein each of the pegRNAs comprises, in the direction from 5' to 3', a guide sequence, a scaffold sequence, a reverse transcription (RT) template sequence and a primer binding site (PBS) sequence, wherein each of the pegRNAs can form a complex with the fusion protein and target the fusion protein to a target sequence in the genome, so that a nick is formed in the target sequence; and introducing the plant genome editing system into at least one plant, thereby resulting in a modification in the genome of the at least one plant, wherein two pegRNAs in the pair of pegRNAs are configured to target different target sequences on the same strand of the genomic DNA, or the two pegRNAs in the pair of pegRNAs are configured to target the target sequences on different strands of the genomic DNA, wherein nicks induced by the two pegRNAs are located on two sides of the site to be modified, respectively.

2. The method of claim 1, wherein said introducing comprises transforming the plant genome editing system into an isolated plant cell or tissue, and then regenerating the transformed plant cell or tissue into an intact plant; or wherein said introducing comprises transforming the plant genome editing system into a specific part of an intact plant.

3. The method of claim 2, further comprising culturing the plant cell, tissue or intact plant into which the genome editing system has been introduced at an elevated temperature.

4. The method of claim 3, wherein the elevated temperature is 37° C.

5. The method of claim 1, wherein the CRISPR nickase is a Cas9 nickase.

6. The method of claim 5, wherein the CRISPR nickase is a Cas9 nickase comprising an amino acid sequence shown in SEQ ID NO: 2.

7. The method of claim 1, wherein the reverse transcriptase is a M-MLV reverse transcriptase shown in SEQ ID NO: 4, or the reverse transcriptase is a CaMV reverse transcriptase shown in SEQ ID NO: 5 or a retron reverse transcriptase shown in SEQ ID NO: 6.

8. The method of claim 1, wherein the guide sequence of the pegRNA is configured to have 100% sequence identity with the target sequence and thus can bind to a complementary strand of the target sequence by base pairing so as to achieve sequence-specific targeting.

9. The method of claim 1, wherein the scaffold sequence of the pegRNA comprises a sequence shown in SEQ ID NO: 8.

10. The method of claim 1, wherein the primer binding site sequence is complementary to at least a portion of a 3' free single strand caused by the nick, in particular to a nucleotide sequence at the 3' end of the 3' free single strand.

11. The method of claim 1, wherein the primer binding site sequence has a Tm (melting temperature) of about 24-36° C.

12. The method of claim 1, wherein the RT template sequence is configured to correspond to a sequence downstream of the nick and comprises a desired modification, and the modification comprises substitution, deletion and/or addition of one or more nucleotides.

13. The method of claim 1, wherein the plant genome editing system further comprises a nicking gRNA and/or an expression construct comprising a nucleotide sequence encoding the nicking gRNA, wherein the nicking gRNA comprises a guide sequence and a scaffold sequence, the guide sequence is configured to have sufficient sequence identity with a target sequence of the genome so that the fusion protein can target the target sequence and a nick can be formed in the target sequence, the target sequence of the nicking gRNA and the target sequence of the pegRNA are located on opposite strands of genomic DNA, and about 1 to about 300 nucleotides are present between the nick induced by the nicking gRNA and the nick induced by the pegRNA.

14. The method of claim 1, wherein PAM of the target sequence of one pegRNA in the pegRNA pair is located on a sense strand and PAM of the other pegRNA is located on an antisense strand.

15. The method of claim 1, wherein the nick induced by the pegRNA for the sense strand is located upstream (in the 5' direction) of the site to be modified, and the nick induced by the pegRNA for the antisense strand is located downstream (in the 3' direction) of the site to be modified.

16. The method of claim 15, wherein about 1 to about 300 or more nucleotides are presented between the nicks induced by the two pegRNAs.

17. The method of claim 16, wherein the two pegRNAs in the pegRNA pair are configured to introduce a same desired modification.

18. The method of claim 16, wherein about 1-15 nucleotides are presented between the nicks induced by the two pegRNAs.

19. The method of claim 1, wherein the modification comprises substitution, deletion and/or addition of one or more nucleotides.

* * * * *